US011478556B2

(12) United States Patent
Miller et al.

(10) Patent No.: US 11,478,556 B2
(45) Date of Patent: Oct. 25, 2022

(54) COMPOSITIONS AND METHODS FOR TREATING OR AMELIORATING NEUROINFLAMMATION, NEURODEGENERATION, NEUROPATHIC PAIN, AND MIGRAINE

(71) Applicant: The Regents of the University of California, Oakland, CA (US)

(72) Inventors: Yury Miller, La Jolla, CA (US); Tony L. Yaksh, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 13 days.

(21) Appl. No.: 16/909,896

(22) Filed: Jun. 23, 2020

(65) Prior Publication Data

US 2020/0390906 A1    Dec. 17, 2020

Related U.S. Application Data

(62) Division of application No. 16/060,576, filed as application No. PCT/US2016/064938 on Dec. 5, 2016, now Pat. No. 10,729,788.

(60) Provisional application No. 62/265,752, filed on Dec. 10, 2015.

(51) Int. Cl.

| | | |
|---|---|---|
| *C07K 14/00* | (2006.01) | |
| *A61P 25/06* | (2006.01) | |
| *C07K 14/775* | (2006.01) | |
| *A61K 48/00* | (2006.01) | |
| *A61K 38/52* | (2006.01) | |
| *A61P 25/28* | (2006.01) | |
| *A61P 29/00* | (2006.01) | |
| *C07K 14/075* | (2006.01) | |
| *C12N 9/90* | (2006.01) | |
| *C12N 15/62* | (2006.01) | |

(52) U.S. Cl.
CPC .......... *A61K 48/0058* (2013.01); *A61K 38/52* (2013.01); *A61P 25/06* (2018.01); *A61P 25/28* (2018.01); *A61P 29/00* (2018.01); *C07K 14/00* (2013.01); *C07K 14/075* (2013.01); *C07K 14/775* (2013.01); *C12N 9/90* (2013.01); *C12N 15/62* (2013.01); *C12N 2750/14143* (2013.01); *C12Y 501/99006* (2015.07)

(58) Field of Classification Search
CPC ..... A61K 48/0058; A61K 38/52; A61P 25/06; A61P 25/28; A61P 29/00; C07K 14/00; C07K 14/075; C07K 14/775; C12N 9/90; C12N 15/62; C12N 2750/14143; C12Y 501/99006

See application file for complete search history.

(56) References Cited

U.S. PATENT DOCUMENTS

2014/0187498 A1   7/2014   King et al.
2016/0115211 A1   4/2016   Miller et al.

FOREIGN PATENT DOCUMENTS

| CN | 100357325 | 12/2007 |
|---|---|---|
| WO | 2012019060 A1 | 2/2012 |
| WO | 2014193822 A1 | 12/2014 |

OTHER PUBLICATIONS

Fang et al., "Control of angiogenesis by AIBP-mediated cholesterol efflux" Nature, Jun. 6, 2013, v 498, p. 118-122.
Copenheaver, International Search Report for PCT/US2016/064938 dated Feb. 17, 2017.

*Primary Examiner* — Kimberly Ballard
*Assistant Examiner* — Stacey N MacFarlane
(74) *Attorney, Agent, or Firm* — Greer, Burns & Crain, Ltd.; Gregory P. Einhorn

(57) ABSTRACT

In alternative embodiments, provided are methods for increasing levels of and/or upregulating the expression of ApoA-I Binding Protein (APOA1BP, AIBP, or AI-BP) to treat, ameliorate, prevent, reverse, decrease the severity or duration of: a neuropathic pain, including an inflammation-induced neuropathic pain, a nerve or CNS inflammation, a, a post nerve injury pain, a post-surgical pain, a chemotherapeutic-induced peripheral neuropathy (CIPN) (e.g., cisplatin-induced allodynia) a neurodegeneration or neurodegenerative disease or condition, a migraine, and/or a hyperalgesia. In alternative embodiments, provided are methods comprising administering formulations and pharmaceutical compositions comprising an APOA1BP polypeptide or protein that is a human or a mammalian APOA1BP, or an AIBP1 or an AIBP2, or a recombinant, peptidomimetic or a synthetic APOA1BP, or a bioisostere of an ApoA-I Binding Protein to treat, ameliorate prevent, reverse, decrease the severity of a neuropathic pain, a TLR4-mediated allodynia and/or a hyperalgesia.

17 Claims, 32 Drawing Sheets
Specification includes a Sequence Listing.

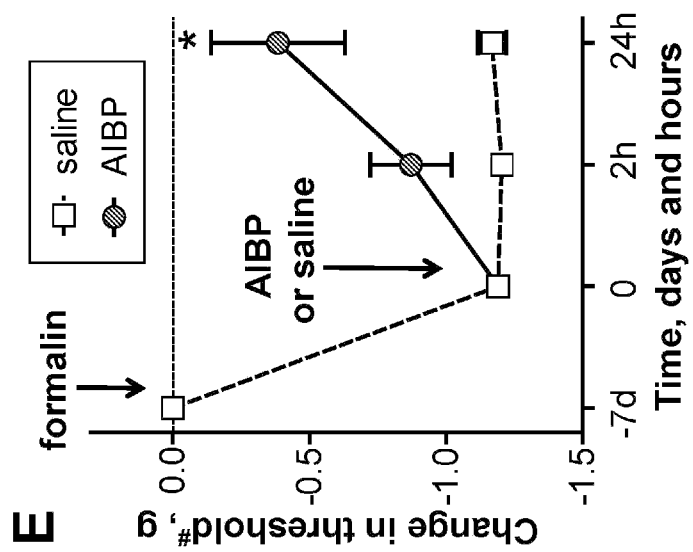
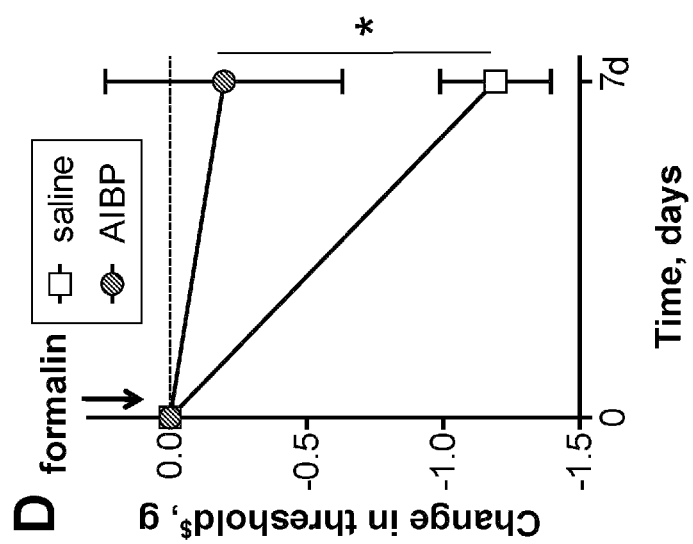
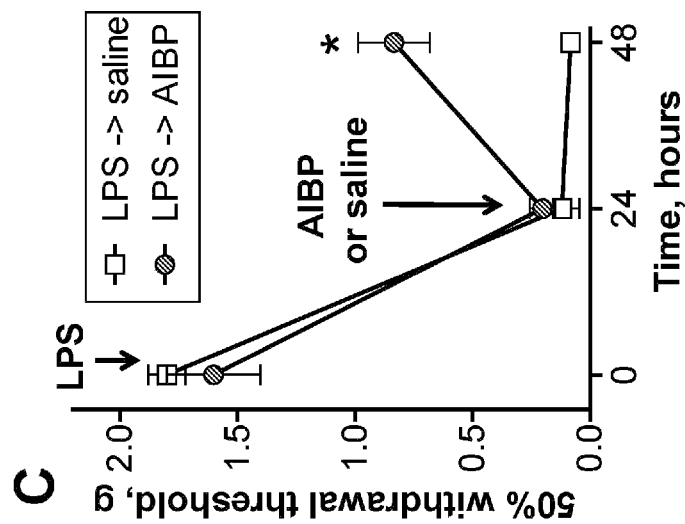
FIG. 13C
FIG. 13D
FIG. 13E

COMPOSITIONS AND METHODS FOR TREATING OR AMELIORATING NEUROINFLAMMATION, NEURODEGENERATION, NEUROPATHIC PAIN, AND MIGRAINE

RELATED APPLICATIONS

This application is divisional patent application under 35 U.S.C. § 121 to U.S. patent application Ser. No. 16/060,576, Jun. 8, 2018 (now pending), which is a national phase application claiming benefit of priority under 35 U.S.C. § 371 to Patent Convention Treaty (PCT) International Application serial number PCT/US2016/064938, filed Dec. 5, 2016, which claims priority under 35 U.S.C. § 119(e) of U.S. Provisional Application Ser. No. 62/265,752, filed Dec. 10, 2015. The aforementioned applications are expressly incorporated herein by reference in their entirety and for all purposes.

GOVERNMENT RIGHTS

This invention was made with government support under AR064194 and HL124174 awarded by the National Institutes of Health (NIH). The government has certain rights in the invention.

TECHNICAL FIELD

This invention generally relates to medicine, pain control and cell biology. In particular, in alternative embodiments, provided are methods for increasing levels of and/or upregulating the expression of ApoA-I Binding Protein (APOA1BP, AIBP, or AI-BP) to treat, ameliorate, prevent, reverse, decrease the severity and/or duration of: a neuropathic pain, a CNS inflammation, an allodynia, a post nerve injury pain, a post-surgical pain, a chemotherapeutic-induced peripheral neuropathy (CIPN) (e.g., cisplatin-induced allodynia) a neurodegeneration, including e.g., a neurodegenerative disease or condition such as Alzheimer's disease, a hyperalgesia, and/or primary headaches such as migraines and cluster headaches. In alternative embodiments, provided are methods comprising administering formulations and pharmaceutical compositions comprising an APOA1BP polypeptide or protein that is a human or a mammalian APOA1BP, or a recombinant, peptidomimetic or a synthetic APOA1BP, or a bioisostere of an ApoA-I Binding Protein to treat, ameliorate prevent, reverse, decrease the severity of a neuropathic pain, an allodynia, a hyperalgesia, a neurodegenerative disease or condition such as Alzheimer's disease, and/or a primary headache such as a migraine.

BACKGROUND

Apolipoprotein A-1 Binding Protein, or ApoA-I binding protein (AIBP), also called also called NAXE, NAD(P)HX epimerase, is a secreted protein discovered in a screen of proteins that physically associate with apoA-I (8). The human AIBP gene (APOA1BP) is located at 1q22. AIBP is a secreted protein. It has a presumed N-terminal signal peptide, which likely is cleaved off the protein during protein secretion from the cell.

Persistent pain states (greater than 3 months), arising from inflammatory disease (e.g., arthritis, 41 million people in the US; cancer, 8.5 million; and back pain, 6 million[1]) have extraordinary negative impact on quality of life. While opiates, NSAIDs, and anticonvulsants can relieve pain for short intervals, they are less effective for chronic therapy, particularly when components of the pain state involve persistent inflammation and/or injury to the peripheral nerve[2-4]. Aside from efficacy, many of the potent agents are beset with limiting side effects and issues related to dependence and addiction[5]. This relative lack of long-term efficacy of even approved agents is evident from clinical trial results, which often indicate that most subjects complete even successful trials with pain that is sufficiently severe as to permit reentry into the same trial[6].

The pain states arising from local tissue injury or inflammation typically show a time course that parallels the onset and resolution of the injury state[7], whereas nerve injury leads to a persistent pain state. However, as reported in humans, there is a growing appreciation that the pain originating from prolonged inflammation may persist even when the inflammatory state resolves, i.e. neutrophils, macrophages or cytokines are no longer detected. Thus, following surgeries such as hemiorrhaphies, arthroscopies and thoracotomies, up to 30% of the populations may show pain that last greater than 3 months[8,9]. In the classic clinical example of persistent inflammation, rheumatoid arthritis is characterized by joint inflammation, joint remodeling, and pain. While the association of pain with inflammation is not unexpected, patients continue to report moderate to severe pain despite remission or showing minimal inflammatory signs[10,11], suggesting the development of a chronic pain state.

SUMMARY

In alternative embodiments, provided are methods and uses for treating, ameliorating, preventing, reversing or decreasing the severity or duration of:

a neuropathic pain, an inflammation-induced neuropathic pain, wherein optionally the inflammation-induced neuropathic pain comprises a Toll-like receptor 4 (TLR4)-mediated inflammation-induced neuropathic pain, nerve or central nervous system (CNS) inflammation, wherein optionally the nerve or CNS inflammation comprises a TLR4-mediated nerve or CNS inflammation, an allodynia, wherein optionally the allodynia comprises a TLR4-mediated allodynia, —a post nerve or tissue injury pain or neuropathic pain, wherein optionally the post nerve or tissue injury pain or neuropathic pain is generated or caused by, or is a sequelae to, trauma, chemotherapy, arthritis, diabetes, or viral infection, a post-surgical pain or neuropathic pain, a chemotherapeutic-induced peripheral neuropathy (CIPN) (e.g., a cisplatin-induced CIPN or allodynia), wherein optionally the allodynia comprises a TLR4-mediated allodynia, a neurodegenerative disease or condition, optionally a chronic or progressive neurodegenerative disease or condition, optionally Alzheimer's disease or a Chronic Traumatic Encephalopathy (CTE) or a related tauopathy, a traumatic brain injury (TBI), a posttraumatic stress disorder, a traumatic war neurosis, or a post-traumatic stress syndrome (PTSS), a primary headache, optionally a migraine or a cluster headache, and/or a hyperalgesia, in a subject by adding, increasing levels of and/or upregulating the expression of an ApoA-I Binding Protein (APOA1BP, AIBP, or AI-BP), wherein the method comprises:

(a) providing a formulation or a pharmaceutical composition comprising:

(i) an ApoA-I Binding Protein (APOA1BP, AIBP, or AI-BP) polypeptide compound or composition, or a compound that increases expression or activity of, or encodes, a APOA1BP polypeptide or nucleic acid, or a polypeptide or peptide having an APOA1BP activity, or an APOA1BP-stimulating compound or composition;

(ii) the formulation or pharmaceutical composition of (i), wherein the compound that increases expression or activity of, or encodes, a APOA1BP polypeptide is a nucleic acid that expresses or encodes a APOA1BP polypeptide or a polypeptide having a APOA1BP polypeptide activity, and optionally a APOA1BP-stimulating compound or composition increases or stimulates (activates) the activity of a APOA1BP promoter or transcriptional regulatory sequence or motif, and optionally the nucleic acid that expresses or encodes a APOA1BP polypeptide or a polypeptide having a APOA1BP polypeptide activity is contained in an expression vehicle, vector, recombinant virus, or equivalent, and optionally the vector or virus is or comprises an adenovirus vector or an adeno-associated virus (AAV) vector, a retrovirus, a lentiviral vector, a herpes simplex virus, a human immunodeficiency virus (HIV), or a synthetic vector, and optionally the AAV vector comprises or is:

an adeno-associated virus (AAV), or an adenovirus vector, an AAV serotype or variant AAV5, AAV6, AAV8 or AAV9, AAV-DJ or AAV-DJ/8™ (Cell Biolabs, Inc., San Diego, Calif.), a rhesus-derived AAV, or the rhesus-derived AAV AAVrh.10hCLN2, an AAV capsid mutant or AAV hybrid serotype, an organ-tropic AAV, or a cardiotropic AAV, or a cardiotropic AAVM41 mutant, wherein optionally the AAV is engineered to increase efficiency in targeting a specific cell type that is non-permissive to a wild type (wt) AAV and/or to improve efficacy in infecting only a cell type of interest, and optionally the hybrid AAV is retargeted or engineered as a hybrid serotype by one or more modifications comprising: 1) a transcapsidation, 2) adsorption of a bi-specific antibody to a capsid surface, 3) engineering a mosaic capsid, and/or 4) engineering a chimeric capsid;

(iii) an ApoA-I Binding Protein (APOA1BP, AIBP, or AI-BP)-inducing compound or composition;

(iv) the formulation or pharmaceutical composition of any of (i) to (iii), wherein the an ApoA-I Binding Protein (APOA1BP, AIBP, or AI-BP) polypeptide or protein is a human or a mammalian APOA1BP, or a AIBP1 or a AIBP2, or a recombinant, peptidomimetic or a synthetic APOA1BP, or a bioisostere of an ApoA-I Binding Protein (APOA1BP, AIBP, or AI-BP);

(v) the formulation or pharmaceutical composition of any of (i) to (iv), formulated for administration in vivo; or formulated for enteral or parenteral administration, or for oral, subcutaneous (SC), intramuscular (IM), intravenous (IV) or intrathecal (IT) administration, wherein optionally the formulation or pharmaceutical composition, or the recombinant, peptidomimetic or a synthetic APOA1BP, or bioisostere of APOA1BP, or nucleic acid encoding the APOA1BP, or vector having contained therein a nucleic acid encoding the APOA1BP, is carried in a nanoparticle, a particle, a micelle or a liposome or lipoplex, a polymersome, a polyplex or a dendrimer, which optionally can further comprise or express a cell or CNS penetrating moiety or peptide or a CNS targeting moiety or peptide; or (vi) the formulation or pharmaceutical composition of any of (i) to (v), formulated for as a nanoparticle, a liposome, a tablet, a pill, a capsule, a gel, a geltab, a liquid, a powder, an emulsion, a lotion, an aerosol, a spray, a lozenge, an aqueous or a sterile or an injectable solution, or an implant (e.g., an intrathecal implant); and (b) administering the formulation or the pharmaceutical composition of (a) to a subject in need thereof, wherein optionally the subject is a human or an animal, thereby treating, ameliorating, preventing, reversing or decreasing the severity or duration of the:

neuropathic pain, inflammation-induced neuropathic pain, wherein optionally the inflammation-induced neuropathic pain comprises a Toll-like receptor 4 (TLR4)-mediated inflammation-induced neuropathic pain, inflammation-induced neuropathic pain, nerve or CNS inflammation, wherein optionally the nerve or CNS inflammation comprises a TLR4-mediated nerve or CNS inflammation, allodynia, wherein optionally the allodynia comprises a TLR4-mediated allodynia, a post nerve or tissue injury pain or neuropathic pain, wherein optionally the post nerve or tissue injury pain or neuropathic pain is generated or caused by, or is a sequelae to, trauma, chemotherapy, arthritis, diabetes, or viral infection, post-surgical pain or neuropathic pain, chemotherapeutic-induced peripheral neuropathy (CIPN) (e.g., a cisplatin-induced CIPN or allodynia), a neurodegenerative disease or condition, optionally a chronic or progressive neurodegenerative disease or condition, optionally Alzheimer's disease or a Chronic Traumatic Encephalopathy (CTE) or a related tauopathy, a traumatic brain injury (TBI), a posttraumatic stress disorder, a traumatic war neurosis, or a post-traumatic stress syndrome (PTSS), a primary headache, optionally a migraine or a cluster headache, and/or hyperalgesia.

In alternative embodiments, provided are kits comprising a formulation or a pharmaceutical composition used in a method or use as provided herein, and optionally comprising instructions on practicing a method or use as provided herein.

In alternative embodiments, provided are Uses of a formulation or a pharmaceutical composition as used in a method provided herein, in the manufacture of a medicament.

In alternative embodiments, provided are Uses of a formulation or a pharmaceutical composition as used in a method provided herein, in the manufacture of a medicament for treating, ameliorating, preventing, reversing and/or decreasing the severity or duration of: —neuropathic pain, inflammation-induced neuropathic pain,
  wherein optionally the inflammation-induced neuropathic pain comprises a Toll-like receptor 4 (TLR4)-mediated inflammation-induced neuropathic pain,
inflammation-induced neuropathic pain,
nerve or CNS inflammation,
  wherein optionally the nerve or CNS inflammation comprises a TLR4-mediated nerve or CNS inflammation,
allodynia,
  wherein optionally the allodynia comprises a TLR4-mediated allodynia,
a post nerve or tissue injury pain or neuropathic pain,
  wherein optionally the post nerve or tissue injury pain or neuropathic pain is generated or caused by, or is a sequelae to, trauma, chemotherapy, arthritis, diabetes, or viral infection,
post-surgical pain or neuropathic pain,
chemotherapeutic-induced peripheral neuropathy (CIPN) (e.g., a cisplatin-induced CIPN or allodynia),
a neurodegenerative disease or condition, optionally a chronic or progressive neurodegenerative disease or condition, optionally Alzheimer's disease or a Chronic Traumatic Encephalopathy (CTE) or a related tauopathy, a traumatic brain injury (TBI), a posttraumatic stress disorder, a traumatic war neurosis, or a post-traumatic stress syndrome (PTSS),
a primary headache, optionally a migraine or a cluster headache, and/or
hyperalgesia In alternative embodiments, provided are formulations, pharmaceutical compositions or therapeutic combinations for use in a method for treating, ameliorating, preventing, reversing or decreasing the severity and/or duration of:
neuropathic pain,
inflammation-induced neuropathic pain,
  wherein optionally the inflammation-induced neuropathic pain comprises a Toll-like receptor 4 (TLR4)-mediated inflammation-induced neuropathic pain,
inflammation-induced neuropathic pain,
nerve or CNS inflammation,
  wherein optionally the nerve or CNS inflammation comprises a TLR4-mediated nerve or CNS inflammation,
allodynia,
  wherein optionally the allodynia comprises a TLR4-mediated allodynia,
a post nerve or tissue injury pain or neuropathic pain,
  wherein optionally the post nerve or tissue injury pain or neuropathic pain is generated or caused by, or is a sequelae to, trauma, chemotherapy, arthritis, diabetes, or viral infection,
post-surgical pain or neuropathic pain,
chemotherapeutic-induced peripheral neuropathy (CIPN) (e.g., a cisplatin-induced CIPN or allodynia),
a neurodegenerative disease or condition, optionally a chronic or progressive neurodegenerative disease or condition, optionally Alzheimer's disease or a Chronic Traumatic Encephalopathy (CTE) or a related tauopathy, a traumatic brain injury (TBI), a posttraumatic stress disorder, a traumatic war neurosis, or a post-traumatic stress syndrome (PTSS),
a primary headache, optionally a migraine or a cluster headache, and/or
hyperalgesia
wherein the formulation or a therapeutic combination comprises one of, all or several of:

(i) an ApoA-I Binding Protein (APOA1BP, AIBP, or AI-BP) polypeptide compound or composition, or a compound that increases expression or activity of, or encodes, a APOA1BP polypeptide or nucleic acid, or a polypeptide or peptide having an APOA1BP activity, or an APOA1BP-stimulating compound or composition;

(ii) the formulation or pharmaceutical composition of (i), wherein the compound that increases expression or activity of, or encodes, a APOA1BP polypeptide is a nucleic acid that expresses or encodes a APOA1BP polypeptide or a polypeptide having a APOA1BP polypeptide activity,
  and optionally a APOA1BP-stimulating compound or composition increases or stimulates (activates) the activity of a APOA1BP promoter or transcriptional regulatory sequence or motif,
  and optionally the nucleic acid that expresses or encodes a APOA1BP polypeptide or a polypeptide having a APOA1BP polypeptide activity is contained in an expression vehicle, vector, recombinant virus, or equivalent, and optionally the vector or virus is or comprises an adenovirus vector or an adeno-associated virus (AAV) vector, a retrovirus, a lentiviral vector, a herpes simplex virus, a human immunodeficiency virus (HIV), or a synthetic vector,
  and optionally the AAV vector comprises or is:
    an adeno-associated virus (AAV), or an adenovirus vector,
    an AAV serotype or variant AAV5, AAV6, AAV8 or AAV9, AAV-DJ or AAV-DJ/8™ (Cell Biolabs, Inc., San Diego, Calif.),
    a rhesus-derived AAV, or the rhesus-derived AAV AAVrh.10hCLN2,
    an AAV capsid mutant or AAV hybrid serotype,
    an organ-tropic AAV, or a cardiotropic AAV, or a cardiotropic AAVM41 mutant,
    wherein optionally the AAV is engineered to increase efficiency in targeting a specific cell type that is non-permissive to a wild type (wt) AAV and/or to improve efficacy in infecting only a cell type of interest,
    and optionally the hybrid AAV is retargeted or engineered as a hybrid serotype by one or more modifications comprising: 1) a transcapsidation, 2) adsorption of a bi-specific antibody to a capsid surface, 3) engineering a mosaic capsid, and/or 4) engineering a chimeric capsid;

(iii) an ApoA-I Binding Protein (APOA1BP, AIBP, or AI-BP)-inducing compound or composition;

(iv) the formulation or pharmaceutical composition of any of (i) to (iii), wherein the an ApoA-I Binding Protein (APOA1BP, AIBP, or AI-BP) polypeptide or protein is a human or a mammalian APOA1BP, or a AIBP1 or a AIBP2, or a recombinant, peptidomimetic or a synthetic APOA1BP, or a bioisostere of an ApoA-I Binding Protein (APOA1BP, AIBP, or AI-BP);

(v) the formulation or pharmaceutical composition of any of (i) to (iv), formulated for administration in vivo; or formulated for enteral or parenteral administration, or for oral, subcutaneous (SC), intramuscular (IM), intravenous (IV) or intrathecal (IT) administration,
wherein optionally the formulation or pharmaceutical composition, or the recombinant, peptidomimetic or a synthetic APOA1BP, or bioisostere of APOA1BP, or nucleic acid encoding the APOA1BP, or vector having contained therein a nucleic acid encoding the APOA1BP, is carried in a nanoparticle, a particle, a micelle or a liposome or lipoplex, a polymersome, a polyplex or a dendrimer, which optionally can further comprise or express a cell or CNS penetrating moiety or peptide or a CNS targeting moiety or peptide; or (vi) the formulation or pharmaceutical composition of any of (i) to (v), formulated for as a nanoparticle, a liposome, a tablet, a pill, a capsule, a gel, a geltab, a liquid, a powder, an emulsion, a lotion, an aerosol, a spray, a lozenge, an aqueous or a sterile or an injectable solution, or an implant (e.g., an intrathecal implant), and wherein the formulation or a therapeutic combination is administered to an individual or patient in need thereof.

The details of one or more embodiments of the invention are set forth in the accompanying drawings and the description below. Other features, objects, and advantages of the invention will be apparent from the description and drawings, and from the claims.

All publications, patents, patent applications cited herein are hereby expressly incorporated by reference for all purposes to the same extent as if each individual publication, patent, or patent application was specifically and individually indicated to be incorporated by reference.

BRIEF DESCRIPTION OF THE DRAWINGS

The drawings set forth herein are illustrative of embodiments provided herein and are not meant to limit the scope of the invention as encompassed by the claims.

FIG. 13A, FIG. 13B, FIG. 13C, FIG. 13D, FIG. 13E, FIG. 13F illustrate data showing that intrathecal AIBP prevents and reverses allodynia, as discussed in detail in Example 2, below.

Like reference symbols in the various drawings indicate like elements.

Figure 1:
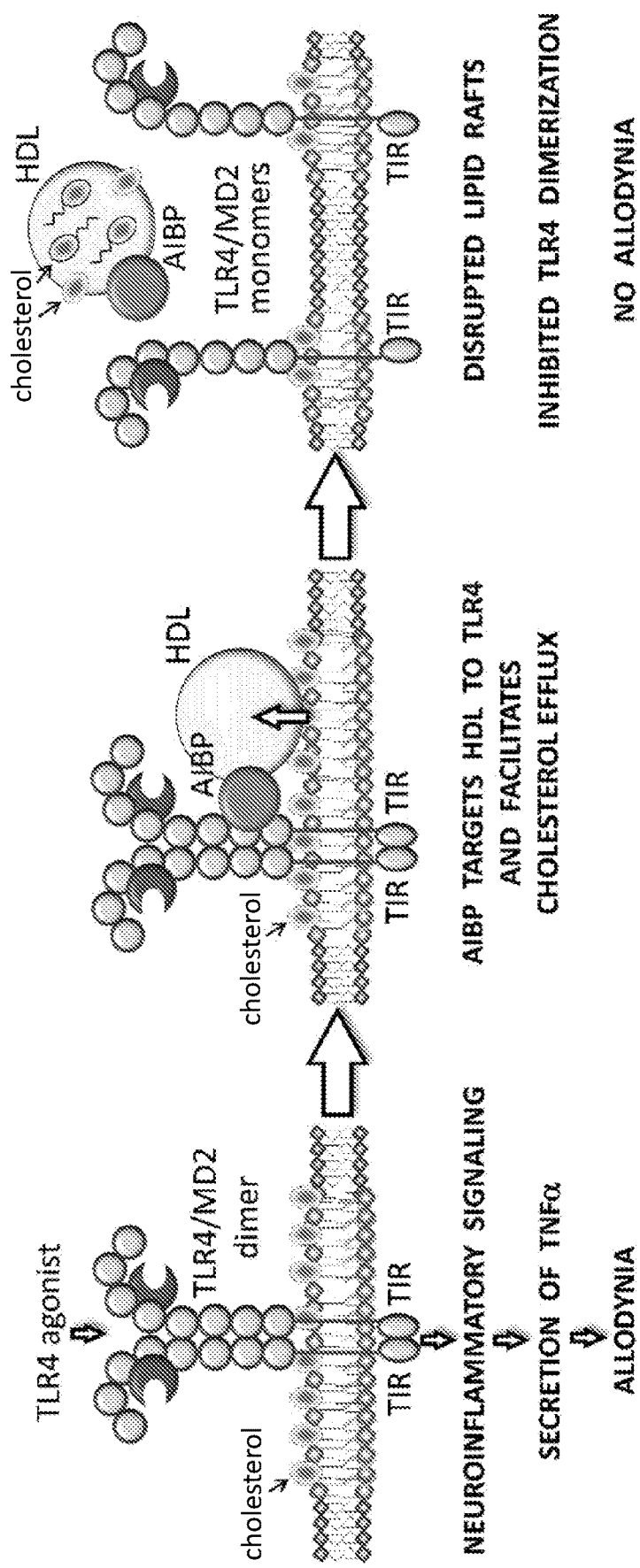
FIG. 1 schematically illustrates how AIBP targets Toll-like receptor 4 (TLR4)-occupied lipid rafts, facilitates cholesterol efflux and inhibits TLR4-mediated neuroinflammatory mechanisms of neuropathic pain, as discussed in detail in Example 1, below.

Reference will now be made in detail to various exemplary embodiments provided herein, examples of which are illustrated in the accompanying drawings. The following detailed description is provided to give the reader a better understanding of certain details of aspects and embodiments of the invention, and should not be interpreted as a limitation on the scope of the invention.

DETAILED DESCRIPTION

In alternative embodiments, provided are compositions and methods using pharmaceutical compounds and formulations comprising nucleic acids, polypeptides, and gene and polypeptide delivery vehicles for regulating or manipulating, including adding, maintaining, enhancing or upregulating, the expression of ApoA-I Binding Protein (APOA1BP, AIBP, or AI-BP), and kits comprising all or some of the components for practicing these compositions and methods. In alternative embodiments, provided are compositions and methods for delivering therapeutic levels of AIBP to the body, including the brain and CNS, including use of delivery vehicles targeting and/or capable of penetrating the blood brain barrier, and nucleic acid (gene) delivery vehicles such as vectors and viruses such as an adeno-associated virus (AAV) delivery vehicle having contained within an AIBP expressing nucleic acid; and for direct delivery of either AIBP polypeptide or AIBP-expressing nucleic acid directly via intrathecal (i.t.) administration.

In the course of studies on the role of lipid rafts in cellular receptor protein trafficking, we unexpectedly discovered that the apoA-I binding protein (AIBP) is an important regulatory component, and that elevating the neuraxial levels of AIBP regulates the manifestation of post nerve injury pain states.

In our study of passive K/BxN serum transfer model of arthritis, we inadvertently used C3H/HeJ mice, which are constitutively deficient in functional Toll-like receptor 4 (TLR4)[12]. We unexpectedly found profound attenuation of the late, but not early phase allodynia (allodynia is the experience of pain from a non-painful stimulation of the skin, such as light touch). Similarly, TLR4 knockout had no effect upon baseline measures or allodynia observed in the early inflammatory phase (up to day 6), but surprisingly prevented persistent allodynia in the late phase. This effect was mimicked by intrathecal (i.t.) injections of LPS-RS, a TLR4 antagonist, during the day 6-9 interval[13]. Importantly, TLR4 knockout prevented late phase increases in spinal cytokines and activation of spinal glia and dorsal root ganglia (DRG) ATF3. Noting that this invention is not limited by any particular mechanism of action, TLR4 was demonstrated to be critical in mediating the transition from acute to persistent pain. Similar data have been generated following nerve injury and treatment with chemotherapeutics in our lab and by others[14-18].

TLR4 and other receptors involved in inflammatory signaling localize, constitutively or upon ligand binding, to lipid rafts, which are membrane microdomains characterized by high content of cholesterol and sphingomyelin[19-22]. Receptors lacking signaling domains, such as CD14 which delivers ligands to TLR4, also reside in lipid rafts, and the decreased diffusion rates present in lipid rafts support TLR4 dimerization, which is an obligatory step in its signaling cascade[23,24].

In alternative embodiments, provided are compositions and methods for delivering therapeutically effective amounts of AIBP (either in the form of AIBP polypeptide or AIBP-expressing nucleic acid) to specifically target and facilitate cholesterol efflux in TLR4-occupied lipid rafts for the selective regulation of inflammatory responses, including neuroinflammation and associated pain and allodynia. Cholesterol is a structural component of any cellular membrane and its content is particularly high in lipid rafts. Cholesterol removal from lipid rafts disrupts TLR4 signaling[25]. Treatment with methyl-β-cyclodextrin (MβCD) is a common method to deplete cholesterol from the plasma membrane in cell culture experiments, which does result in inhibition of TLR4-mediated inflammatory responses[26,27]. Cyclodextrin derivatives are being developed as a promising therapy for the Niemann-Pick type C disease, a severe neurodegenerative lysosomal cholesterol storage disorder[28-31]. However, the physiologic mechanism of cholesterol removal from the cell involves the membrane and endosomal ATP-binding cassette (ABC) cholesterol transporters ABCA1 and ABCG1 and the extracellular cholesterol acceptors lipid-poor apoA-I and the HDL, whose major protein is apoA-I[32-34]. There is a substantial increase in inflammatory gene expression in response to TLR4 ligands in Abca1$^{-/-}$ Abcg1$^{-/-}$ cells, with less dramatic changes in cells lacking either ABCA1 or ABCG1[35,36]. The cholesterol acceptors HDL and lipid-poor apoA-I and a number of apoA-I mimetic peptides all reduce inflammatory responses as well[37-42]. Yet, the known mechanisms of cholesterol efflux do not imply any spatial or tissue selectivity, and the indiscriminate character of cellular cholesterol depletion by cyclodextrins or by apoA-I may limit their clinical applications. Our studies demonstrated that AIBP is a protein targeting cholesterol efflux specifically to TLR4-occupied lipid rafts for selective regulation of inflammatory responses.

Products of Manufacture, Kits

Also provided are products of manufacture such as implants or pumps, kits and pharmaceuticals for practicing the methods as provided herein. In alternative embodiments, provided are products of manufacture, kits and/or pharmaceuticals comprising all the components needed to practice a method as provided herein. In alternative embodiments, kits also comprise instructions for practicing a method as provided herein, Formulations and Pharmaceutical Compositions In alternative embodiments, provided are pharmaceutical formulations or compositions comprising nucleic acids and polypeptides for practicing methods and uses as provided herein to regulate neuropathic pain, the methods comprising upregulating the expression of ApoA-I Binding Protein (APOA1BP, AIBP, or AI-BP). In alternative embodiments, provided are pharmaceutical formulations or compositions for use in in vivo, in vitro or ex vivo methods to treat, prevent, reverse and/or ameliorate neuropathic pain. In alternative embodiments, pharmaceutical compositions and formulations used to practice methods and uses as provided herein comprise APOA1BP nucleic acids and polypeptides or result in an increase in expression or activity of APOA1BP nucleic acids and polypeptides are administered to an individual in need thereof in an amount sufficient to treat, prevent, reverse and/or ameliorate, e.g., a neuropathic pain, a neurodegenerative disease or condition, optionally a chronic or progressive neurodegenerative disease, optionally Alzheimer's disease or a Chronic Traumatic Encephalopathy (CTE) or a related tauopathy, a traumatic brain injury (TBI), a posttraumatic stress disorder, a traumatic war neurosis, or a post-traumatic stress syndrome (PTSS). In alternative embodiments, pharmaceutical compositions and formulations used to practice methods and uses as provided herein comprise APOA1BP nucleic acids and polypeptides or result in an increase in expression or activity of APOA1BP nucleic acids and polypeptides are administered to an individual in need thereof in an amount sufficient to prevent or decrease the intensity of and/or frequency of e.g., the neuropathic pain or neurodegenerative disease or condition.

In alternative embodiments, the pharmaceutical compositions used to practice methods and uses as provided herein can be administered parenterally, topically, orally or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration are well described in the scientific and patent literature, see, e.g., the latest edition of *Remington's Pharmaceutical Sciences*, Maack Publishing Co., Easton Pa. ("Remington's").

For example, in alternative embodiments, these compositions used to practice methods and uses as provided herein are formulated in a buffer, in a saline solution, in a powder, an emulsion, in a vesicle, in a liposome, in a nanoparticle, in a nanolipoparticle and the like. In alternative embodiments, the compositions can be formulated in any way and can be applied in a variety of concentrations and forms depending on the desired in vivo, in vitro or ex vivo conditions, a desired in vivo, in vitro or ex vivo method of administration and the like. Details on techniques for in vivo, in vitro or ex vivo formulations and administrations are well described in the scientific and patent literature. Formulations and/or carriers used to practice methods or uses as provided herein can be in forms such as tablets, pills, powders, capsules, liquids, gels, syrups, slurries, suspensions, etc., suitable for in vivo, in vitro or ex vivo applications.

In alternative embodiments, formulations and pharmaceutical compositions used to practice methods and uses as provided herein can comprise a solution of compositions (which include peptidomimetics, racemic mixtures or racemates, isomers, stereoisomers, derivatives and/or analogs of compounds) disposed in or dissolved in a pharmaceutically acceptable carrier, e.g., acceptable vehicles and solvents that can be employed include water and Ringer's solution, an isotonic sodium chloride. In addition, sterile fixed oils can be employed as a solvent or suspending medium. For this purpose any fixed oil can be employed including synthetic mono- or diglycerides, or fatty acids such as oleic acid. In one embodiment, solutions and formulations used to practice methods and uses as provided herein are sterile and can be manufactured to be generally free of undesirable matter. In one embodiment, these solutions and formulations are sterilized by conventional, well known sterilization techniques.

The solutions and formulations used to practice methods and uses as provided herein can comprise auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and can be selected primarily based on fluid volumes, viscosities and the like, in accordance with the particular mode of in vivo, in vitro or ex vivo administration selected and the desired results.

The compositions and formulations used to practice methods and uses as provided herein can be delivered by the use of liposomes. By using liposomes, particularly where the liposome surface carries ligands specific for target cells (e.g., an injured or diseased neuronal cell or CNS tissue), or are otherwise preferentially directed to a specific tissue or organ type, one can focus the delivery of the active agent into a target cells in an in vivo, in vitro or ex vivo application.

Nanoparticles, Nanolipoparticles and Liposomes

Also provided are nanoparticles, nanolipoparticles, vesicles and liposomal membranes comprising compounds used to practice methods and uses as provided herein, e.g., to deliver compositions comprising APOA1BP nucleic acids and polypeptides in vivo, e.g., to the CNS and brain. In alternative embodiments, these compositions are designed to target specific molecules, including biologic molecules, such as polypeptides, including cell surface polypeptides, e.g., for targeting a desired cell type or organ, e.g., a nerve cell or the CNS, and the like.

Provided are multilayered liposomes comprising compounds used to practice methods and uses as provided herein, e.g., as described in Park, et al., U.S. Pat. Pub. No. 20070082042. The multilayered liposomes can be prepared using a mixture of oil-phase components comprising squalane, sterols, ceramides, neutral lipids or oils, fatty acids and lecithins, to about 200 to 5000 nm in particle size, to entrap a composition used to practice methods and uses as provided herein.

Liposomes can be made using any method, e.g., as described in Park, et al., U.S. Pat. Pub. No. 20070042031, including method of producing a liposome by encapsulating an active agent (e.g., APOA1BP nucleic acids and polypeptides), the method comprising providing an aqueous solution in a first reservoir; providing an organic lipid solution in a second reservoir, and then mixing the aqueous solution with the organic lipid solution in a first mixing region to produce a liposome solution, where the organic lipid solution mixes with the aqueous solution to substantially instantaneously produce a liposome encapsulating the active agent; and immediately then mixing the liposome solution with a buffer solution to produce a diluted liposome solution.

In one embodiment, liposome compositions used to practice methods and uses as provided herein comprise a substituted ammonium and/or polyanions, e.g., for targeting delivery of a compound (e.g., a APOA1BP nucleic acid and polypeptide) to a desired cell type (e.g., an endothelial cell, a nerve cell, or any tissue or area, e.g., a CNS, in need thereof), as described e.g., in U.S. Pat. Pub. No. 20070110798.

Provided are nanoparticles comprising compounds (e.g., APOA1BP nucleic acids and polypeptides used to practice methods provided herein) in the form of active agent-containing nanoparticles (e.g., a secondary nanoparticle), as described, e.g., in U.S. Pat. Pub. No. 20070077286. In one embodiment, provided are nanoparticles comprising a fat-soluble active agent or a fat-solubilized water-soluble active agent to act with a bivalent or trivalent metal salt.

In one embodiment, solid lipid suspensions can be used to formulate and to deliver compositions used to practice methods and uses as provided herein to mammalian cells in vivo, e.g., to the CNS, as described, e.g., in U.S. Pat. Pub. No. 20050136121.

Delivery Vehicle Modifications and Modification of AIBP

In alternative embodiments, AIBP peptides or polypeptides, or AIBP-comprising nanoparticles, liposomes and the like (e.g., comprising or having contained therein APOA1BP nucleic acids or polypeptides used to practice methods provided herein) are modified to facilitate intrathecal injection, e.g., delivery into the cerebrospinal fluid or brain. For example, in alternative embodiments, AIBP peptides or polypeptides, or AIBP-comprising nanoparticles, liposomes and the like, are engineered to comprise a moiety that allows the AIBP peptides or polypeptides, or AIBP-comprising nanoparticles, liposomes and the like, to bind to a receptor or cell membrane structure that facilitates delivery into the CNS or brain, e.g., where the moiety can comprise a mannose-6-phosphate receptor, a melanotransferrin receptor, a LRP receptor or any other receptor that is ubiquitously expressed on the surface of any CNS or brain cell. For example, conjugation of mannose-6-phosphate moieties allows the AIBP peptides or polypeptides, or AIBP-comprising nanoparticles, liposomes and the like, to be taken up by a CNS cell that expresses a mannose-6-phosphate receptor. In alternative embodiments, any protocol or modification of the AIBP peptides or polypeptides, or AIBP-comprising nanoparticles, liposomes and the like, that facilitates entry or delivery into the CNS or brain in vivo can be used, e.g., as described in U.S. Pat. No. 9,089,566.

In alternative embodiments, AIBP peptides or polypeptides, or AIBP-comprising nanoparticles, liposomes and the like (e.g., comprising or having contained therein APOA1BP nucleic acids or polypeptides used to practice methods provided herein) are directly or indirectly linked or conjugated to any blood brain barrier (BBB)-targeting agent, for example, a transferrin, an insulin, a leptin, an insulin-like growth factor, a cationic peptide, a lectin, a Receptor-Associated Protein (RAP) (a 39 kD chaperone localized to the endoplasmic reticulum and Golgi, a lipoprotein receptor-related protein (LRP) receptor family ligand), an antibody (e.g., a peptidomimetic monoclonal antibody) to a transferrin receptor, an antibody (e.g., a peptidomimetic monoclonal antibody) to the insulin receptor, an antibody (e.g., a peptidomimetic monoclonal antibody) to the insulin-like growth factor receptor, an antibody (e.g., a peptidomimetic monoclonal antibody) to the leptin receptor and the like. In alternative embodiments, any protocol or modification of the AIBP peptides or polypeptides, or AIBP-comprising nanoparticles, liposomes and the like, that facilitates crossing of the BBB can be used, e.g., as described in US Pat App Pub nos. 20050142141; 20050042227. For example, to enhance CNS or brain delivery of an composition used to practice methods as provided herein, any protocol can be used, e.g.: direct intra-cranial injection, transient permeabilization of the BBB, and/or modification of AIBP peptides or polypeptides, or AIBP-comprising nanoparticles, liposomes and the like to alter tissue distribution Delivery Cells and Delivery Vehicles In alternative embodiments, any delivery vehicle can be used to practice the methods or uses as provided herein, e.g., to deliver compositions (e.g., APOA1BP nucleic acids and polypeptides) to a CNS or a brain in vivo. For example, delivery vehicles comprising polycations, cationic polymers and/or cationic peptides, such as polyethyleneimine derivatives, can be used e.g. as described, e.g., in U.S. Pat. Pub. No. 20060083737. In one embodiment, a delivery vehicle is a transduced cell engineered to express or overexpress and then secrete an endogenous or exogenous AIBP.

In one embodiment, a dried polypeptide-surfactant complex is used to formulate a composition used to practice methods as provided herein, e.g. as described, e.g., in U.S. Pat. Pub. No. 20040151766.

In one embodiment, a composition used to practice methods and uses as provided herein can be applied to cells using vehicles with cell membrane-permeant peptide conjugates, e.g., as described in U.S. Pat. Nos. 7,306,783; 6,589,503. In one aspect, the composition to be delivered is conjugated to a cell membrane-permeant peptide. In one embodiment, the composition to be delivered and/or the delivery vehicle are conjugated to a transport-mediating peptide, e.g., as described in U.S. Pat. No. 5,846,743, describing transport-mediating peptides that are highly basic and bind to polyphosphoinositides.

In one embodiment, cells that will be subsequently delivered to a CNS or a brain are transfected or transduced with an AIBP-expressing nucleic acid, e.g., a vector, e.g., by electro-permeabilization, which can be used as a primary or adjunctive means to deliver the composition to a cell, e.g., using any electroporation system as described e.g. in U.S. Pat. Nos. 7,109,034; 6,261,815; 5,874,268.

In Vivo Delivery of AIBP-Encoding Nucleic

In alternative embodiments, provided are compositions and methods for delivering nucleic acids encoding AIBP peptides or polypeptides, or nucleic acids encoding peptides or polypeptides having AIBP activity, or vectors or recombinant viruses having contained therein these nucleic acids. In alternative embodiments, the nucleic acids, vectors or recombinant viruses are designed for in vivo or CNS delivery and expression.

In alternative embodiments, provided are compositions and methods for the delivery and controlled expression of an AIBP-encoding nucleic acid or gene, or an expression vehicle (e.g., vector, recombinant virus, and the like) comprising (having contained therein) an AIBP encoding nucleic acid or gene, that results in an AIBP protein being released into the bloodstream or general circulation where it can have a beneficial effect on in the body, e.g., such as the CNS, brain or other targets.

In alternative embodiments, the provided are methods for being able to turn on and turn off AIBP-expressing nucleic acid or gene expression easily and efficiently for tailored treatments and insurance of optimal safety.

In alternative embodiments, AIBP protein or proteins expressed by the AIBP-expressing nucleic acid(s) or gene(s) have a beneficial or favorable effects (e.g., therapeutic or prophylactic) on a tissue or an organ, e.g., the brain, CNS, or other targets, even though secreted into the blood or general circulation at a distance (e.g., anatomically remote) from their site or sites of action.

In alternative embodiments, provided are expression vehicles, vectors, recombinant viruses and the like for in vivo expression of an AIBP-encoding nucleic acid or gene to practice the methods as provide herein. In alternative embodiments, the expression vehicles, vectors, recombinant viruses and the like expressing the an AIBP nucleic acid or gene can be delivered by intramuscular (IM) injection, by intravenous (IV) injection, by subcutaneous injection, by inhalation, by a biolistic particle delivery system (e.g., a so-called "gene gun"), and the like, e.g., as an outpatient, e.g., during an office visit.

In alternative embodiments, this "peripheral" mode of delivery, e.g., expression vehicles, vectors, recombinant viruses and the like injected IM or IV, can circumvent problems encountered when genes or nucleic acids are expressed directly in an organ (e.g., the brain or CNS) itself. Sustained secretion of an AIBP in the bloodstream or general circulation also circumvents the difficulties and expense of administering proteins by infusion.

In alternative embodiments a recombinant virus (e.g., a long-term virus or viral vector), or a vector, or an expression vector, and the like, can be injected, e.g., in a systemic vein (e.g., IV), or by intramuscular (IM) injection, by inhalation, or by a biolistic particle delivery system (e.g., a so-called "gene gun"), e.g., as an outpatient, e.g., in a physician's office. In alternative embodiments, days or weeks later (e.g., four weeks later), the individual, patient or subject is administered (e.g., inhales, is injected or swallows), a chemical or pharmaceutical that induces expression of the AIBP-expressing nucleic acids or genes; for example, an oral antibiotic (e.g., doxycycline or rapamycin) is administered once daily (or more or less often), which will activate the expression of the gene. In alternative embodiments, after the "activation", or inducement of expression (e.g., by an inducible promoter) of the nucleic acid or gene, an AIBP protein is synthesized and released into the subject's circulation (e.g., into the blood), and subsequently has favorable physiological effects, e.g., therapeutic or prophylactic, that benefit the individual or patient (e.g., benefit heart, kidney or lung function). When the physician or subject desires discontinuation of the AIBP treatment, the subject simply stops taking the activating chemical or pharmaceutical, e.g., antibiotic. Alternative embodiments comprise use of "expression cassettes" comprising or having contained therein a nucleotide sequence used to practice methods provided herein, e.g., an AIBP-expressing nucleic acid, which can be capable of affecting expression of the nucleic acid, e.g., as a structural gene or a transcript (e.g., encoding an AIBP protein) in a host compatible with such sequences. Expression cassettes can include at least a promoter operably linked with the polypeptide coding sequence or inhibitory sequence; and, in one aspect, with other sequences, e.g., transcription termination signals. Additional factors necessary or helpful in effecting expression may also be used, e.g., enhancers.

In alternative aspects, expression cassettes also include plasmids, expression vectors, recombinant viruses, any form of recombinant "naked DNA" vector, and the like. In alternative aspects, a "vector" can comprise a nucleic acid that can infect, transfect, transiently or permanently transduce a cell. In alternative aspects, a vector can be a naked nucleic acid, or a nucleic acid complexed with protein or lipid. In alternative aspects, vectors can comprise viral or bacterial nucleic acids and/or proteins, and/or membranes (e.g., a cell membrane, a viral lipid envelope, etc.). In alternative aspects, vectors can include, but are not limited to replicons (e.g., RNA replicons, bacteriophages) to which fragments of DNA may be attached and become replicated. Vectors thus include, but are not limited to RNA, autonomous self-replicating circular or linear DNA or RNA (e.g., plasmids, viruses, and the like, see, e.g., U.S. Pat. No. 5,217,879), and can include both the expression and non-expression plasmids. In alternative aspects, a vector can be stably replicated by the cells during mitosis as an autonomous structure, or can be incorporated within the host's genome.

In alternative aspects, "promoters" include all sequences capable of driving transcription of a coding sequence in a cell, e.g., a mammalian cell such as a muscle, nerve or brain cell. Promoters used in the constructs provided herein include cis-acting transcriptional control elements and regulatory sequences that are involved in regulating or modulating the timing and/or rate of transcription of a nucleic acid, e.g., an AIBP-encoding nucleic acid. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) transcription.

In alternative embodiments, "constitutive" promoters can be those that drive expression continuously under most environmental conditions and states of development or cell differentiation. In alternative embodiments, "inducible" or "regulatable" promoters can direct expression of a nucleic acid, e.g., an AIBP-encoding nucleic acid, under the influence of environmental conditions, administered chemical agents, or developmental conditions.

Gene Therapy and Gene Delivery Vehicles

In alternative embodiments, methods of the invention comprise use of nucleic acid (e.g., gene or polypeptide encoding an AIBP-encoding nucleic acid) delivery systems to deliver a payload of the nucleic acid or gene, or AIBP-expressing nucleic acid, transcript or message, to a cell or cells in vitro, ex vivo, or in vivo, e.g., as gene therapy delivery vehicles.

In alternative embodiments, expression vehicle, vector, recombinant virus, or equivalents used to practice methods provided herein are or comprise: an adeno-associated virus (AAV), a lentiviral vector or an adenovirus vector; an AAV serotype AAV5, AAV6, AAV8 or AAV9; a rhesus-derived AAV, or the rhesus-derived AAV AAVrh. 10hCLN2; an organ-tropic AAV, or a neurotropic AAV; and/or an AAV capsid mutant or AAV hybrid serotype. In alternative embodiments, the AAV is engineered to increase efficiency in targeting a specific cell type that is non-permissive to a wild type (wt) AAV and/or to improve efficacy in infecting only a cell type of interest. In alternative embodiments, the hybrid AAV is retargeted or engineered as a hybrid serotype by one or more modifications comprising: 1) a transcapsidation, 2) adsorption of a bi-specific antibody to a capsid surface, 3) engineering a mosaic capsid, and/or 4) engineering a chimeric capsid. It is well known in the art how to engineer an adeno-associated virus (AAV) capsid in order to increase efficiency in targeting specific cell types that are non-permissive to wild type (wt) viruses and to improve efficacy in infecting only the cell type of interest; see e.g., Wu et al., Mol. Ther. 2006 September; 14(3):316-27. Epub 2006 July 7; Choi, et al., Curr. Gene Ther. 2005 June; 5(3):299-310.

For example, in alternative embodiments, serotypes AAV-8, AAV-9, AAV-DJ or AAV-DJ/8™ (Cell Biolabs, Inc., San Diego, Calif.), which have increased uptake in brain tissue in vivo, are used to deliver an AIBP-encoding nucleic acid payload for expression in the CNS. In alternative embodiments, the following serotypes, or variants thereof, are used for targeting a specific tissue:

| Tissue | Optimal Serotype |
| --- | --- |
| CNS | AAV1, AAV2, AAV4, AAV5, AAV8, AAV9 |
| Heart | AAV1, AAV8, AAV9 |
| Kidney | AAV2 |
| Liver | AAV7, AAV8, AAV9 |
| Lung | AAV4, AAV5, AAV6, AAV9 |
| Pancreas | AAV8 |

| Tissue | Optimal Serotype |
| --- | --- |
| Photoreceptor Cells | AAV2, AAV5, AAV8 |
| RPE (Retinal Pigment Epithelium) | AAV1, AAV2, AAV4, AAV5, AAV8 |
| Skeletal Muscle | AAV1, AAV6, AAV7, AAV8, AAV9 |

In alternative embodiments, the rhesus-derived AAV AAVrh. 10hCLN2 or equivalents thereof can be used, wherein the rhesus-derived AAV may not be inhibited by any pre-existing immunity in a human; see e.g., Sondhi, et al., Hum Gene Ther. Methods. 2012 October; 23(5):324-35, Epub 2012 Nov. 6; Sondhi, et al., Hum Gene Ther. Methods. 2012 Oct. 17; teaching that direct administration of AAVrh. 10hCLN2 to the CNS of rats and non-human primates at doses scalable to humans has an acceptable safety profile and mediates significant payload expression in the CNS.

Because adeno-associated viruses (AAVs) are common infective agents of primates, and as such, healthy primates carry a large pool of AAV-specific neutralizing antibodies (NAbs) which inhibit AAV-mediated gene transfer therapeutic strategies, methods provided herein can comprise screening of patient candidates for AAV-specific NAbs prior to treatment, especially with the frequently used AAV8 capsid component, to facilitate individualized treatment design and enhance therapeutic efficacy; see, e.g., Sun, et al., J. Immunol. Methods. 2013 Jan. 31; 387(1-2):114-20, Epub 2012 Oct. 11.

Dosaging

The pharmaceutical compositions and formulations used to practice methods and uses as provided herein can be administered for prophylactic and/or therapeutic treatments. In therapeutic applications, compositions are administered to a subject already suffering from a disease, condition, infection or defect in an amount sufficient to cure, alleviate or partially arrest the clinical manifestations of the disease, condition, infection or disease and its complications (a "therapeutically effective amount"), including e.g., a neuropathic pain. For example, in alternative embodiments, APOA1BP nucleic acid- or polypeptide-comprising pharmaceutical compositions and formulations as provided herein are administered to an individual in need thereof in an amount sufficient to treat, prevent, reverse and/or ameliorate a neuropathic pain, an inflammation-induced neuropathic pain, an inflammation-induced neuropathic pain, a nerve or CNS inflammation, a allodynia, a post nerve injury pain or neuropathic pain, a post-surgical pain or neuropathic pain, a chemotherapeutic-induced peripheral neuropathy (CIPN) (e.g., cisplatin-induced allodynia), a neurodegenerative disease or condition, optionally a chronic or progressive neurodegenerative disease or condition, optionally Alzheimer's disease or a Chronic Traumatic Encephalopathy (CTE) or a related tauopathy, a traumatic brain injury (TBI), a posttraumatic stress disorder, a traumatic war neurosis, or a post-traumatic stress syndrome (PTSS), a migraine, and/or a hyperalgesia.

The amount of pharmaceutical composition adequate to accomplish this is defined as a "therapeutically effective dose." The dosage schedule and amounts effective for this use, i.e., the "dosing regimen," will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

In alternative embodiments, viral vectors such as adenovirus or AAV vectors are administered to an individual in need therein, and in alternative embodiment the dosage administered to a human comprises: a dose of about $2 \times 10^{12}$ vector genomes per kg body weight (vg/kg), or between about $10^{10}$ and $10^{14}$ vector genomes per kg body weight (vg/kg), or about $10^9$, $10^{10}$, $10^{11}$, $10^{12}$, $10^{13}$, $10^{14}$, $10^{15}$, or more vg/kg, which can be administered as a single dosage or in multiple dosages, as needed. In alternative embodiments, these dosages are administered orally, IM, IV, or intrathecally. In alternative embodiments, the vectors are delivered as formulations or pharmaceutical preparations, e.g., where the vectors are contained in a nanoparticle, a particle, a micelle or a liposome or lipoplex, a polymersome, a polyplex or a dendrimer. In alternative embodiments, these dosages are administered once a day, once a week, or any variation thereof as needed to maintain in vivo expression levels of AIBP, which can be monitored by measuring actually expression of AIBP or by monitoring of therapeutic effect, e.g., diminishing of pain. The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; the latest Remington's, supra). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods as provided herein are correct and appropriate.

Single or multiple administrations of formulations can be given depending on the dosage and frequency as required and tolerated by the patient. The formulations should provide a sufficient quantity of active agent to effectively treat, prevent or ameliorate a conditions, diseases or symptoms as described herein. For example, alternative exemplary pharmaceutical formulations for oral administration of compositions used to practice methods as provided herein are in a daily amount of between about 0.1 to 0.5 to about 20, 50, 100 or 1000 or more ug per kilogram of body weight per day. In an alternative embodiment, dosages are from about 1 mg to about 4 mg per kg of body weight per patient per day are used. Lower dosages can be used, in contrast to administration orally, into the blood stream, into a body cavity or into a lumen of an organ. Substantially higher dosages can be used in topical or oral administration or administering by powders, spray or inhalation. Actual methods for preparing parenterally or non-parenterally administrable formulations will be known or apparent to those skilled in the art and are described in more detail in such publications as Remington's, supra.

The methods as provided herein can further comprise co-administration with other drugs or pharmaceuticals, e.g., compositions for treating any neurological or neuromuscular disease, condition, infection or injury, including related inflammatory and autoimmune diseases and conditions, and the like. For example, the methods and/or compositions and formulations as provided herein can be co-formulated with and/or co-administered with, fluids, antibiotics, cytokines, immunoregulatory agents, anti-inflammatory agents, pain alleviating compounds, complement activating agents, such as peptides or proteins comprising collagen-like domains or fibrinogen-like domains (e.g., a ficolin), carbohydrate-binding domains, and the like and combinations thereof Bioisosteres of Compounds In alternative embodiment, also provided are bioisosteres of compounds used to practice the methods provided herein, e.g., polypeptides having a APOA1BP activity. Bioisosteres used to practice methods as provided herein include bioisosteres of, e.g., APOA1BP nucleic acids and polypeptides, which in alternative embodiments can comprise one or more substituent and/or group replacements with a substituent and/or group having substantially similar physical or chemical properties which produce substantially similar biological properties to compounds used to practice methods or uses as provided herein. In one embodiment, the purpose of exchanging one bioisostere for another is to enhance the desired biological or physical properties of a compound without making significant changes in chemical structures.

For example, in one embodiment, one or more hydrogen atom(s) is replaced with one or more fluorine atom(s), e.g., at a site of metabolic oxidation; this may prevent metabolism (catabolism) from taking place. Because the fluorine atom is similar in size to the hydrogen atom the overall topology of the molecule is not significantly affected, leaving the desired biological activity unaffected. However, with a blocked pathway for metabolism, the molecule may have a longer half-life or be less toxic, and the like.

Devices for Delivering Therapeutic Agents Directly into the CNS or Brain

In alternative embodiments, pharmaceutical compositions and formulations, including nanoparticles and liposomes, used to practice methods as provided herein are delivered directly into a CNS or a brain, e.g., either by injection intravenously or intrathecally, or by various devices known in the art. For example, U.S. Pat. App. Pub. No. 20080140056, describes a rostrally advancing catheter in the intrathecal space for direct brain delivery of pharmaceuticals and formulations. Implantable infusion devices can also be used; e.g., a catheter to deliver fluid from the infusion device to the brain can be tunneled subcutaneously from the abdomen to the patient's skull, where the catheter can gain access to the individual's brain via a drilled hole. Alternatively, a catheter may be implanted such that it delivers the agent intrathecally within the patient's spinal canal. Flexible guide catheters having a distal end for introduction beneath the skull of a patient and a proximal end remaining external of the patient also can be used, e.g., see U.S. Pat. App. Pub. No. 20060129126.

In alternative embodiments, pharmaceutical compositions and formulations used to practice methods as provided herein are delivered via direct delivery of pharmaceutical compositions and formulations, including nanoparticles and liposomes, or direct implantation of cells that express AIBP into a brain, for example, using any cell implantation cannula, syringe and the like, as described e.g., in U.S. Pat. App. Pub. No. 20080132878; or elongate medical insertion devices as described e.g., in U.S. Pat. No. 7,343,205; or a surgical cannula as described e.g., in U.S. Pat. No. 4,899,729. Implantation cannulas, syringes and the like also can be used for direct injection of liquids, e.g., as fluid suspensions.

In alternative embodiments, pharmaceutical compositions and formulations used to practice methods as provided herein are delivered with tracers that are detectable, for example, by magnetic resonance imaging (MRI) and/or by X-ray computed tomography (CT); the tracers can be co-infused with the therapeutic agent and used to monitor the distribution of the therapeutic agent as it moves through the target tissue, as described e.g., in U.S. Pat. No. 7,371,225.

Kits and Instructions

Provided are kits comprising compositions (including the devices as described herein) and/or instructions for practicing methods as provided herein to e.g., treat, ameliorate or prevent a neuropathic pain. As such, kits, cells, vectors and the like can also be provided. In alternative embodiments, provided are kits comprising: a composition used to practice a method as provided herein, or a composition, a pharmaceutical composition or a formulation as provided herein, and optionally comprising instructions for use thereof.

The invention will be further described with reference to the examples described herein; however, it is to be understood that the invention is not limited to such examples.

EXAMPLES

Example 1: Efficacy Demonstrated in Exemplary Methods

This example describes and demonstrates exemplary embodiments, and the efficacy of methods as provided herein to e.g., treat or ameliorate a neuropathic pain, including e.g., allodynia and TLR4-mediated inflammation-induced neuropathic pain.

Role of TLR4 in Nociceptive Processing.

Figure 2:
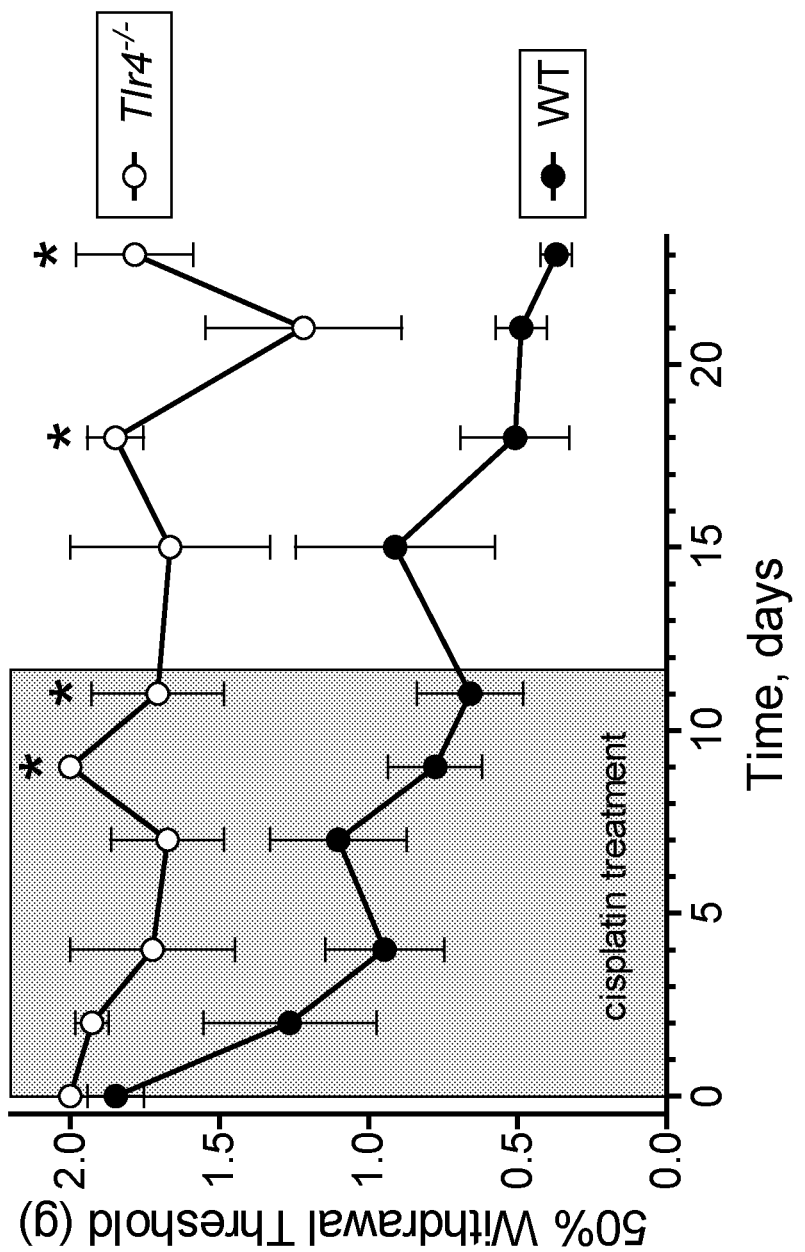
FIG. 2 graphically illustrates data showing the role of TLR4 in nociceptive processing. WT (n=7) and Tlr4$^{-/-}$ (n=4) mice were treated with six i.p. injections of cisplatin (2.3 mg/kg) over a period of 11 days (shaded box) and von Frey tested for allodynia. Mean±SEM; *, p<0.05, as discussed in detail in Example 1, below.

TLR4 serves as a pervasive mediator of persistent pain states. FIG. 2 shows that TLR4 deficiency results in a complete attenuation of tactile allodynia after treatment with the chemotherapeutic cisplatin[20]. Both the initial development of allodynia, during cisplatin treatment, and the persistent pain state are attenuated. We have shown that TLR4-mediated release of TNFα is considered to be an important factor in the development of allodynia[16,59,60].

TLR4 localizes to lipid rafts, and the factors that facilitate cholesterol depletion from lipid rafts have been shown to diminish TLR4-mediated inflammatory responses[20,61-64]. Below we describe a novel player in regulation of lipid rafts, AIBP, which we demonstrate can modulate (attenuate) TLR4-mediated allodynia and hyperalgesia.

AIBP Augments Cholesterol Efflux, Reduces Lipid Rafts and Interferes with Receptor Signaling.

Figure 3:
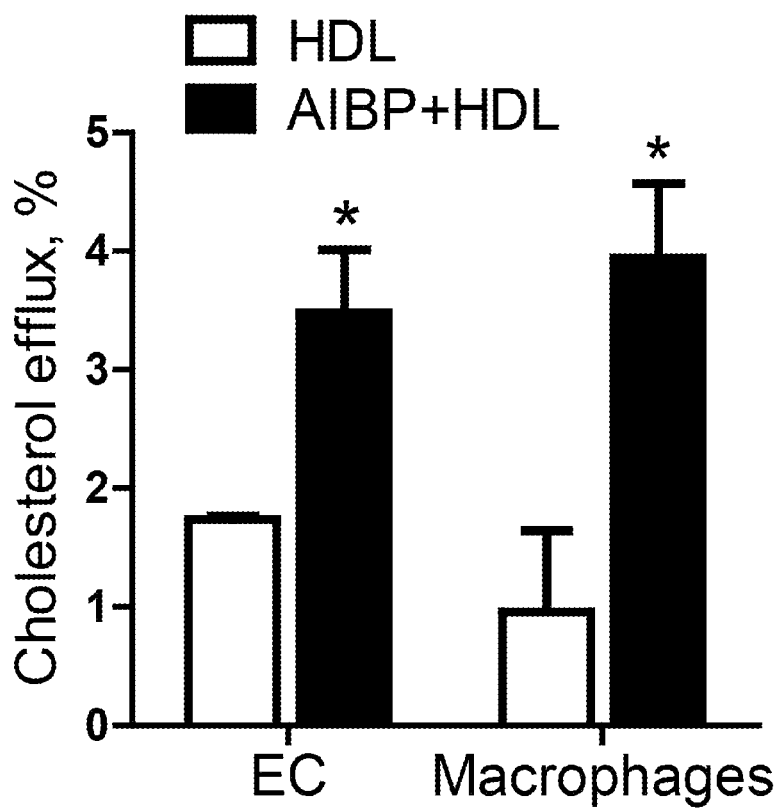
FIG. 3 graphically illustrates data showing that AIBP augments cholesterol efflux from endothelial cells (EC) and macrophages. Mean±SEM; n=4-7; *, p<0.05, as discussed in detail in Example 1, below
Figure 4A:
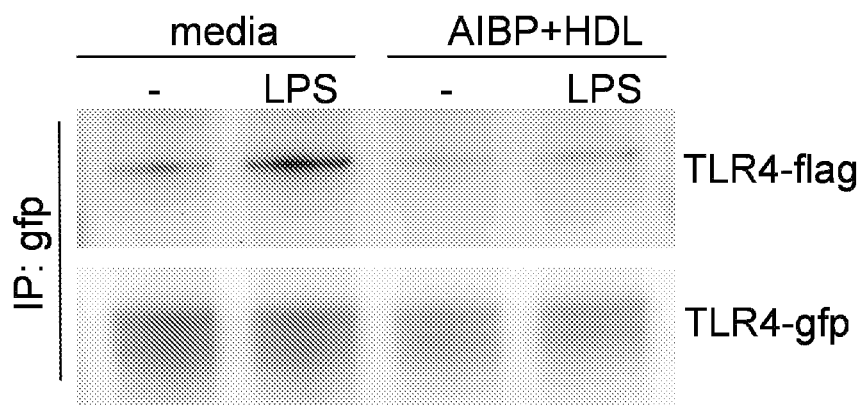
FIG. 4A, FIG. 4B and FIG. 4C illustrate images of gels, and FIG. 4D graphically illustrates data, showing that: AIBP/HDL$_3$ inhibit LPS-induced TLR4 dimerization FIG. 4(A); inflammatory signaling in macrophages in response to LPS FIG. 4(B); TLR4 and NOX4 localization to lipid rafts FIG. 4(C); and, ROS generation FIG. 4(D); in endothelial cells, as discussed in detail in Example 1, below.
Figure 4B:
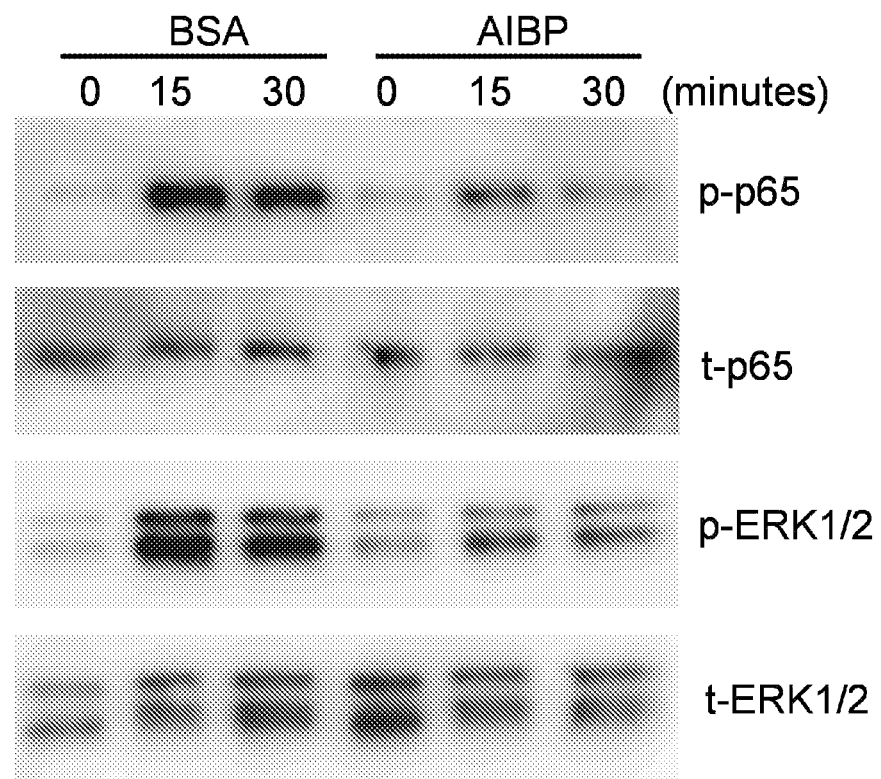
Figure 4C:
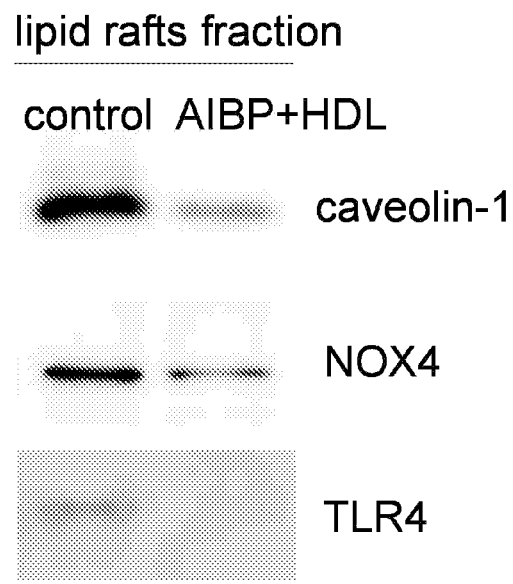
Figure 4D:
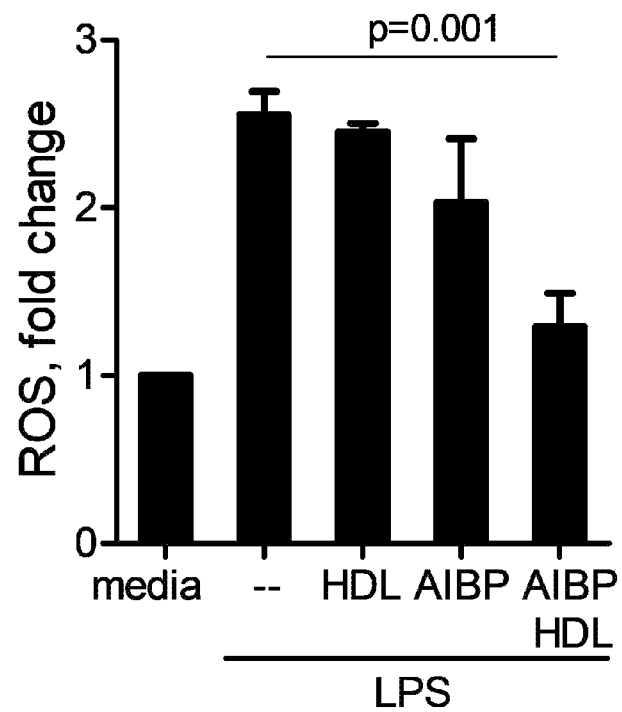

Since AIBP binds apoA-I[53], first we validated that recombinant AIBP bound $HDL_3$, a major HDL fraction involved in cholesterol efflux[58]. Then, we demonstrated that in the presence of AIBP, cholesterol efflux from endothelial cells (EC) and from macrophages to $HDL_3$ was increased 2-4 fold (FIG. 3). By itself, AIBP did not promote cholesterol efflux in the absence of $HDL_3$. Rather, AIBP binding to cells increased the overall capacity of the cell to bind $HDL_3$ and increased the rate of $HDL_3$ dissociation from cells[58], thereby creating conditions that would facilitate cholesterol efflux.

HDL removes cholesterol and reduces lipid rafts, a process which interferes with ligand-induced TLR4 dimerization. This hypothesis received initial validation in the experiments shown in FIG. 4: AIBP/$HDL_3$ treatment inhibited LPS-induced TLR4 dimerization in BaF3 cells expressing TLR4-flag and TLR4-gfp (A), LPS-induced phosphorylation of p65 and ERK1/2 in RAW macrophages (B), and localization of TLR4 and NOX4 to lipid rafts in EC (C), with a subsequent reduction in LPS-induced ROS (D).

Figure 5:
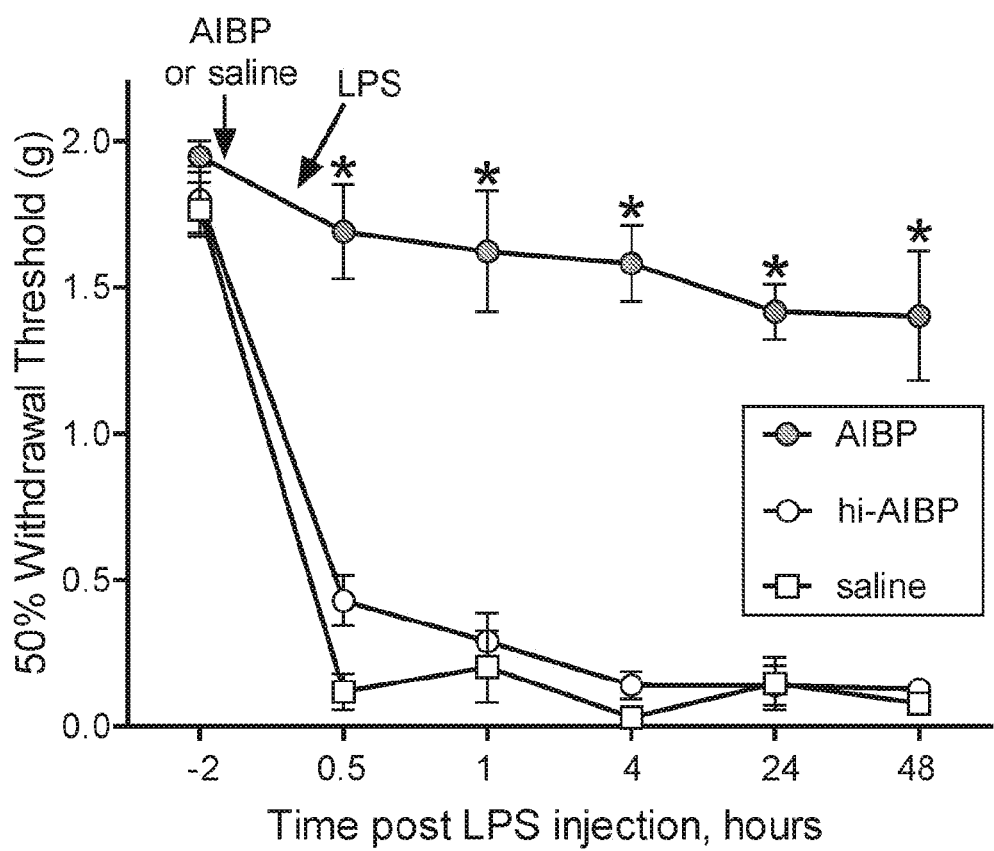
FIG. 5 graphically illustrates data showing that intrathecal (i.t.) administration of recombinant AIBP prevents LPS-induced tactile allodynia. Following baseline von Frey threshold testing, mice were given an i.t. injection of AIBP (0.5 µg/5 µl), heat-inactivated hi-AIBP (0.5 µg/5 µl), or saline (5 µl). Two hours later, all mice were given an i.t. injection of LPS (0.1 µg/5 µl). Mean±SEM; n=4; *, p<0.05, as discussed in detail in Example 1, below.
Figure 6:
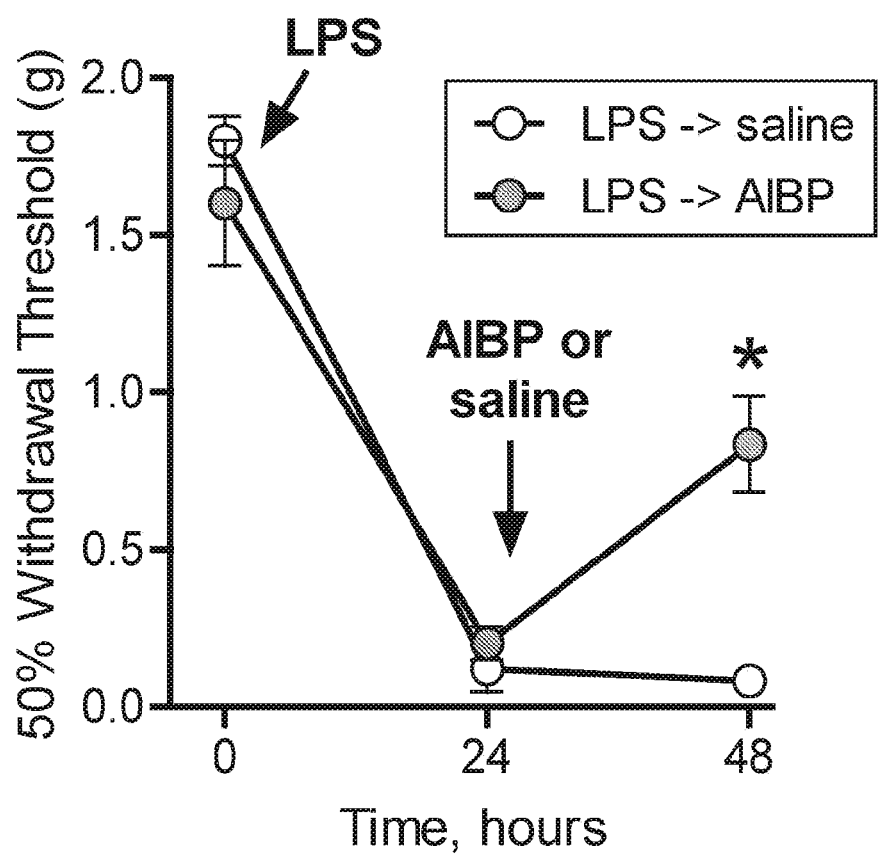
FIG. 6 graphically illustrates data showing that intrathecal administration of recombinant AIBP alleviates pre-existing allodynia. Following baseline von Frey threshold testing, animals were given an i.t. LPS (0.1 µg/5 µl). Twenty-four hours later, mice received i.t. AIBP (0.5 µg/5 µl) or saline (5 µl). Mean±SEM; n=4 per group; *, p<0.05, as discussed in detail in Example 1, below.

To test the hypothesis that AIBP inhibits TLR4-mediated inflammatory mechanisms of neuropathic pain, we injected saline or recombinant AIBP intrathecally (i.t.) 2 hours prior to the i.t. injection of LPS, the specific TLR4 agonist (FIG. 5). As expected from our previous studies, in the saline-injected group, LPS induced severe tactile allodynia. Remarkably, the AIBP injection entirely prevented LPS-induced allodynia, whereas injections of denatured, heat-inactivated AIBP did not have any effect. We did not observe any apparent toxicity of i.t. (or i.v. in other experiments) AIBP. These initial results provide strong support to our hypothesis. Importantly, i.t. AIBP injected up to 24 hours after i.t. LPS also reduced allodynia (FIG. 6).

Intraplantar Formalin-Evoked Delayed Tactile Allodynia.

Figure 7:
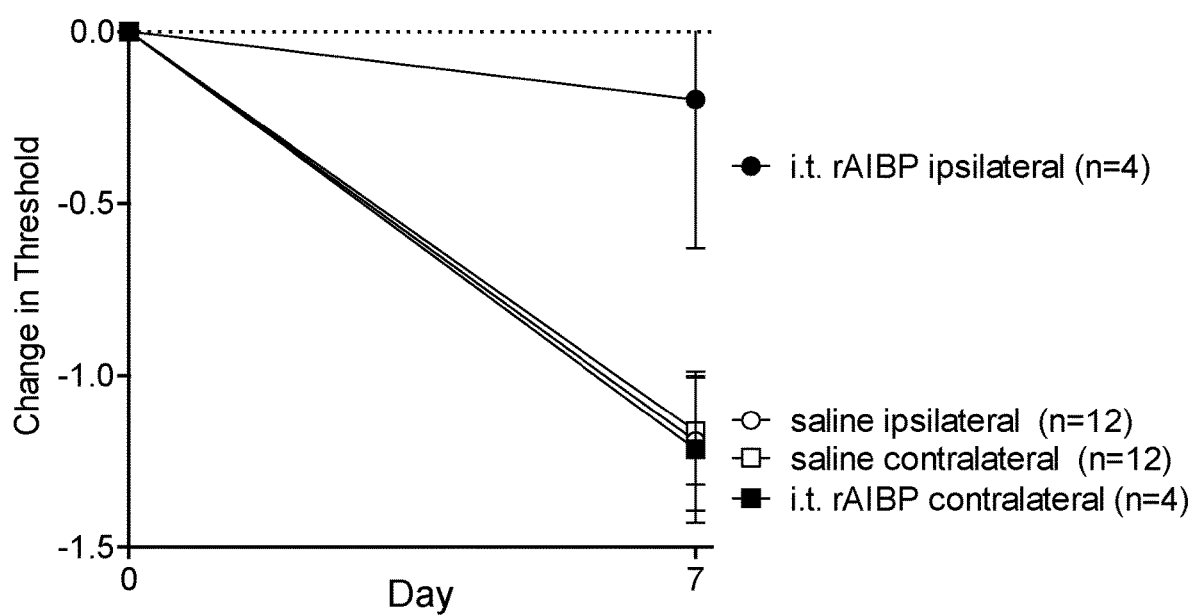
FIG. 7 graphically illustrates data showing that intrathecal administration of recombinant AIBP prevents intraplantar formalin-evoked delayed tactile allodynia. Following baseline von Frey threshold testing, mice were given an i.t. injection of AIBP (0.5 µg/5 µl) or saline (5 µl). Two hours later, all mice were given an injection of formalin into one paw, as discussed in detail in Example 1, below.

Intraplantar injection of formalin yields acute flinching behavior and, after 7 days, a persistent tactile allodynia and associated spinal microglial activation[65]. In recent work, we found that TLR4 knockout or antagonism had no effect on flinching, but prevented delayed tactile allodynia. Similarly, i.t. injections of AIBP prevented ipsilateral but not contralateral paw delayed tactile allodynia in response to formalin (FIG. 7).

Cisplatin-Induced Polyneuropathy.

Figure 8:
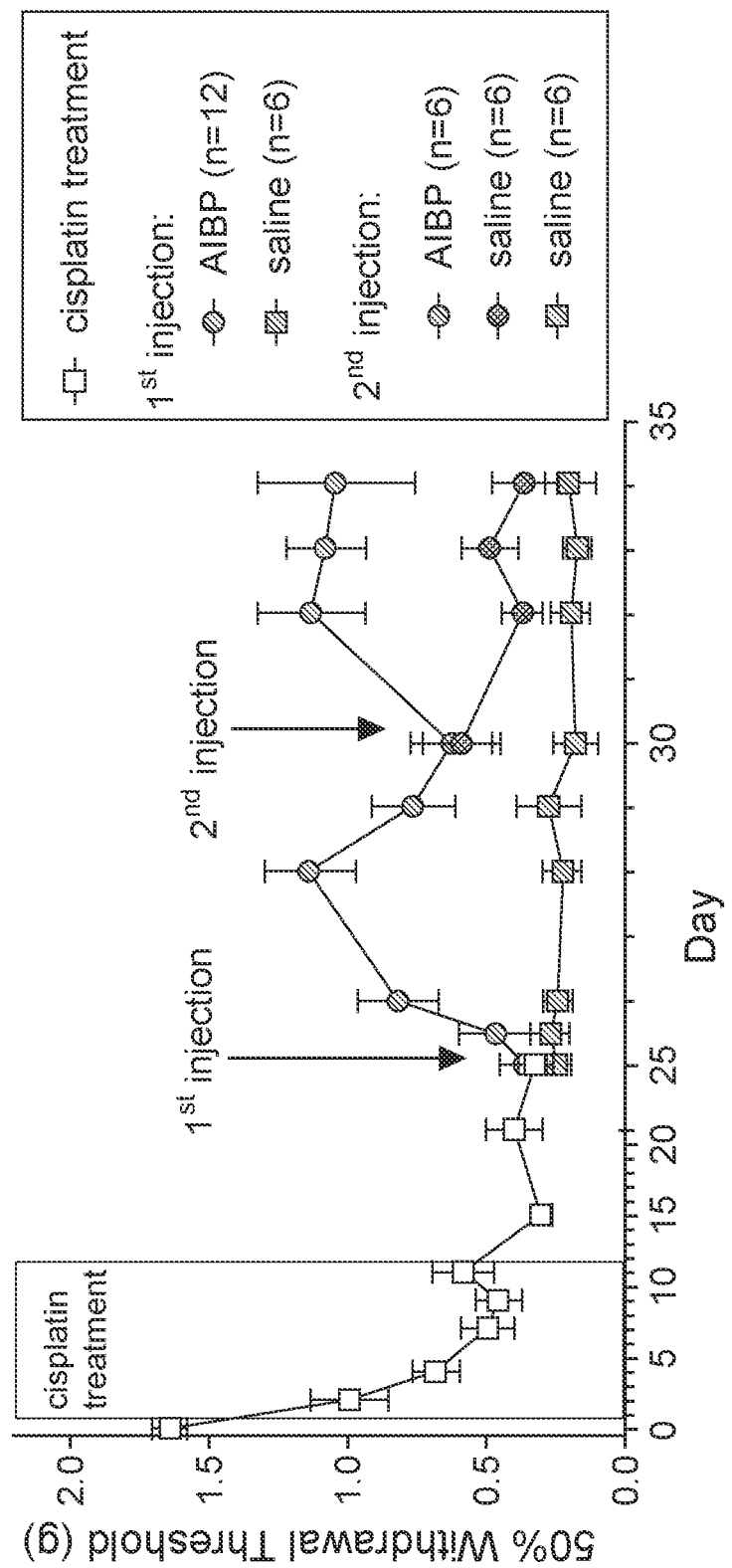
FIG. 8 graphically illustrates data showing that intrathecal administration of recombinant AIBP reduces cisplatin-induced tactile allodynia. Mice (n=18) received 6 i.p. injections of cisplatin (2.3 mg/kg) over a period of 11 days (gray shaded box). This treatment results in a progressive and persistent decrease in tactile threshold. On day 25, twelve mice were given i.t. AIBP (0.5 µg/5 µl; red circles on the graph) and 6 mice i.t. saline (grey squares). On day 30, the mice were given 2$^{nd}$ i.t. injection: 1) the mice that received saline were injected again with saline (grey squares); 2) six mice that received AIBP were injected again with AIBP (red circles); and 3) six mice that received AIBP were injected with saline (black circles). y were given a second i.t. injection of AIBP (n=6) or saline (n=6). Mean±SEM. *, p<0.05, as discussed in detail in Example 1, below.

In rodents, as people, cisplatin induces long-lasting tactile allodynia. This highly translational model showed that cisplatin-induced tactile allodynia is attenuated in Tlr4$^{-/-}$ mice[20,21]. We found that a single i.t. AIBP injection significantly, although transiently (days), reversed established cisplatin-induced allodynia (FIG. 8), while a second injection produced longer efficacy.

Clinically, chemotherapeutic-induced peripheral neuropathy (CIPN) is one of the only neuropathic pain states in which the initiation of the painful stimulus is predictably controlled. Therefore, we examined whether i.t. AIBP can prevent, as well as reverse, cisplatin-induced tactile allodynia in mice. Data graphically illustrated in FIG. 8, a single dose of AIBP may not be adequate; but as shown in the K/BxN model, 3 i.t. injections of a TLR4 antagonist were necessary to promote reversal of the delayed, persistent allodynia[16]. We note that multiple i.t. dosing can be performed in mice.

Figure 9:
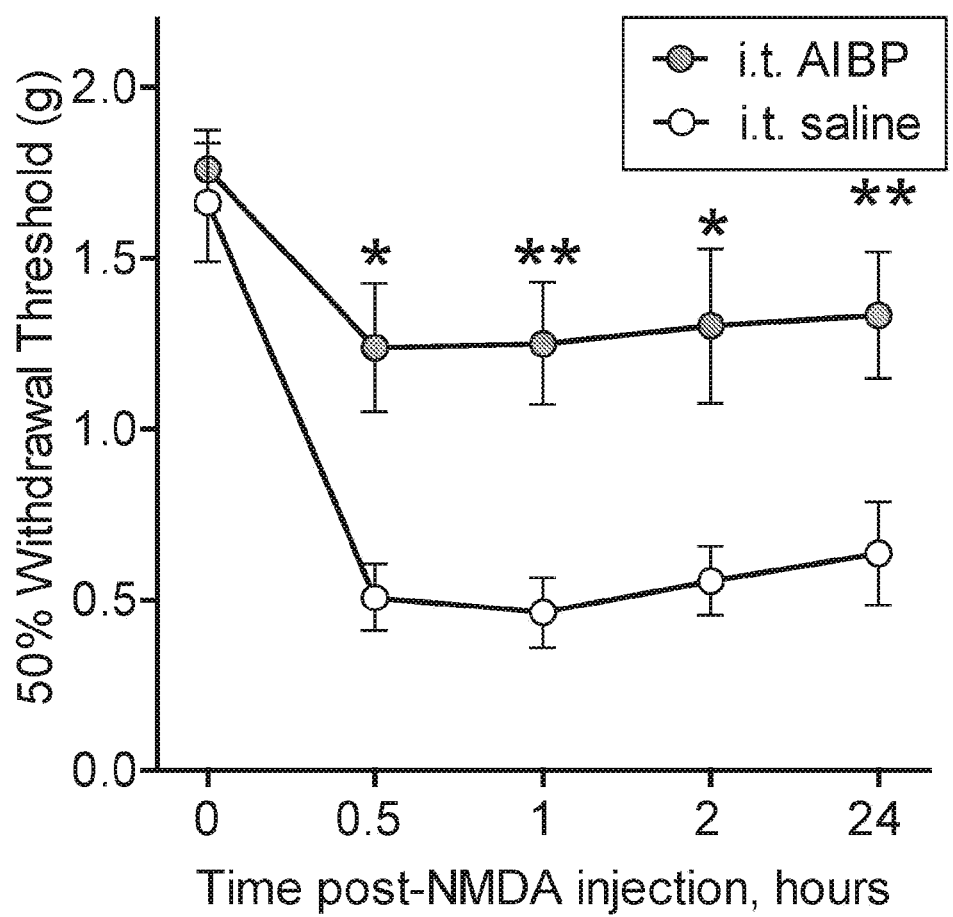
FIG. 9 graphically illustrates data showing that AIBP i.t. injection and TLR4 deficiency protect against NMDA (N-Methyl-D-aspartic acid or N-Methyl-D-aspartate)-induced allodynia. Two hours after WT mice received i.t. AIBP (0.5 µg/5 µl; n=8) or no injection (n=8), they received i.t. NMDA (0.25 nM). Mean±SEM; *, p<0.05; **, p<0.005, as discussed in detail in Example 1, below.

While the invention is not limited by any particular mechanism of action, AIBP may affect not only TLR4 but also the function of other receptors localized to lipid rafts. We injected mice i.t. with AIBP, followed by i.t. NMDA. Remarkably, the AIBP injection in large part prevented NMDA-induced allodynia (FIG. 9).

Example 2: Efficacy Demonstrated in Exemplary Methods—AIBP Treats and Prevents Neuropathic Pain This example describes and demonstrates exemplary embodiments, and the efficacy of methods as provided herein to e.g., treat or ameliorate a neuropathic pain, including e.g., allodynia and TLR4-mediated inflammation-induced neuropathic pain.

In alternative embodiments, provided are methods for treating, ameliorating, preventing, reversing or decreasing the severity or duration of nerve and tissue injury and related neuropathic pain states generated by e.g., trauma, chemotherapy, arthritis, diabetes, or viral infection, all of which can result in neuropathic pain states.

A common feature of these initiating events is the release of damage-associated molecular pattern molecules, which can activate Toll-like receptors (TLRs) (1-4). Neuraxial TLR4 and its downstream signaling adaptors have been implicated in the development of facilitated pain states, such as occurs after nerve injury (5-11) and particularly in the evolution of a chronic pain state after an acute injury or inflammation (6). As several other key inflammatory and neurotransmitter receptors, activated TLR4 localizes to lipid rafts (12-15). We found that AIBP, in combination with high-density lipoprotein (HDL), reduces lipid rafts in endothelial cells and thereby controls activation of lipid raft-localized vascular endothelial growth factor receptor-2 and restricts angiogenesis (17).

While the invention is not limited by any particular mechanism of action, provided are methods for using or administering AIBP to regulate inflammatory receptors residing in lipid rafts, including TLRs in macrophages and microglia.

Materials and Methods

Animals: All experiments were conducted according to protocols approved by the Institutional Animal Care and Use Committee of the University of California, San Diego. Mice were housed up to 4 per standard cage at room temperature and maintained on a 12:12 hour light:dark cycle, with lights on at 07:00. All behavioral testing was performed during the light cycle. Both food and water were available ad libitum. Wild type C57Bl/6 male mice were purchased from Harlan (Indianapolis, Ind.) or the Jackson Lab (Bar Harbor, Me.).

Cells: Primary peritoneal macrophages were harvested from C57Bl/6 mice 3 days following an intraperitoneal injection of thioglycollate, selected by adsorption to a plate and maintained in DMEM supplemented with 10% heat-inactivated FBS (Omega Scientific) and 50 μg/ml gentamicin (Omega Scientific). Primary microglia were isolated from 2 to 3 week old C57Bl/6 mice as previously described (1). In brief, brains isolated from 5 to 6 mice were pooled together and homogenized in HBSS (Gibco) supplemented with 0.5% BSA and 1 mM EDTA on ice. A single cell suspension was obtained with a 70 μm cell strainer (Biologix Group) separated on a discontinuous 37-70% Percoll (GE Healthcare) gradient. After removal of a myelin/debris layer, cells were collected from the interphase, washed and plated in DMEM/F12 (Cellgro) supplemented with 5% FBS and 50 μg/ml gentamicin. Cells were supplemented daily for 7 days with 20 ng/ml of recombinant mouse IL-34 (R&D Systems). Immortalized microglial cell line BV-2 (2) were maintained in DMEM supplemented with 5% FBS (Omega Scientific) and 50 μg/ml gentamicin. Ba/F3 cells stably expressing TLR4-gfp, TLR4-flag and MD2 (3, 4) were cultured in RPMI1640 (Invitrogen) containing 70 units/ml recombinant murine interleukin-3, 10% heat-inactivated FBS, 50 μg/ml gentamicin. HEK293 cells were cultured in DMEM supplemented with 10% FBS and 50 μg/ml gentamicin.

Yeast two-hybrid system: Interactions of the ectodomains of TLRs with AIBP were assessed by a yeast two-hybrid assay (BD Clontech, Palo Alto, Calif.). In one experiment (FIG. 1), the EGY48 yeast transformed with p80p-LacZ were co-transformed with pB42AD-AIBP and pLexA-TLR4 (AA 1-629). In a different experiment (FIG. 10), the vectors were switched and yeast were co-transformed pLexA-AIBP and either pB42AD-TLR1 (AA 22-524), pB42AD-TLR4 (AA 1-629), pB42AD-TLR7 (AA 1-795), or pB42AD-TLR9 (AA 1-772). Following selection for a Trp$^+$ and His$^+$ phenotype, Leu-dependent growth and β-gal (LacZ) activity were tested in induction medium (SD/galactose/raffinose). The positive control was the yeast cell line EGY48/p80p-LacZ co-transfected with pLexA53 and pB42ADT; the negative control was the yeast cell line co-transfected with pLexA and pB42AD (5).

AIBP-TLR4 pull-down assay: HEK293 cells were transfected with both the extracellular domain of human flag-TLR4 and human flag-AIBP using GenJet™ In Vitro DNA transfection reagent (SignaGen Laboratories). At 2 days after transfection, cells were lysed with an ice-cold lysis buffer (50 mM Tris-HCl, pH 7.5, 1% NP-40, 150 mM NaCl, 1 mM EDTA, 1 mM EGTA, 5 mM Na$_3$VO$_4$, 1 mM NaF, and a protease inhibitor cocktail from Sigma). Cell lysates were preincubated with protein A/G sepharose beads (GE Healthcare) for 30 min at 4° C. and immunoprecipitated with a rabbit anti-AIBP antibody (Abcam) overnight at 4° C. Next day, the lysates were further incubated with protein A/G Sepharose beads for additional 1 hour at 4° C. Immune complexes were washed five times with lysis buffer, run on a NuPAGE™ gel (Invitrogen), and AIBP-bound TLR4 was detected by immunoblotting with an anti-flag antibody (Sigma).

Flow cytometry binding assay: Primary peritoneal macrophages isolated from wild type and Tlr4$^{-/-}$ mice were plated overnight, then washed with PBS, blocked with TBS containing 1% BSA for 30 min on ice, and incubated with either 2 µg/ml BSA or 2 µg/ml AIBP for 2 hours on ice. Cells were washed three times with PBS and incubated with 1 µg/ml FITC-conjugated anti-His antibody (Abcam) for 1 hour at 4° C. After five washes with PBS, cells were analyzed using a FACSCanto II™ (BD Biosciences, San Jose, Calif.) flow cytometer. Geometric means of FACS histograms were measured and presented as bar graphs.

TLR4 dimerization assay: Ba/F3 cells were pretreated with either 50 µg/ml HDL alone or 50 µg/ml HDL+0.2 µg/ml AIBP. Two hours after pretreatment, cells were stimulated with either DMSO (vehicle) or 10 ng/ml of LPS for 10 min at 37° C. and lysed with an ice-cold lysis buffer (50 mM Tris-HCl, pH 7.5, 1% NP-40, 150 mM NaCl, 1 mM EDTA, 1 mM EGTA, 5 mM Na$_3$VO$_4$, 1 mM NaF, and a protease inhibitor cocktail from Sigma). Cell lysates were preincubated with protein A/G sepharose beads for 30 min at 4° C. and immunoprecipitated with a rabbit anti-GFP antibody (Abcam) overnight at 4° C. Next day, the lysates were incubated with protein A/G sepharose beads for 1 hour at 4° C. Immune complexes were washed five times with lysis buffer, run on a NuPAGE™ gel (Invitrogen), and dimerized TLR4 was detected by immunoblotting with anti-flag (Sigma) and anti-GFP antibodies.

Isolation of lipid rafts: Lipid rafts were isolated using a detergent-free, discontinuous gradient ultracentrifugation method as in our earlier work (6). In brief, BV-2 cells were pretreated with either BSA or AIBP for 2 hours and then stimulated with 10 ng/ml LPS for 10 min. Cells were washed two times with ice-cold PBS and harvested into 1 ml of 0.5 M sodium bicarbonate buffer (pH 11.0) containing a protease inhibitor cocktail, homogenized and sonicated. One ml of disrupted cell suspension was mixed with 1 ml of 90% sucrose in MBS (25 mM 2-(N-morpholino)ethanesulfonic acid, pH6.5, 150 mM NaCl) to adjust to 45% sucrose and placed into ultracentrifugation tubes. Four ml of 5-35% discontinuous sucrose gradient in MBS containing 250 mM sodium bicarbonate was formed above the sample. Following ultracentrifugation at 35,000 rpm in a SW-41 rotor (Beckman) for 20 hours at 4° C., ten 1 ml fractions were collected from top to bottom. The lipid raft fractions 4 and 5 were combined, supplemented with 3× volume of MBS buffer and subjected to an additional round of ultracentrifugation at 35,000 rpm for 2 hours at 4° C. The pellet was re-suspended in LDS sample buffer (Invitrogen), and samples were run on a NuPAGE™ gel, transferred to a PVDF membrane and immunoblotted with the indicated antibodies.

Ex vivo flow cytometry for lipid rafts: C57Bl/6 mice were intrathecally (i.t.) injected with saline or AIBP. Two hours later, mice were intrathecally injected with LPS. Fifteen min after LPS injection, spinal cords were harvested and single-cell suspensions were obtained from spinal cords using a Neural Tissue Dissociation™ kit (Miltenyi Biotec) according to the manufacturer's protocol. To remove myelin, Myelin Removal Beads II™ (Miltenyi Biotec) were added to samples and incubated for 15 min at 4° C., followed by washes and separation with an LS column and a MACS™ Separator (Miltenyi Biotec). Following isolation, cells were washed two times with a FACS buffer (BD Bioscience), incubated with an anti-CD16/CD32 antibody (FcRγ blocker, BD Bioscience) for 10 min at room temperature, followed by staining with an APC-conjugated CD11b antibody (BD Bioscience) and FITC-conjugated cholera toxin B (Sigma) for 1 hour on ice. Cells were washed two times with a FACS buffer, fixed with 3.7% formaldehyde for 15 min on ice, washed three times with a FACS buffer, and analyzed using a FACSCanto II™ (BD Biosciences) flow cytometer.

Immunoblot. Antibodies specific to FLOT1, phospho-p65, p65, phospho-ERK1/2, ERK1/2, and GAPDH (Cell Signaling Technology) and a TLR4 antibody (GenWay Biotech). Antibodies specific to FLAG and GFP were purchased from Sigma-Aldrich and Abcam, respectively. Cell lysates were subjected to gel electrophoresis and immunoblot as described(7).

Quantitative PCR. Total RNA was isolated using Nucleo-spin™ RNA columns (Clontech). Isolated RNA was reverse transcribed using RNA to cDNA EcoDry (Clontech) following the manufacturer's protocol. Quantitative PCR was performed using KAPA SYBR FAST™ Universal qPCR kit (KAPA Biosystems, KK4602), with the primers ordered from Integrated DNA Technologies (IDT), and a Rotor Gene Q™ thermocycler (Qiagen).

Recombinant AIBP: AIBP was produced in a baculovirus/insect cell system to allow for posttranslational modification and to ensure endotoxin-free preparation. Human AIBP was cloned into a pAcHLT-C vector behind the polyhedrin promoter. The vector contains an N-terminal His-tag to enable purification and detection. Insect Sf9 cells were transfected with BD BaculoGold™ Baculovirus DNA and the AIBP vector. After 4-5 days, the supernatant was collected to afford a baculovirus stock. Fresh Sf9 cells were infected with the AIBP producing baculovirus, cell pellets were collected after 3 days, lysed, sonicated, cleared by centrifugation, and the supernatants loaded onto a Ni-NTA agarose column eluted with imidazole. Protein was dialyzed against saline, and concentration measured. Aliquots were stored at −80° C.

LPS and cyclodextrin: In vitro experiments were conducted with Kdo2-LipidA (KLA; Avanti Polar Lipids), a well-characterized active component of LPS and a highly specific TLR4 agonist (8). Our earlier studies have demonstrated that i.t. injections of KLA or ultra-pure LPS from *Escherichia coli* 0111:B4 (Invivogen) produced identical allodynia responses in mice (9). In this study we used for i.t. injections Invivogen's LPS at 0.1 µg/5 µl in 0.9% saline. The pharmaceutical grade beta-cyclodextrin CAVAMAX W7 PHARMA™ was from Wacker Chemie AG.

Cisplatin treatment: Mice received intraperitoneal (i.p.) injections of cisplatin (2.3 mg/kg/injection; Spectrum Chemical MFG) every other day for 6 total injections to induce tactile allodynia. Between cisplatin injection days, lactated Ringer's solution (0.25 ml) was injected to maintain hydration and to protect the kidney and liver. During the period of cisplatin administration, gross behavioral observations were made and animals were assessed for general health, including changes in body weight. In case of dehydration, additional lactated Ringer's solution was administered. In the study, the criteria for euthanasia was weight loss in excess of 20%, however, no animals required euthanasia.

Mouse intrathecal (i.t.) injection: Mice were anesthetized using 4% isoflurane for induction and 2.5% for maintenance of anesthesia with a mixture of 50% oxygen and 50% room air. The lower back was shaven and the animal was placed in a prone posture so that the pelvis could be held between the thumb and forefinger. The L5 and L6 vertebrae were identified by palpation and a 30G needle was inserted percutaneously on midline between the L5 and L6 vertebrae. Successful entry was assessed by the observation of a brisk tail flick. Injections of 5 µl were administered over an interval of approximately 30 seconds. Following recovery from anesthesia, mice were evaluated for normal motor coordination and muscle tone.

Mechanical allodynia: For testing, animals were placed in clear, plastic, wire mesh-bottomed cages for 45 min prior to the initiation of testing. Tactile thresholds were measured with a series of von Frey filaments (Semmes Weinstein von Frey Anesthesiometer; Stoelting Co.) ranging from 2.44 to 4.31 (0.04-2.00 g). The 50% probability of withdrawal threshold was recorded. In light of reports of the possible contribution of sex of the experimenter (10), we note that a female performed the mouse behavioral testing. In the present experiments, mechanical withdrawal thresholds were assessed prior to treatment and at enter times post-treatment using the up-down method (11).

Formalin Flinching: A metal band was placed around the left hindpaw of the mouse. After 1 hour acclimation with the metal band, the mouse received a single injection of intraplantar formalin (2.5%) to induce flinching. The movement of the metal band (mouse flinching) was detected by an automated device (12) for a period of 1 hour after delivery of formalin.

Statistical Analyses: Results were analyzed using Student's t-test (for differences between 2 groups) or two-way ANOVA with the Bonferroni post hoc test (for time course experiments), using GraphPad Prism™. Differences between groups with $p<0.05$ were considered statistically significant. We did not use statistical methods to predetermine sample size, there was no randomization designed in the experiments, and the studies were not blinded. Samples sizes were estimated on the basis of previous experimental studies. No exclusion criteria were used in these studies.

Results and Discussion

Figure 10:
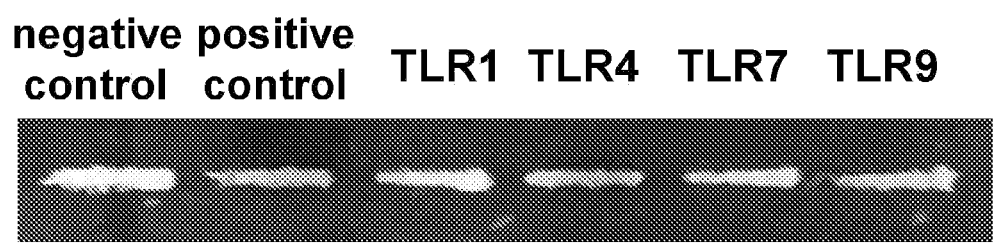
FIG. 10 illustrates data demonstrating that AIBP binds TLR4 but not TLR1, TLR7 or TLR9; yeast two-hybrid was performed with pLexA-AIBP and TLR ectodomains cloned into pB42AD, as discussed in detail in Example 2, below.
Figures 11A, 11B:
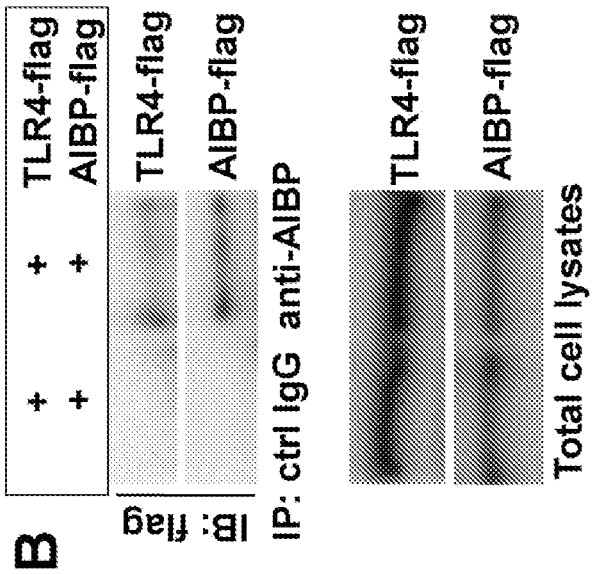
FIG. 11A, FIG. 11B, FIG. 11C, FIG. 11D, illustrate that AIBP binds TLR4 and inhibits TLR4 dimerization, as discussed in detail in Example 2, below.
Figure 11C:
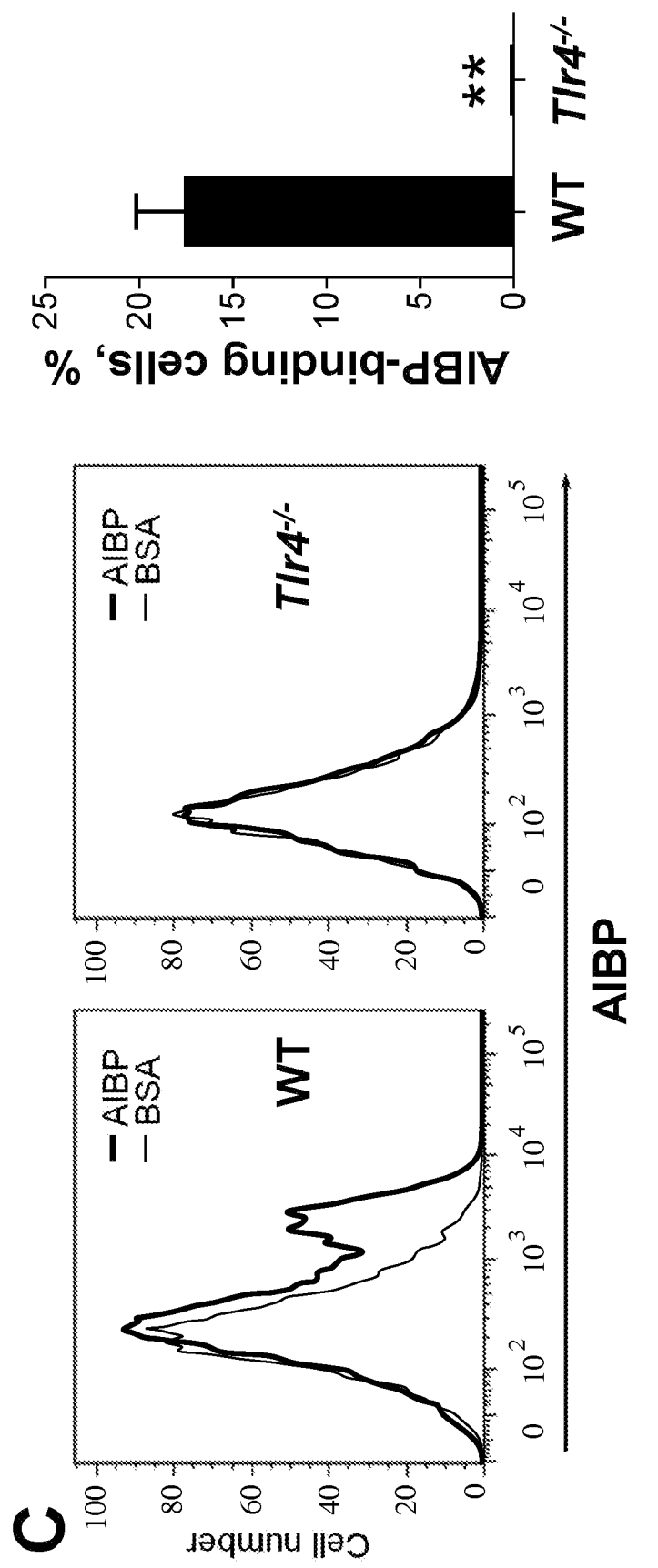

Using yeast two-hybrid system, we demonstrated constitutive AIBP binding to the TLR4 ectodomain, but not to ectodomains of TLR1, TLR7 or TLR9 (FIG. 11A and FIG. 10). The AIBP-TLR4 binding was confirmed in a pull-down experiment with AIBP and TLR4 ectodomain expressed in HEK 293 cells (FIG. 11B). In addition, recombinant AIBP bound to peritoneal macrophages from wild type (WT) but not Tlr4$^{-/-}$ mice (FIG. 11C). These results led us to hypothesize that AIBP targets TLR4-occupied lipid rafts and that, in turn, AIBP-mediated raft disruption interferes with ligand-induced TLR4 dimerization. Indeed, AIBP treatment inhibited LPS-induced TLR4 dimerization in Ba/F3 cells expressing TLR4-flag, TLR4-gfp and MD2 (FIG. 11D).

Figure 11D:
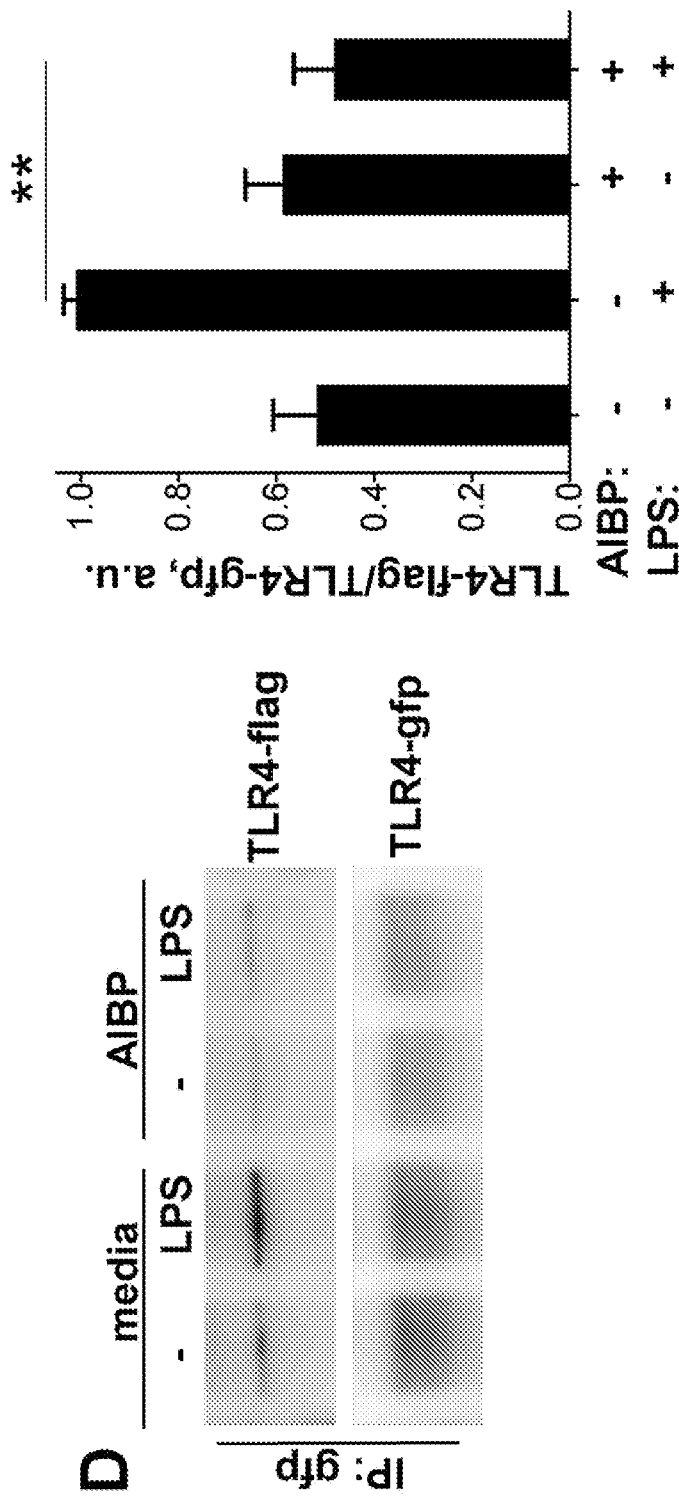

FIG. 11A, FIG. 11B, FIG. 11C, FIG. 11D, illustrate that AIBP binds TLR4 and inhibits TLR4 dimerization: FIG. 11A shows a Yeast two-hybrid study performed with pB42AD-AIBP and pLexA-TLR4 ectodomain; FIG. 11B graphically illustrates data where HEK293 cells were co-transfected with the flag-tagged TLR4 ectodomain and flag-tagged AIBP; AIBP from cell lysates were pulled downed with an anti-AIBP antibody or an isotype control IgG, and blots of the pull-down or total cell lysates were probed with an anti-flag antibody; FIG. 11C graphically illustrates data where peritoneal elicited macrophages from WT and Tlr4−/− mice were incubated for 2 hours on ice with 2 µg/ml BSA or 2 µg/ml AIBP (with a His-tag) and then subjected to a flow cytometry analysis with a FITC-conjugated anti-His antibody; FIG. 11D graphically illustrates data where Ba/F3 cells stably expressing TLR4-gfp, TLR4-flag and MD2 were incubated with serum-free media containing 50 m/ml HDL, in the presence or absence of 0.2 µg/ml AIBP, and then stimulated with 10 ng/ml LPS for 20 min; cell lysates were immune-precipitated with an anti-GFP antibody and blots were probed with anti-flag and anti-GFP antibodies; Mean±SEM; n=4-6; **, $p<0.01$; Student's t-test.

Earlier studies have demonstrated that TLR4 serves as a pervasive mediator of persistent pain states. TLR4 deficiency results in a complete attenuation of tactile allodynia during treatment with the chemotherapeutic cisplatin and during the persistent pain state after the cisplatin treatment was completed (10, 11). Experiments with nerve injury and arthritis models also support the role of TLR4 in mediating the transition from an acute to a persistent pain state (7-11, 18, 19). Tellingly, intrathecal (i.t.) injections of LPS, a specific TLR4 ligand, but not of LPS-RS, which does not activate TLR4, result in immediate tactile allodynia (19). The mechanism involves TLR4-mediated release of inflammatory cytokines from microglia and/or astrocytes which in turn leads to central sensitization and allodynia (2, 19, 20).

Figure 12A:
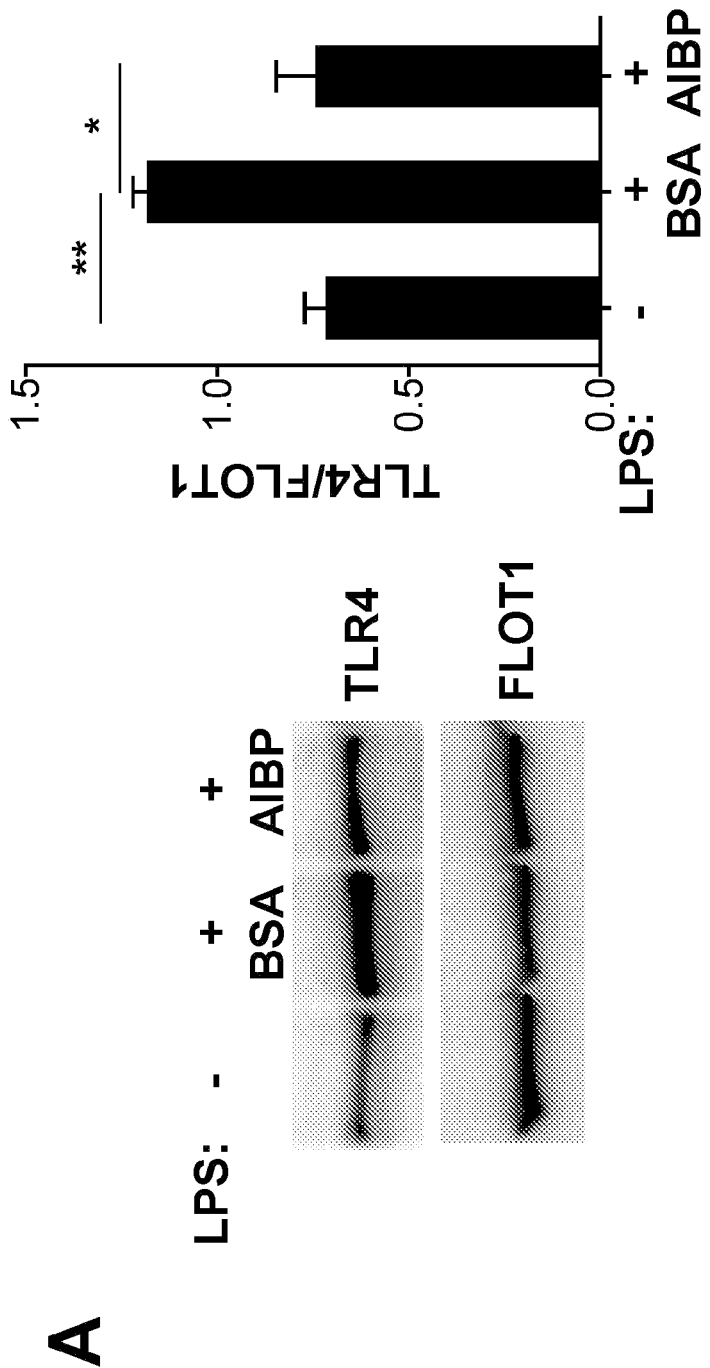
FIG. 12A, FIG. 12B, FIG. 12C, FIG. 12D illustrates that AIBP reduces inflammatory responses in microglia, as discussed in detail in Example 2, below.

Hence, we tested whether AIBP affects TLR4 in microglia. Exposure to LPS results in a greater TLR4 recruitment to lipid rafts, where the receptors dimerize and initiate inflammatory signaling (21). Treatment with AIBP reduced LPS-induced TLR4 occupancy in lipid rafts in microglia-like BV-2 cells (FIG. 12A). In these cells, AIBP treatment also resulted in inhibition of p65 and ERK1/2 phosphorylation (FIG. 12B) and inflammatory cytokine mRNA expression (FIG. 12C) in response to LPS. These results were replicated in primary mouse microglia in which AIBP completely inhibited LPS-induced expression of the majority of inflammatory cytokines (FIG. 12D).

Figure 12B:
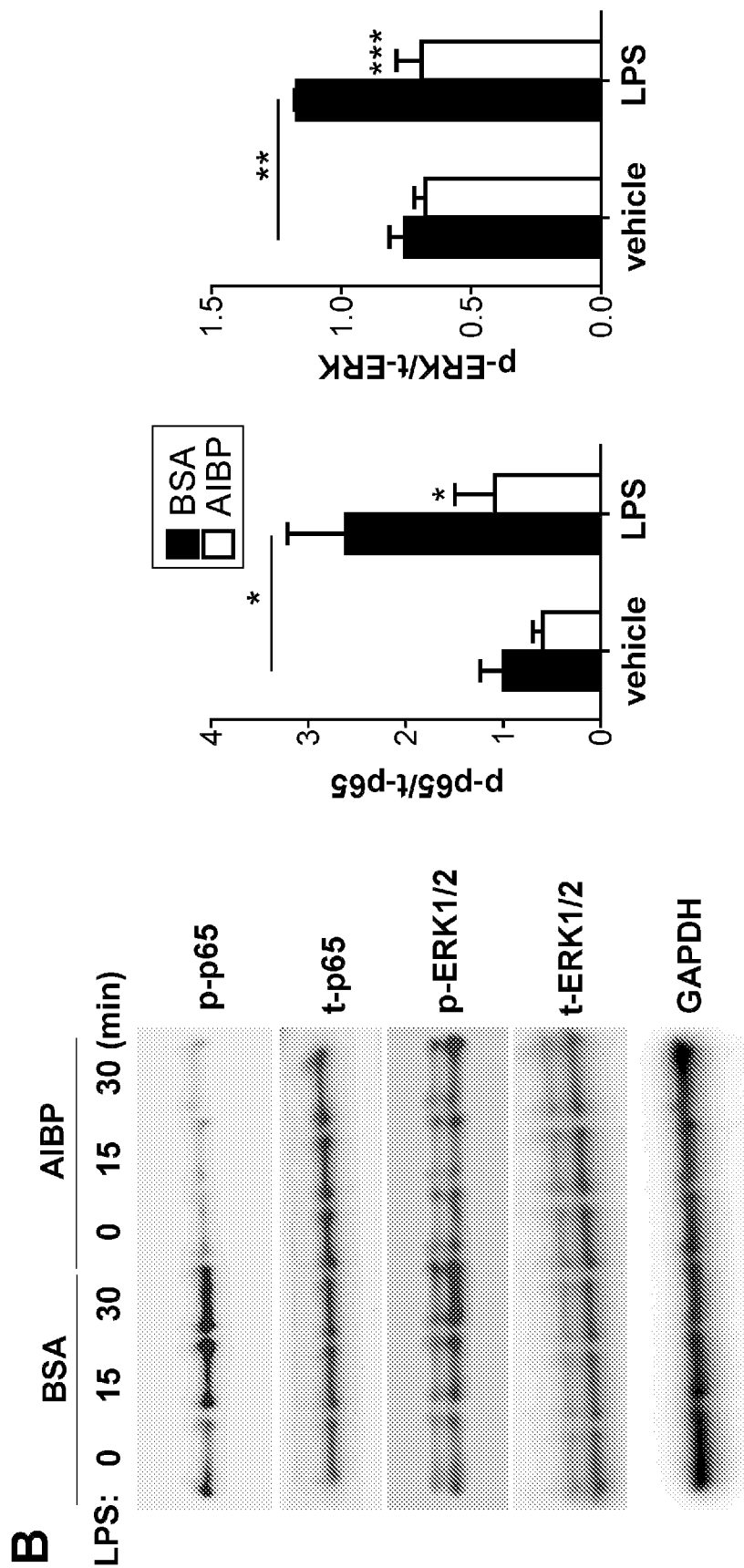
Figure 12C:
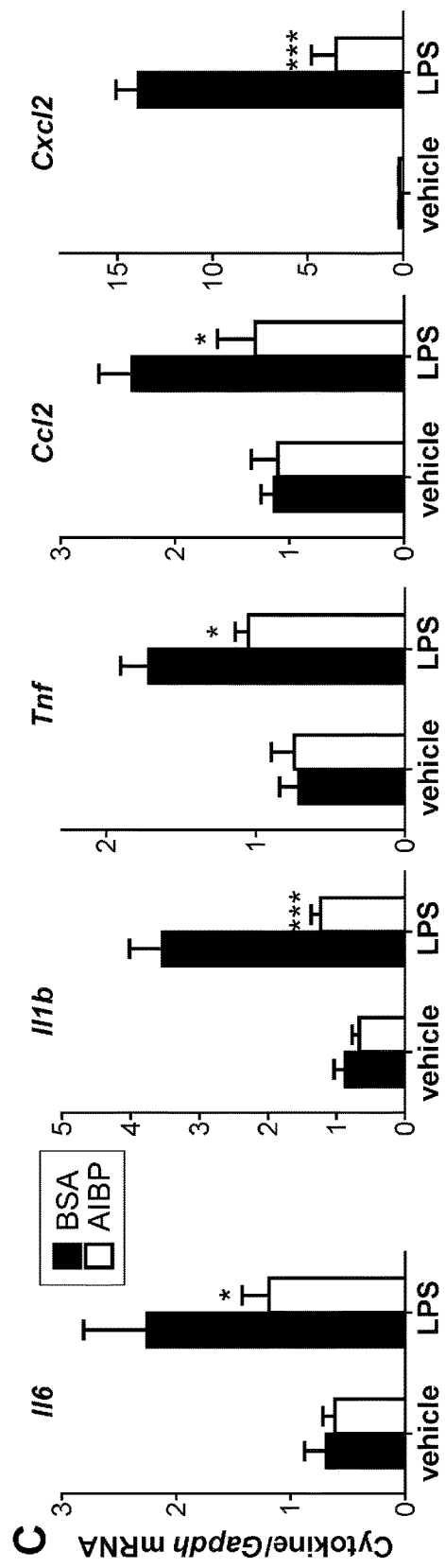
Figure 12D:
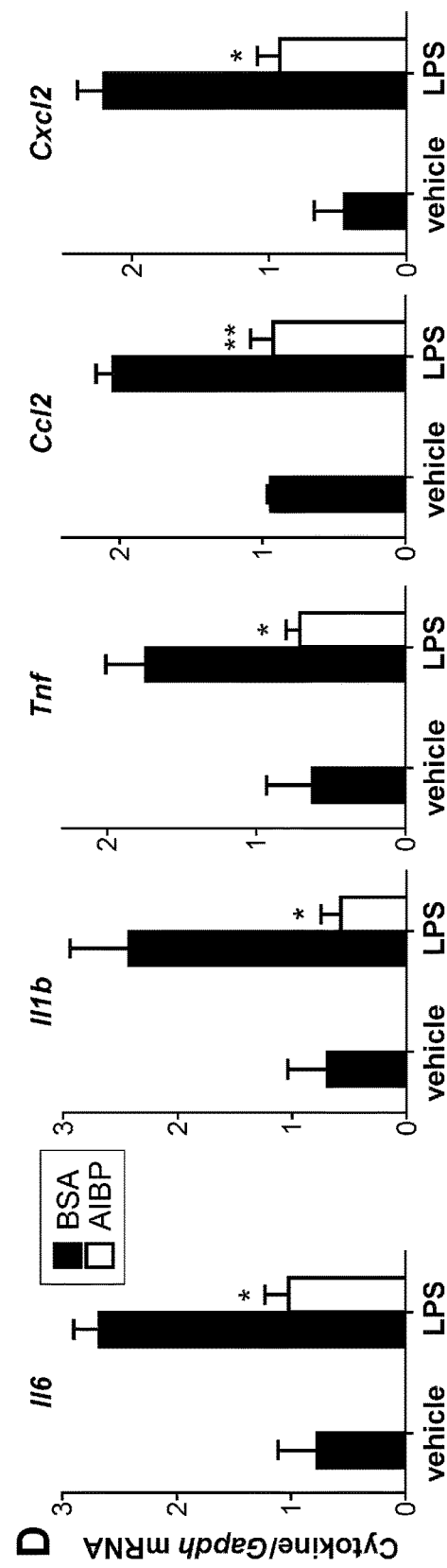

FIG. 12A, FIG. 12B, FIG. 12C, FIG. 12D illustrate that AIBP reduces inflammatory responses in microglia: FIG. 12A-C illustrate data from studies where BV-2 cells were incubated for 2 hours with vehicle (0.1% BSA) or 0.2 µg/ml AIBP (in 0.1% BSA) in serum-containing medium and stimulated with 10 ng/ml LPS. TLR4 occupancy in lipid rafts was tested 15 min after adding LPS (FIG. 12A), p65 and ERK1/2 phosphorylation after 30 min (FIG. 12B), and cytokine mRNA expression after 2 h of incubation (FIG. 12C); and FIG. 12D graphically illustrates data from studies where Primary mouse microglia (pooled from 5-6 mice per sample) were incubated for 2 hours with vehicle (0.1% BSA) or 0.2 µg/ml AIBP (in 0.1% BSA) in serum-containing medium and stimulated with 10 ng/ml LPS for 1 hour; Mean±SEM; n=4-6 for BV-2; n=3 for primary microglia experiments; *, $p<0.05$; , $p<0.01$; **, $p<0.0005$ (Student's t-test).

Figure 13A:
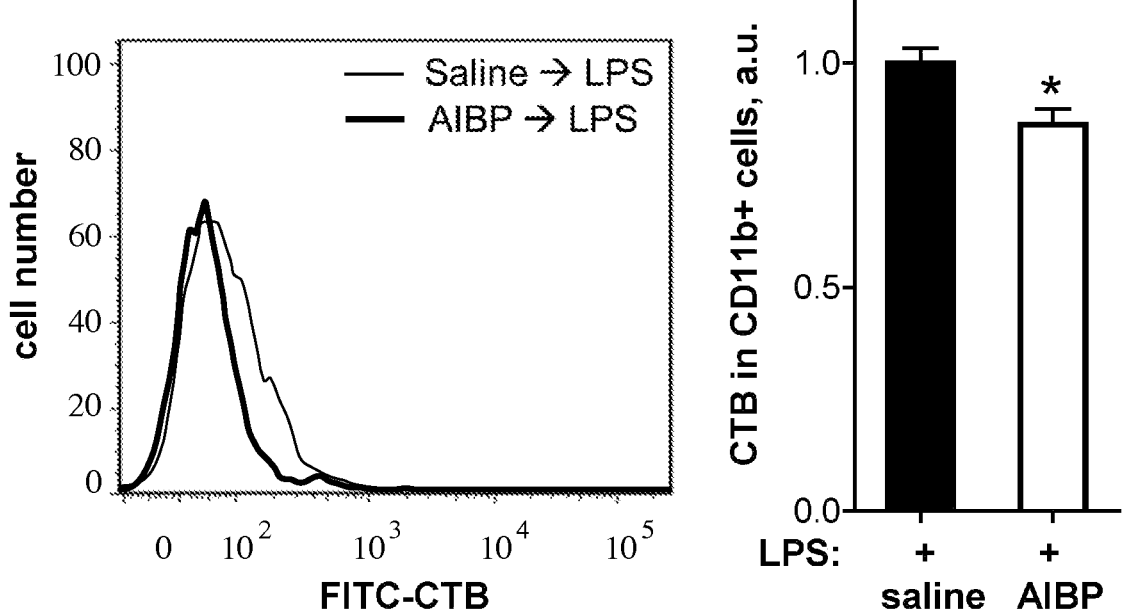

To examine whether AIBP reduces lipid rafts in spinal cord microglia in vivo, we i.t. injected mice with saline or recombinant AIBP two hours prior to the i.t. injection of LPS. AIBP significantly reduced the abundance of lipid rafts in spinal microglia compared to saline, as was measured ex vivo by cholera toxin B binding (FIG. 13A). AIBP-imposed lipid raft reductions in spinal microglia in LPS-treated animals averaged 14%. We hypothesize that this moderate change in membrane microdomain organization is sufficient to physiologically inhibit TLR4-mediated neuroinflammation and neuropathic pain, but would not interfere with normal neuronal function.

Figure 14:
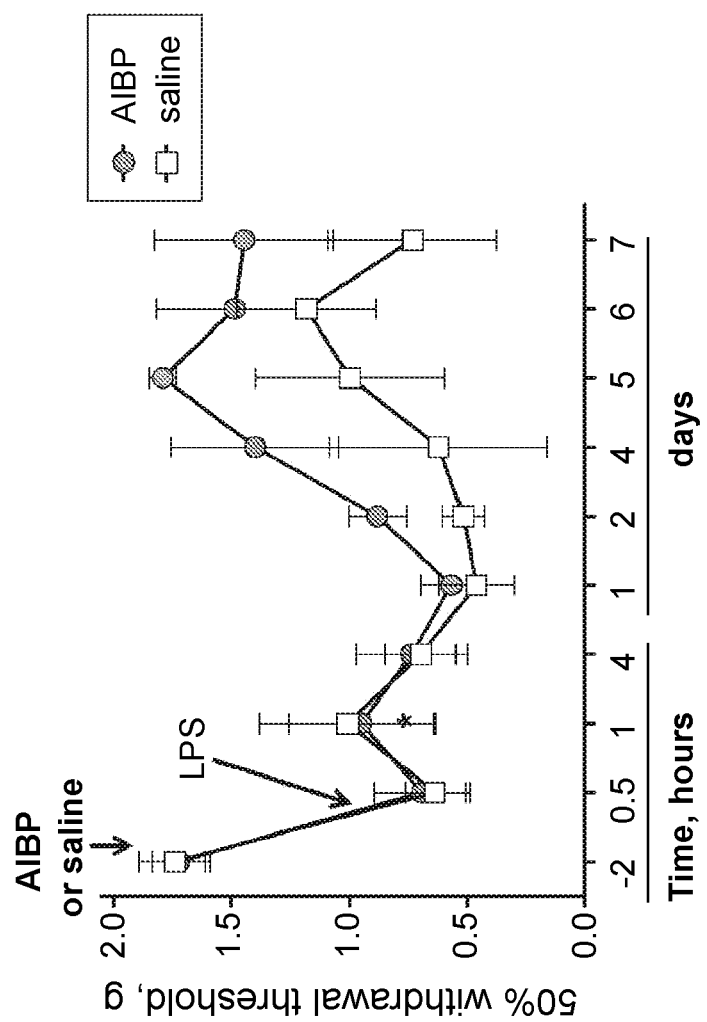
FIG. 14 graphically illustrates data from studies of Intrathecal injections of AIBP and LPS in female mice, as discussed in detail in Example 2, below.

To test this hypothesis, mice were injected with i.t. saline or recombinant AIBP, followed by the i.t. injection of LPS, and tested for allodynia. We have earlier demonstrated that allodynia response to i.t. LPS in female mice is less robust than in males (22). Indeed, i.t. LPS induced only partial reduction in the tactile threshold level in female mice, and AIBP was ineffective in the early stages of allodynia, although the recovery phase trended faster in i.t. AIBP animals compared to i.t. saline (FIG. 14).

Figure 13B:
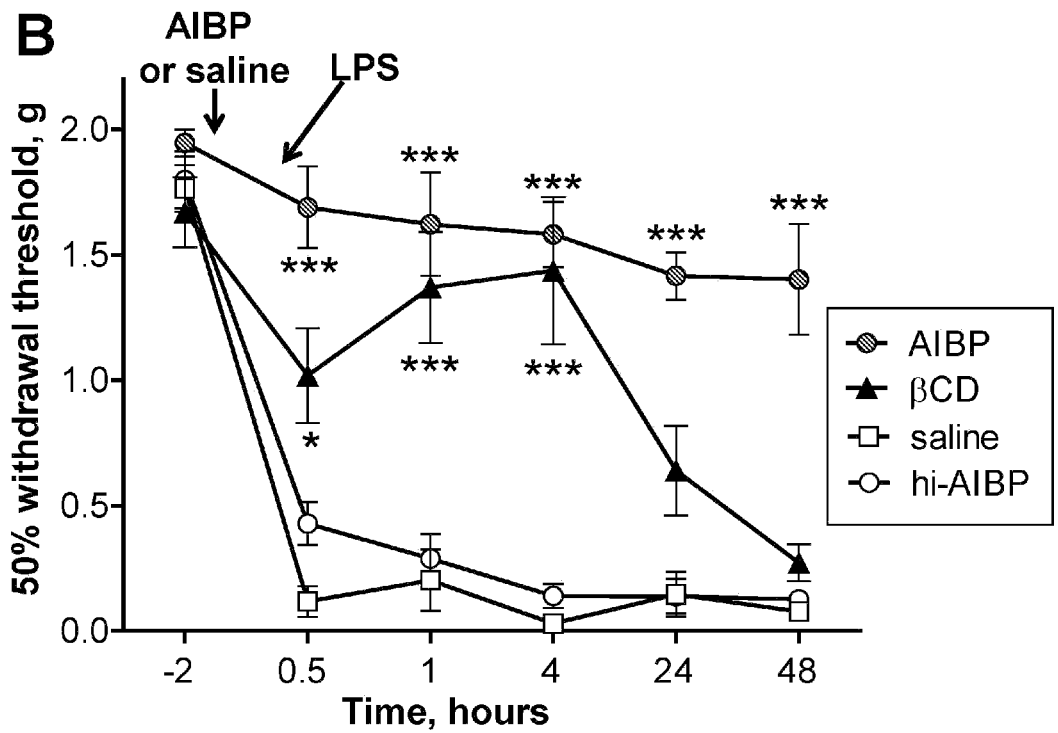

In contrast to females, LPS induced severe tactile allodynia in male mice, which was expected from our previous experiments (19, 22). Remarkably, the initial i.t. injection of AIBP significantly prevented LPS-induced allodynia, whereas injections of denatured, heat-inactivated AIBP had no antagonistic effect (FIGS. 13A, 13B).

Next, we compared the therapeutic effect of AIBP with that of a beta-cyclodextrin (βCD). βCDs are heptamer cyclic oligosaccharides, commonly used to solubilize hydrophobic molecules in pharmaceutic formulations as well as to remove membrane cholesterol in cell culture experiments and thus serving as a method to disrupt lipid rafts. βCDs inhibit TLR4-mediated inflammatory responses in vitro (23, 24). I.t. βCD prevented LPS-induced allodynia for up to 4 hours, but unlike AIBP, βCD was not effective at 24 and 48 hour time points (FIG. 13B). Because of the differences in the response to i.t. AIBP between male and female mice, we focused in subsequent studies on male mice.

We observed no motor deficits in animals injected with i.t. AIBP. Animals were systematically characterized for symmetrical gait, hind limb weight bearing, pinnae and blink reflexes and hind paw placing and stepping (P/S). P/S assesses the integrity of light touch (Aβ afferents from dorsum of paw) and the intact spinally mediated reflex involving plantar placement and spreading of the digits, reflecting fine motor control of ankle and paw. All of these measures (except pinnae and blink) are depressed or lost in a dose dependent fashion after i.t. local anesthetics and botulinum toxin (25, 26), but were unaffected in i.t. AIBP injected animals, attesting to intact motor function.

Our studies demonstrated a novel mechanism and role for AIBP in preventing neuropathic pain. However, from the clinical perspective, reversal of chronic pain would have much greater health benefit for affected populations. To test the therapeutic potential of AIBP in reversing neuropathic pain, we first i.t. injected male mice with LPS, followed after 24 hours by i.t. saline or AIBP. After i.t. LPS, mice developed severe allodynia. However, the allodynia was markedly attenuated by a single injection of AIBP, but not saline (FIG. 13C).

Figure 15:
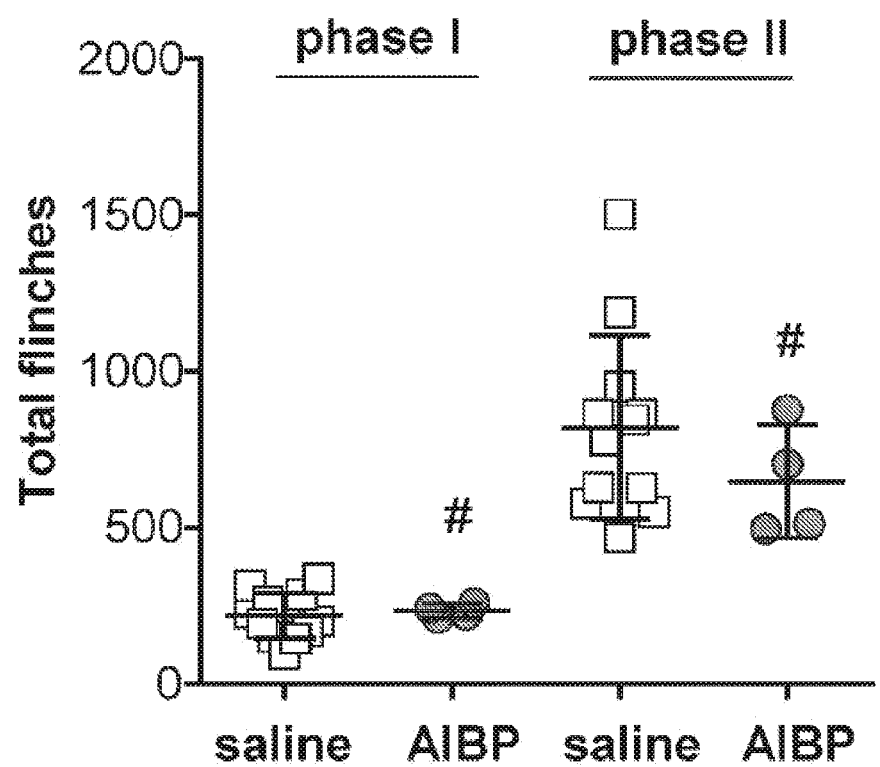
FIG. 15 graphically illustrates data from studies showing that Intrathecal AIBP does not affect acute post-formalin paw flinching, as discussed in detail in Example 2, below.

In a different model of chronic pain, intraplantar injection of formalin yields acute flinching, a coordinated, high frequency extension and flexion of the injected hind paw, and after a 7 day delay, a persistent tactile allodynia progressively develops along with an associated activation of spinal microglial (27). In this model, we subjected male mice to i.t. injections of saline or AIBP, followed by intraplantar injection of formalin. AIBP had no effect upon phase 1 or 2 formalin-evoked hind paw flinching (FIG. 15). An unaffected acute flinching behavior after i.t. AIBP again attests to normal motor function. However, AIBP reduced the allodynia otherwise observed on the 7th day after administration of formalin (FIG. 13D). In a different experiment, mice first received intraplantar formalin and 7 days later i.t. AIBP or saline. AIBP but not saline significantly reversed allodynia (FIG. 13E). These results demonstrate that AIBP controls the development of chronic pain following acute injury.

Figure 13F:
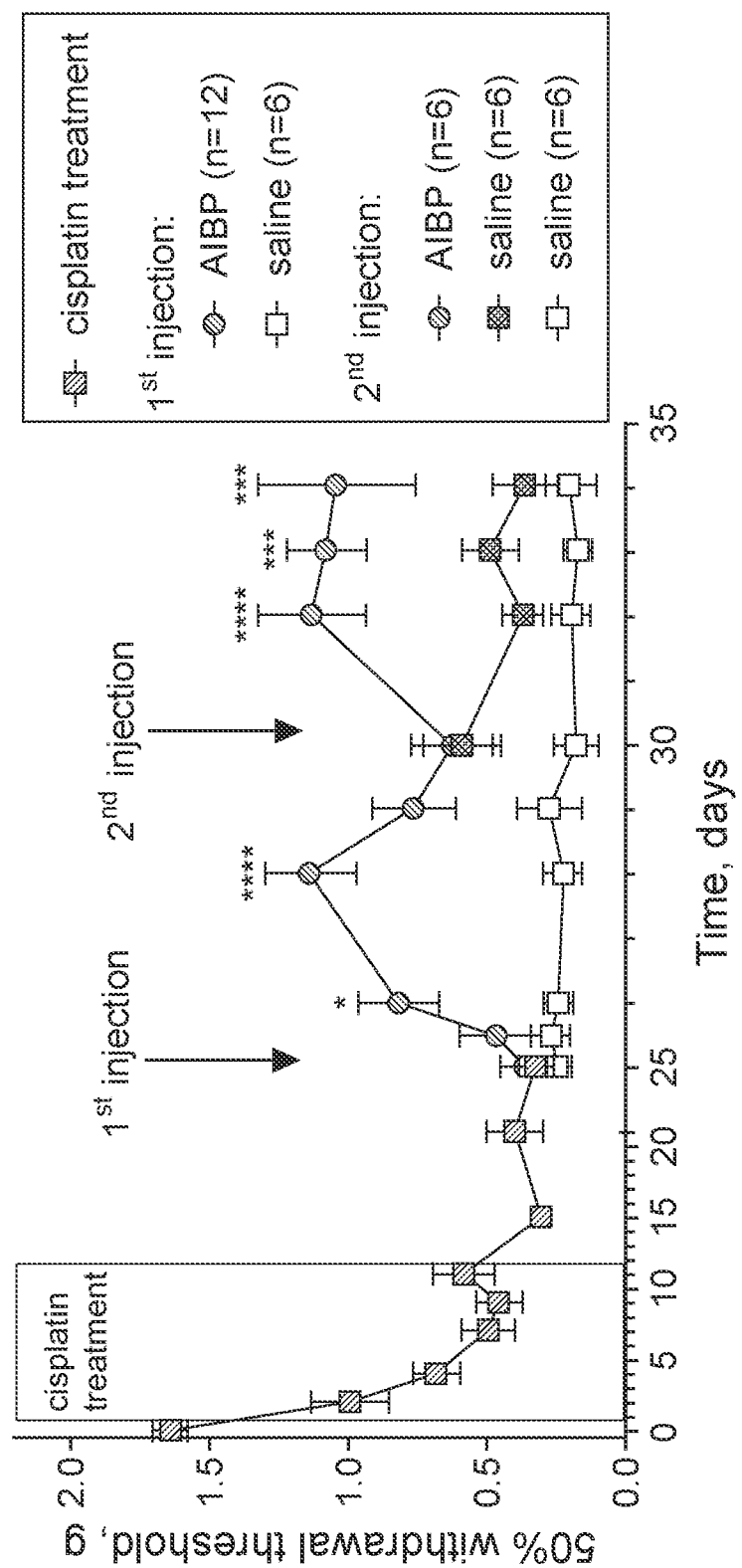

In rodents, as in people, the chemotherapeutic cisplatin induces long-lasting tactile allodynia. A single i.t. AIBP injection significantly reversed established cisplatin-induced allodynia, and a second injection produced longer efficacy (FIG. 13F).

To the best of our knowledge, there is no current therapy that reverses established chemotherapy-induced peripheral neuropathy (CIPN) (28-30). The therapeutic effect and the absence of side effects observed in AIBP treated mice validates and demonstrates the novel approach to treatment of CIPN in patients as provided herein.

The need for neuraxial delivery in humans does not constitute a barrier for developing AIBP therapy. Intrathecal therapy has significant precedent, particularly for specific groups of patients including those with CIPN (31). The case has been made that the intrathecal route is a useful and efficacious route of administration for certain therapeutic proteins, peptides and oligonucleotides as opposed to small molecules (32-34). Additionally, in alternative embodiments, for AIBP therapy as provided herein, AIPB is delivered to the CNS using moieties that target and/or allow entry into the CNS, e.g., allow therapeutic amounts of AIBP to pass through the BBB and enter the CNS.

Noting that this invention is not limited by any particular mechanism of action, this work focused on AIBP-mediated inhibition of TLR4 localization to lipid rafts, TLR4 dimerization, signaling and expression of inflammatory cytokines. Similar to i.t. administration of βCD, a chemical disrupting lipid rafts, i.t. AIBP prevented TLR4-mediated allodynia in mice (FIG. 13B). However, unlike βCD, AIBP inhibition of allodynia was sustained, which might be because in contrast to indiscriminate disruption of lipid rafts by βCD, raising spinal AIBP levels amplifies a natural mechanism controlling TLR4 occupancy in lipid rafts. AIBP is present in the cerebrospinal fluid (16).

FIG. 13A, FIG. 13B, FIG. 13C, FIG. 13D, FIG. 13E, FIG. 13F illustrate data showing that intrathecal AIBP prevents and reverses allodynia. A, Male mice were given an i.t. injection of AIBP (0.5 µg/5 µl) or saline (5 µl); two hours later, all mice were given an i.t. injection of LPS (0.1 µg/5 µl) and were terminated 15 min later. Spinal cords were isolated, demyelinated, stained for CD11b and cholera toxin B (CTB) and subjected to a flow cytometry analysis. Mean±SEM; n=11; *, p<0.05 (Student's t-test). FIG. 13A-13B, following baseline von Frey threshold testing, male mice were given an i.t. injection of AIBP (0.5 µg/5 µl), heat-inactivated hi-AIBP (0.5 µg/5 µl), beta-cyclodextrin (5 µl of 10% solution in saline), or saline (5 µl). Two hours later, all mice were given an i.t. injection of LPS (0.1 µg/5 µl) and tested over time for tactile allodynia; Mean±SEM; n=4-6; *, p<0.01; ***, p<0.0001 (two-way ANOVA with Bonferroni post-test). FIG. 13C, Following baseline von Frey threshold testing, male mice were given i.t. LPS (0.1 µg/5 µl). Twenty-four hours later, mice received i.t. AIBP (0.5 µg/5 µl) or saline (5 µl). Mean±SEM; n=4 per group; *, p<0.05 (Student's t-test for the 48 hour time point only). FIG. 13D, Following baseline von Frey threshold testing, male mice were given an intraplantar injection of formalin in one hind paw. The graph shows $baseline-normalized changes in the withdrawal threshold in the ipsilateral paw. Mean±SEM; n=4-12 per group; *, p<0.05 (Student's t-test for the 7 day time point only). FIG. 13E, In a different group of male mice, von Frey readings were #normalized at the 7th day post-formalin and the mice received i.t. AIBP (0.5 µg/5 µl) or saline (5 µl). Mean±SEM; n=4 per group; *, p<0.05 between 0 and 24 hours (repeated measures one-way ANOVA with Bonferroni post-test). FIG. 13F, Male mice (n=18) received 6 i.p. injections of cisplatin (2.3 mg/kg) over a period of 11 days (gray shaded box) to establish allodynia. On day 25, twelve mice were treated with 1st i.t. AIBP (0.5 µg/5 µl; red circles) and six mice with i.t. saline (white squares). On day 30, mice received 2nd i.t. injection: 1) six mice that received AIBP were injected with AIBP (red circles); 2) six mice that received AIBP were injected with saline (dark grey squares); and 3) mice receiving saline were injected with saline (white squares). Mean±SEM. *, p<0.05; *, p<0.001; **, p<0.0001 (two-way ANOVA with Bonferroni post-test).

FIG. 14 graphically illustrates data from studies of Intrathecal injections of AIBP and LPS in female mice. Following baseline von Frey threshold testing, female mice were given an i.t. injection of AIBP (0.5 µg/5 µl) or saline (5 µl). Two hours later, all mice were given an i.t. injection of LPS (0.1 µg/5 µl) and tested over time for tactile allodynia. Mean±SEM; n=4; no statistically significant differences (two-way ANOVA with Bonferroni post-test).

FIG. 15 graphically illustrates data from studies showing that Intrathecal AIBP does not affect acute post-formalin paw flinching. Animals were given an intraplantar injection of formalin in one hind paw. The graph shows total numbers of hind paw flinches in phase I (1-9 min) and phase II (10-50 min). Mean±SD; n=4-12 per group; #, non-significant, p>0.05 (Student's t-test).

Example 3: Efficacy Demonstrated in Exemplary Methods—AIBP Treats and Prevents Neurodegeneration and Neurodegenerative Diseases or Conditions This example describes and demonstrates exemplary embodiments, and the efficacy of methods as provided herein to e.g., to treat, prevent, decrease the severity of or ameliorate neurodegeneration and/or neuroinflammation, including e.g., a neurodegenerative disease such as Alzheimer's disease, chronic traumatic encephalopathy (CTE) or CNS or nerve damage due to trauma, such as traumatic brain injury (TBI).

Figure 16A:
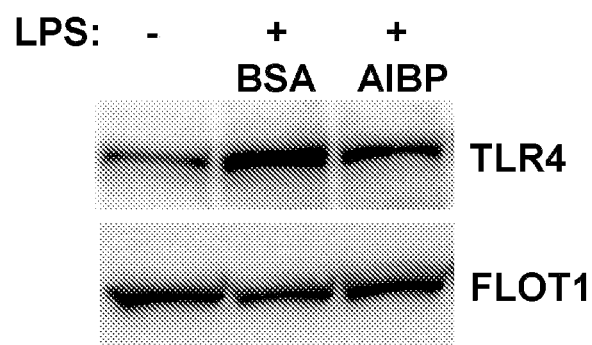
FIG. 16A-B schematically and graphically illustrate that AIBP reduces TLR4 occupancy in microglia lipid rafts, as discussed in detail in Example 3, below.
Figure 16B:
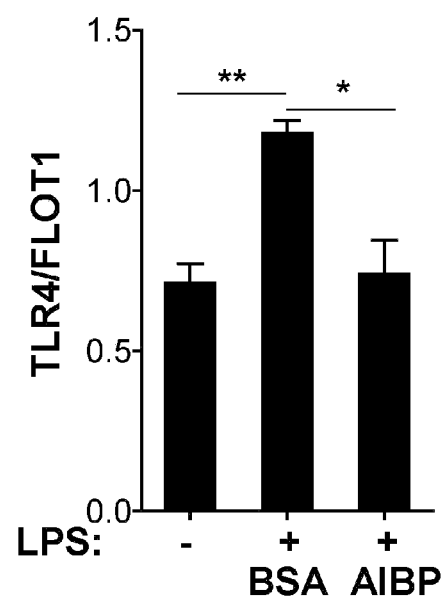

Our studies, using both in vitro systems and animal models, have demonstrated that AIBP reduces pathologic lipid rafts and the occupancy of inflammatory receptors (TLR4) in lipid rafts; see e.g., ref [1] and FIGS. 1 and 11 to 14, and discussions, above. See also FIG. 16, which schematically and graphically illustrates that AIBP reduces TLR4 occupancy in microglia lipid rafts. BV-2 microglia cells were incubated for 2 hours with vehicle (0.1% BSA) or 0.2 µg/ml AIBP (in 0.1% BSA) in serum-containing medium and stimulated with 10 ng/ml LPS. TLR4 occupancy in lipid rafts was tested 15 min after adding LPS. Mean±SEM; n=6; *, p<0.05; **, p<0.01 (Student's t-test).

Figure 17A:
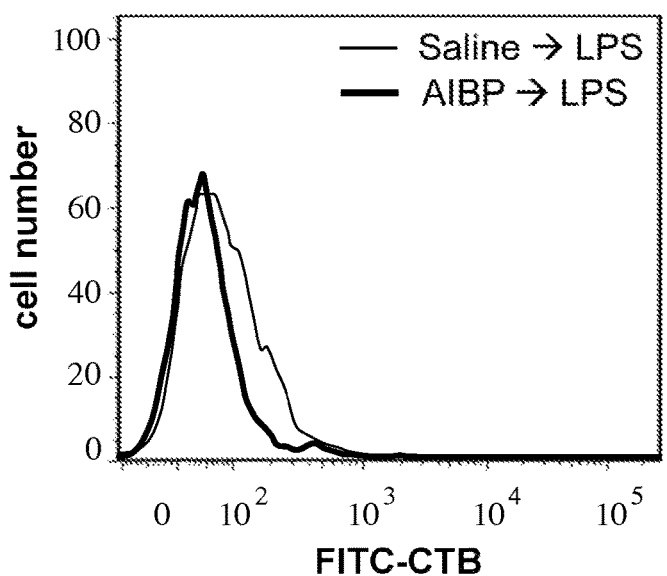
FIG. 17A-B graphically illustrate data showing that AIBP reduces lipid rafts in vivo in spinal cord microglia, as discussed in detail in Example 3, below.
Figure 17B:
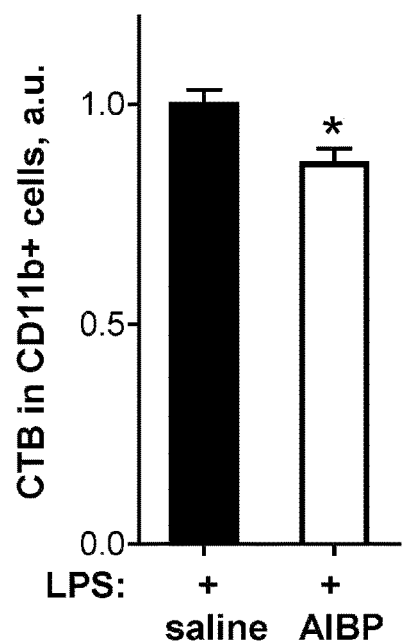

FIG. 17 graphically illustrates data showing that AIBP reduces lipid rafts in vivo in spinal cord microglia. Male mice were given an i.t. injection of AIBP (0.5 µg/5 µl) or saline (5 up; two hours later, all mice were given an i.t. injection of LPS (0.1 µg/5 µl) and were terminated 15 min later. Spinal cords were isolated, demyelinated, stained for CD11b and cholera toxin B (CTB) and subjected to a flow cytometry analysis, FIG. 17A, results graphically displayed in FIG. 17B. Mean±SEM; n=11; *, p<0.05 (Student's t-test).

Figures 18A, 18B:
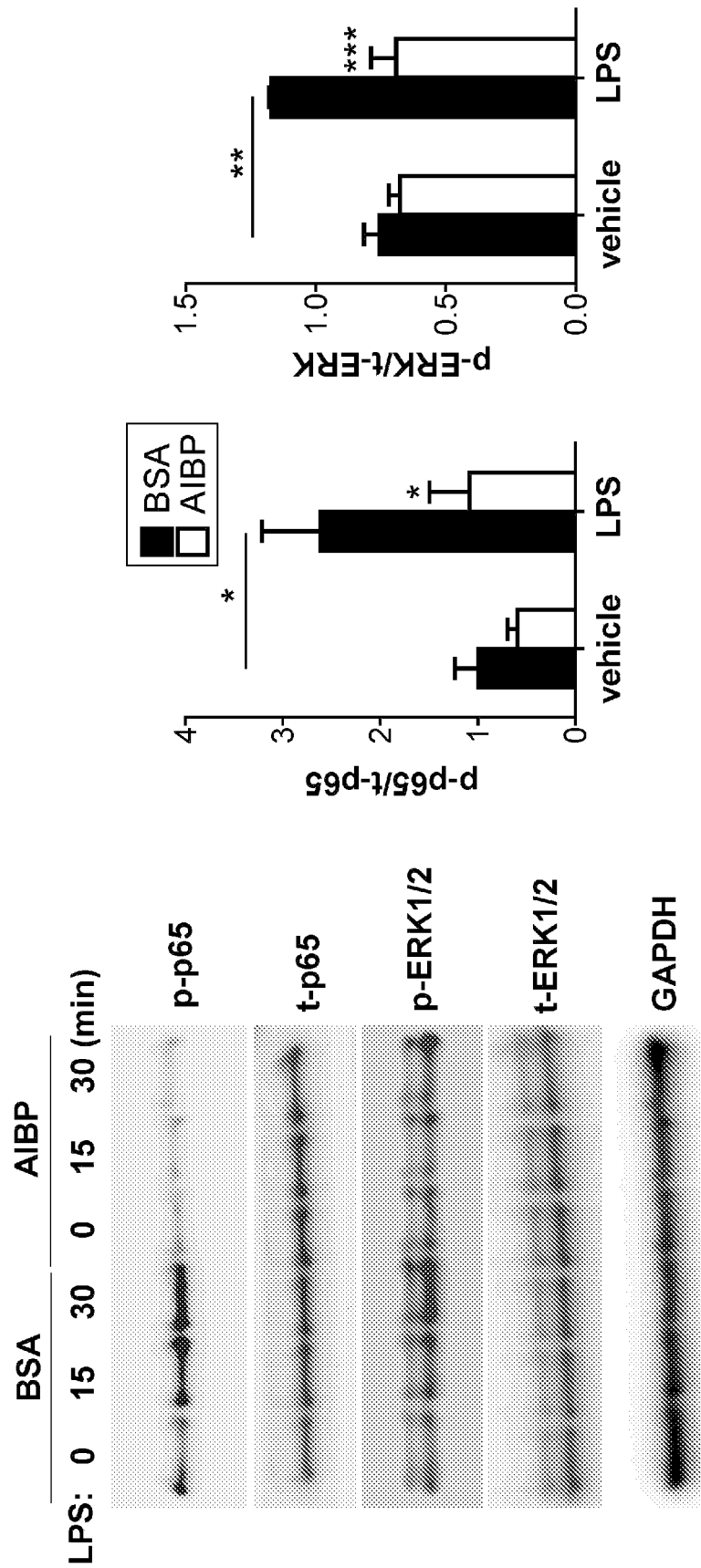
FIG. 18A-D schematically and graphically illustrate that AIBP reduces inflammatory responses in microglia, as discussed in detail in Example 3, below.
Figure 18C:
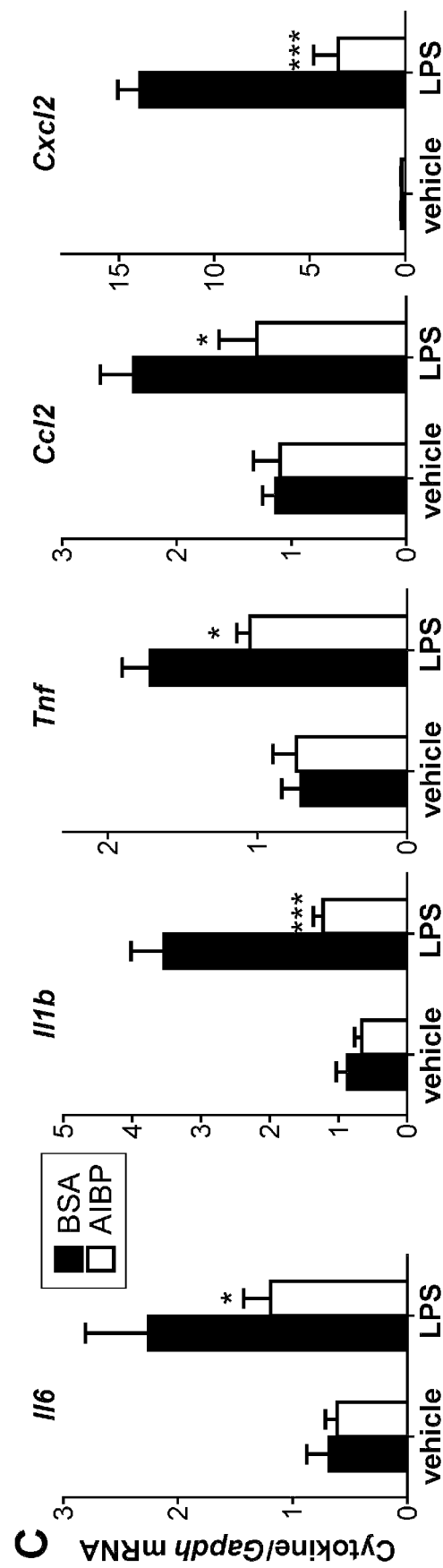
Figure 18D:
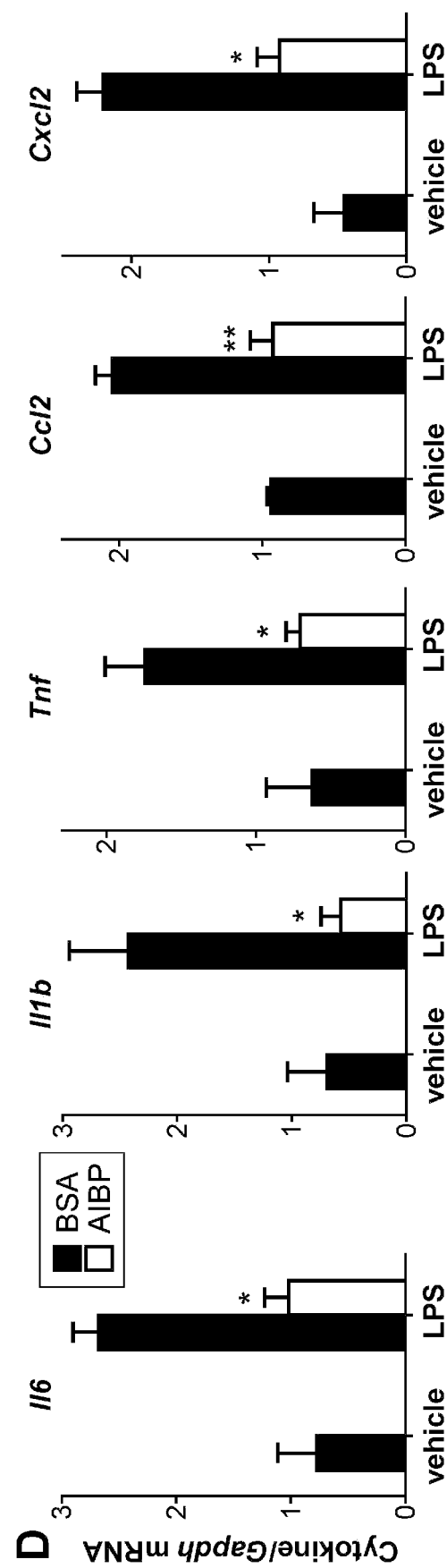

FIG. 18 schematically and graphically illustrates that AIBP reduces inflammatory responses in microglia. FIG. 18B-C graphically illustrate data where BV-2 microglia cells were incubated for 2 hours with vehicle (0.1% BSA) or 0.2 µg/ml AIBP (in 0.1% BSA) in serum-containing medium and stimulated with 10 ng/ml LPS. p65 and ERK1/2 phosphorylation were tested after 30 min (immunoblot illustrated in FIG. 18A, and results graphically illustrated in FIG. 18B), and cytokine mRNA expression after 2 h of incubation with LPS (FIG. 18C). FIG. 18D graphically illustrates data where primary mouse microglia (pooled from 5-6 mice per sample) were incubated for 2 hours with vehicle (0.1% BSA) or 0.2 µg/ml AIBP (in 0.1% BSA) in serum-containing medium and stimulated with 10 ng/ml LPS for 1 hour. Mean±SEM; n=4-6 for BV-2; n=3 for primary microglia experiments; *, p<0.05; , p<0.01; *, p<0.005 (Student's t-test).

Figure 19C:
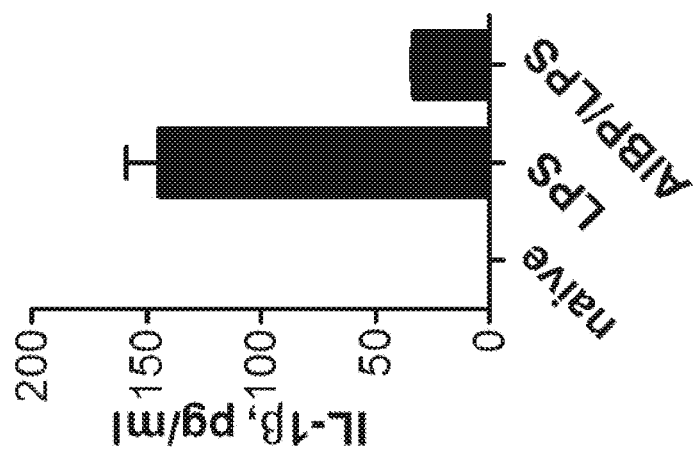
FIG. 19A-C graphically illustrate data showing that AIBP reduces neuroinflammation in the CNS, as discussed in detail in Example 3, below.
Figure 19B:
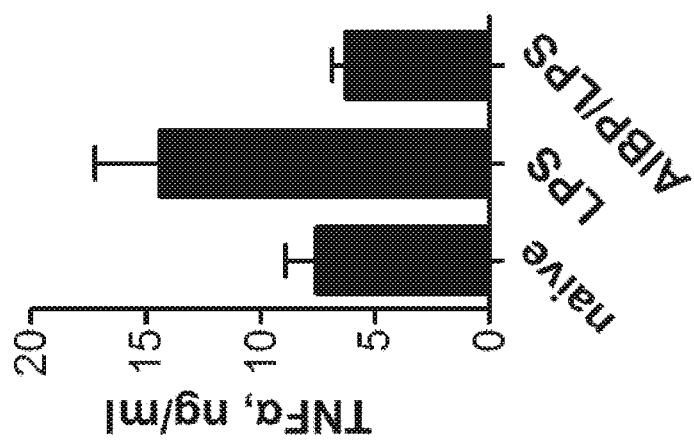
Figure 19A:
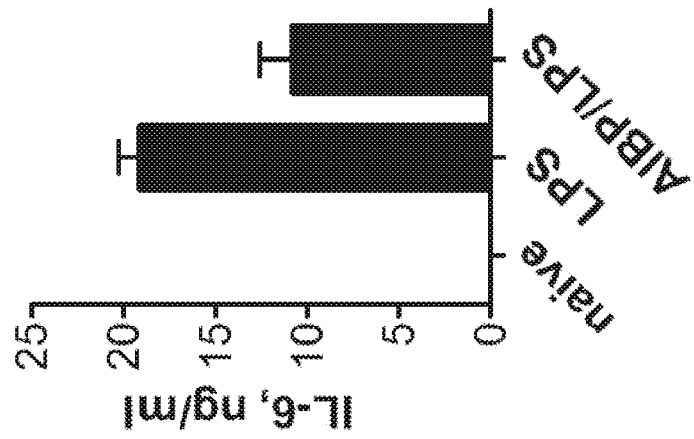

FIG. 19 graphically illustrates data showing that AIBP reduces neuroinflammation in the CNS. Male mice were given an i.t. injection of AIBP (0.5 µg/5 µl) or saline (5 µl); and two hours later, mice were given an i.t. injection of LPS (0.1 µg/5 µl). Four hours later, mice were sacrificed, cerebrospinal fluid (CSF) was collected and analyzed in ELISA to determine levels of inflammatory cytokines IL-1 (FIG. 19A), TNF-alpha (TNF-α) (FIG. 19B) and IL-1beta (IL-1β) (FIG. 19C). Pooled CSF samples from 4 mice in each group.

Thus, these data demonstrate that compositions and methods provided herein can be used to treat, prevent, decrease the severity of or ameliorate numerous pathological processes associated with pathologic lipid rafts and the occupancy of inflammatory receptors (TLR4) in lipid rafts, including neuroinflammation, Alzheimer's diseases (AD) and other neurodegenerative diseases or conditions. These include but not limited to γ-secretase cleavage of APP, apoE lipidation, and neuroinflammation [2-4]. Our studies of neuropathic pain have demonstrated that AIBP effectively reduces inflammatory responses in microglia (see e.g., FIG. 12 and discussion above) and that spinal delivery of AIBP reduces neuroinflammation in the CNS in the mouse model (FIG. 19).

Thus, we propose that raising AIBP levels in the CNS will prevent, delay and/or reverse the development of neurodegenerative diseases or conditions. AIBP can be delivered to the CNS via adeno-associated virus (AAV; see the accompanying document) or other CNS delivery methods, e.g., a CNS targeted vehicle capable of penetrating the blood brain barrier (BBB) as discussed above, such as e.g., with Clostridial neurotoxins-derived carriers for retroaxonal delivery of cargo proteins and genes to the brain [5].

Example 4: Efficacy Demonstrated in Exemplary Methods—AIBP Delivery to the CNS with AAV to Treat Neurodegeneration and Neurodegenerative Diseases This example describes and demonstrates the exemplary embodiment of delivery of AIBP to the CNS to e.g., treat, prevent, decrease the severity of or ameliorate neurodegeneration and/or neuroinflammation, including e.g., a neurodegenerative disease or condition such as Alzheimer's disease, chronic traumatic encephalopathy (CTE) or CNS or nerve damage due to trauma, such as traumatic brain injury (TBI).

The method of AIBP delivery used in preclinical (mouse) studies was: intrathecal injections of recombinant AIBP protein (29 kDa). In alternative embodiment, this AIBP is modified, e.g., by introducing mimetic peptides or other derivatives.

In alternative embodiments, AIPB is delivered to the CNS by intravenous (IV) injections of a large dose of AIBP or its derivatives designed to cross the blood-brain barrier. For example, in alternative embodiments, AIBP polypeptide, or AIBP encoding nucleic acid, e.g., nucleic acid contained in a vector, is carried in a nanoparticle, a particle, a micelle or a liposome or lipoplex, a polymersome, a polyplex or a dendrimer, which optionally can further comprise or express a cell penetrating moiety or peptide, and/or a CNS targeting moiety or peptide.

In one alternative embodiment, AIBP is delivered to the CNS using an adeno-associated virus (AAV); optionally, as a single dose (optionally a single dose of about $10^{10}$-$10^{14}$ gc/kg) of AAV, or multiple dosages of AAV, as needed, which will ensure sustained secretion of AIBP in the brain. In alternative embodiments, sufficient levels of individual dosages, or multiple administrations, are given to a patient in need thereof to achieve sustained levels of AIBP in the CNS, which can be advantageous in the treatment of a neurodegenerative disease or other chronic CNS condition.

For preclinical studies, we first made mouse AIBP-AAV. Specifically, we used commercially available AAV-DJ/8, which has been reported to preferentially infect CNS cells [1-3]. Similar strategy can be used to produce human AIBP-AAV for clinical applications, using other available or proprietary AAV constructs.

Virus Production and Testing

Figure 20:
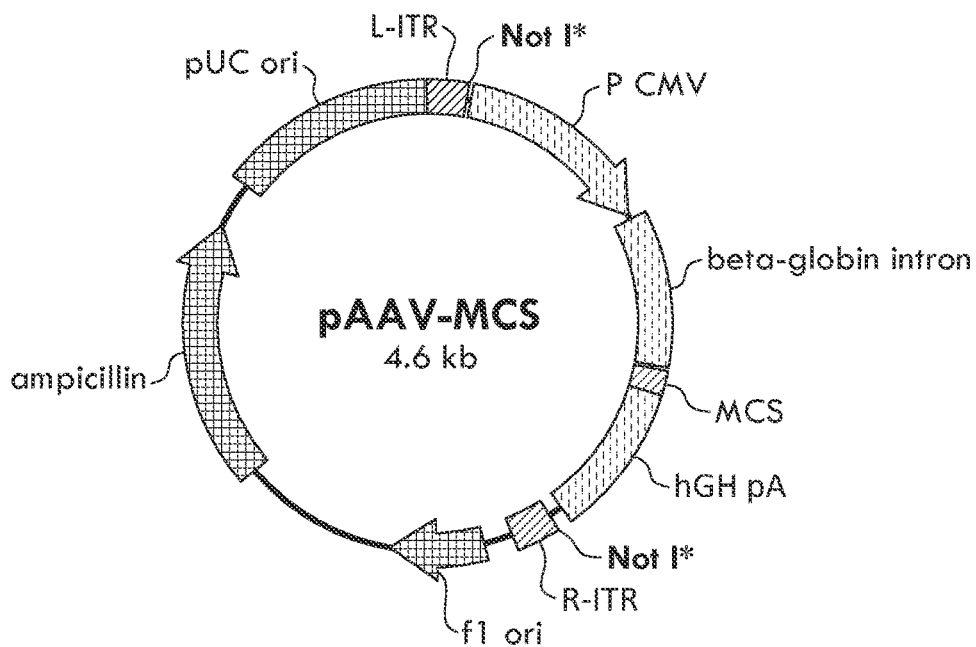
FIG. 20 schematically illustrates an AAV vector used to demonstrate AIBP delivery to the CNS, where the pAAV-MCS Multiple Cloning Site Region is SEQ ID NO:1; as discussed in detail in Example 4, below.

Mouse AIBP (24-863 aa) was fused with fibronectin secretion sequence (FIB) at the N-terminus and 6×-His at the C-terminus (FIB-mAIBP-His). FIB-mAIBP-His or FIB-GFP-His was cloned into the pAAV-MCS vector, as illustrated in FIG. 20. All clones were sequenced to confirm the presence of the insert.

AAV-293™ cells (Agilent Technologies) were transfected with 20 μg of each pAAV-FIB-mAIBP-His, pAAV-DJ/8 (Cell Biolabs), and pHelper™ DNA (Cell Biolabs) following the routine calcium phosphate-based protocol (Agilent Technologies). Subsequent steps of virus harvest, purification and storage were according to the manufacturer's protocol (Agilent Technologies).

Viral DNA was extracted from purified virus and the number of gene copies (gc) was determined using qPCR with primers for the inverted terminal repeats (ITRs).

Figure 21:
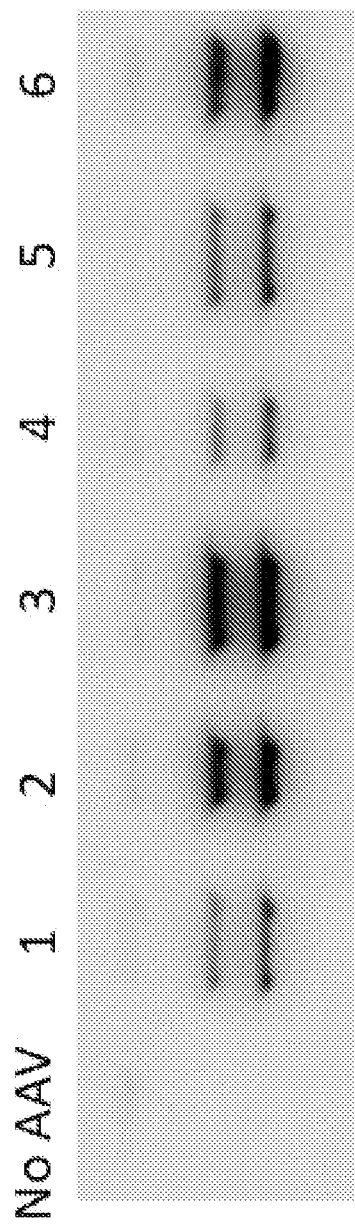
FIG. 21 illustrates an image of an immunoblot showing mAIBP expression in HEK293 cells infected with FIB-mAIBP-His-AAV-DJ/8; the blot was probed with an anti-His antibody, as discussed in detail in Example 4, below.

To test FIB-mAIBP-His-AAV-DJ/8, we infected HEK 293 cells. Three days later cells were harvested and mAIBP-His expression was confirmed in western blot with an anti-His antibody, as illustrated in FIG. 21: mAIBP expression in HEK293 cells infected with FIB-mAIBP-His-AAV-DJ/8. The blot was probed with an anti-His antibody. The two bands represent mAIBP with the fibronectin secretion sequence still attached (upper band) and mAIBP processed for secretion from which the fibronectin secretion signal was cleaved off (lower band). The cells were infected with $3.3\times10^{11}$ gc (sample 1), $6.6\times10^{11}$ gc (sample 1), $9.9\times10^{11}$ gc (sample 1), $2.2\times10^{11}$ gc (sample 1), $4.4\times10^{11}$ gc (sample 1), and $6.6\times10^{11}$ gc (sample 1), and analyzed 3 days later. Non-infected cells were used as a negative control.

SEQ ID NO:2 and SEQ ID NO:3 are the nucleotide and protein sequences, respectively, of murine AIBP supplemented with the fibronectin secretion signal (italic) at the N-terminus, and with the His tag (underlined) at the C-terminus; the product is abbreviated as FIB-mAIBP-His:

```
SEQ ID NO: 2:
ATG CTC AGG GGT CCG GGA CCC GGG CGG CTG CTG CTG

CTA GCA GTC CTG TGC CTG GGG ACA TCG GTG CGC TGC

ACC GAA ACC GGG AAG AGC AAG AGG
```

CAGCAGAGTGTGTCGTGCAAGGCCCATCTGGTGGGAACACAGCGCCG

GGGCTCGGAGACCATGGCGGGCGCTGCGGTGAAGTACTTAAGTCAGGAGG

AGGCTCAGGCCGTGGACCAAGAGCTTTTTAACGAGTATCAGTTCAGCGTG

GATCAACTCATGGAGCTGGCCGGGTTGAGCTGTGCCACGGCTATTGCCAA

GGCTTATCCCCCCACGTCTATGTCCAAGAGTCCCCCGACTGTCTTGGTCA

TCTGTGGCCCCGGAAATAACGGAGGGGATGGGCTGGTCTGTGCGCGACAC

CTCAAACTTTTTGGTTACCAGCCAACTATCTATTACCCCAAAAGACCTAA

CAAGCCCCTCTTCACTGGGCTAGTGACTCAGTGTCAGAAAATGGACATTC

CTTTCCTTGGTGAAATGCCCCCAGAGCCCATGATGGTGGACGAGCTGTAT

GAGCTGGTGGTGGACGCCATCTTCGGCTTCAGTTTCAAGGGTGACGTTCG

GGAGCCATTCCACAGCATCCTGAGTGTCTTGAGTGGACTCACTGTGCCCA

TTGCTAGCATCGACATTCCCTCAGGATGGGATGTAGAGAAGGGAAACCCT

AGCGGAATCCAACCAGACTTACTCATCTCACTGACGGCACCCAAGAAGTC

TGCAACTCACTTTACTGGCCGATATCATTACCTTGGGGGTCGCTTTGTAC

CACCTGCTCTAGAGAAGAAGTACCAGCTGAACCTGCCATCTTACCCTGAC

ACAGAGTGTGTCTACCGTCTACAG<u>CATCATCATCATCATCATTAA</u>

SEQ ID NO: 3:
*MLRGPGPGRLLLLAVLCLGTSVRCTETGKSKRQQSVCRARPIWWGTQRRG*

SETMAGAAVKYLSQEEAQAVDQELFNEYQFSVDQLMELAGLSCATAIAKA

YPPTSMSKSPPTVLVICGPGNNGGDGLVCARHLKLFGYQPTIYYPKRPNK

PLFTGLVTQCQKMDIPFLGEMPPEPMMVDELYELVVDAIFGFSFKGDVRE

PFHSILSVLSGLTVPIASIDIPSGWDVEKGNPSGIQPDLLISLTAPKKSA

THFTGRYHYLGGRFVPPALEKKYQLNLPSYPDTECVYRLQ<u>HHHHHH</u>

In alternative embodiment, human AIBP polypeptide, or a nucleic acid encoding an AIBP is administered to an individual in need thereof, or is used to manufacture a formulation or pharmaceutical, or is used to make a vector or expression vehicle for administration:

Human AIBP-encoding nucleic acid (cDNA)
(SEQ ID NO: 4)
GGGCCGGGCCGGGCCGGGGCGCGCGCTCTGCGAGCTGGATGTCCAGGCT

GCGGGCGCTGCTGGGCCTCGGGCTGCTGGTTGCGGGCTCGCGCGTGCCGC

GGATCAAAAGCCAGACCATCGCCTGTCGCTCGGGACCCACCTGGTGGGGA

CCGCAGCGGCTGAACTCGGGTGGCCGCTGGGACTCAGAGGTCATGGCGAG

CACGGTGGTGAAGTACCTGAGCCAGGAGGAGGCCCAGGCCGTGGACCAGG

AGCTATTTAACGAATACCAGTTCAGCGTGGACCAACTTATGGAACTGGCC

GGGCTGAGCTGTGCTACAGCCATCGCCAAGGCATATCCCCCCACGTCCAT

GTCCAGGAGCCCCCCTACTGTCCTGGTCATCTGTGGCCCGGGGAATAATG

GAGGAGATGGTCTGGTCTGTGCTCGACACCTCAAACTCTTTGGCTACGAG

CCAACCATCTATTACCCCAAAAGGCCTAACAAGCCCCTCTTCACTGCATT

GGTGACCCAGTGTCAGAAAATGGACATCCCTTTCCTTGGGGAAATGCCCG

CAGAGCCCATGACGATTGATGAACTGTATGAGCTGGTGGTGGATGCCATC

TTTGGCTTCAGCTTCAAGGGCGATGTTCGGGAACCGTTCCACAGCATCCT

GAGTGTCCTGAAGGGACTCACTGTGCCCATTGCCAGCATCGACATTCCCT

-continued
```
CAGGATGGGACGTGGAGAAGGGAAATGCTGGAGGGATCCAGCCAGACTTG

CTCATATCCCTCACAGCCCCCAAAAAATCTGCAACCCAGTTTACCGGTCG

CTACCATTACCTGGGGGGTCGTTTTGTGCCACCTGCTCTGGAGAAGAAGT

ACCAGCTGAACCTGCCACCCTACCCTGACACCGAGTGTGTCTATCGTCTG

CAGTGAGGGAAGGTGGGTGGGTATTCTTCCCAATAAAGACTTAGAGCCCC

TCTCTTCCAGAACTGTGGATTCCTGGGAGCTCCTCTGGCAATAAAAGTCA

GTGAATGGTGGAAGTCAGAGACCAACCCTGGGGATTGGGTGCCATCTCTC

TAGGGGTAACACAAAGGGCAAGAGGTTGCTATGGTATTTGGAAACAATGA

AAATGGACTGTTAGATGCCAA
```

Human AIBP polypeptide
(SEQ ID NO: 5)
```
MSRLRALLGLGLLVAGSRVPRIKSQTIACRSGPTWWGPQRLNSGGRWDSE

VMASTVVKYLSQEEAQAVDQELFNEYQFSVDQLMELAGLSCATAIAKAYP

PTSMSRSPPTVLVICGPGNNGGDGLVCARHLKLFGYEPTIYYPKRPNKPL

FTALVTQCQKMDIPFLGEMPAEPMTIDELYELVVDAIFGFSFKGDVREPF

HSILSVLKGLTVPIASIDIPSGWDVEKGNAGGIQPDLLISLTAPKKSATQ

FTGRYHYLGGRFVPPALEKKYQLNLPPYPDTECVYRLQ
```

In one embodiment, a secretion signal is added to ensure robust secretion of AIBP, for example, a fibronectin secretion signal is added to N terminus of AIBP (see italicized sequences in SEQ ID NO:2 and SEQ ID NO:3); or a nucleic acid encoding a secretion signal is added to the AIBP coding sequence. In alternative embodiments, a secretion signal is a fibronectin secretion signal, an immunoglobulin heavy chain secretion signal or an immunoglobulin kappa light chain secretory peptide (see, e.g., PLoS One. 2015; 10(2): e0116878), or an interleukin-2 signal peptide (see, e.g., J. Gene Med. 2005 March; 7(3):354-65).

In alternative embodiments, the polypeptide coding sequences are operatively linked to a promoter, e.g., a constitutive, inducible, tissue specific (e.g., nerve or brain tissue specific) or ubiquitous promoter or other transcriptional activating agent.

Example 5: Efficacy Demonstrated in Exemplary Methods—Intravenous (IV) Administration of AIBP Ameliorate Migraines This example describes and demonstrates, using an art-accepted animal (murine) model for migraines, the exemplary embodiment of delivery of AIBP for the treatment or amelioration of migraines.

Compound 48/80, a condensation product of N-methyl-p-methoxyphenethylamine with formaldehyde, promotes mast cells degranulation, release of histamine, and induces migraine-like light aversion in mice (Pain. 2007 July; 130 (1-2):166-76). This is tested in a housing unit with connected light and dark chambers, and time spent in each chamber is recorded. Unchallenged mice spend approximately 50% time in each chamber, but mice treated with compound 48/80 prefer the dark chamber for at least 2 hours, and then slowly recover.

Figure 22:
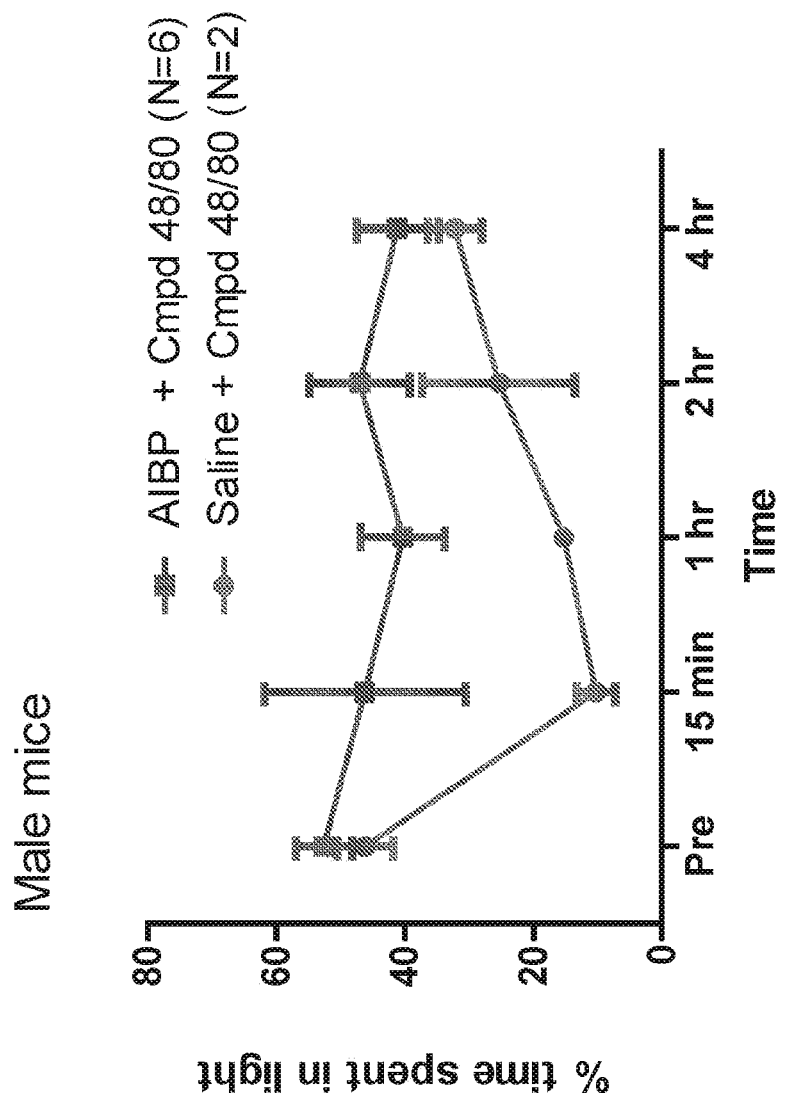
FIG. 22 graphically illustrates that intravenous AIBP reduces light aversion (measure of migraine) in male mice injected with Compound 48/80, as discussed in detail in Example 5, below.
Figure 23:
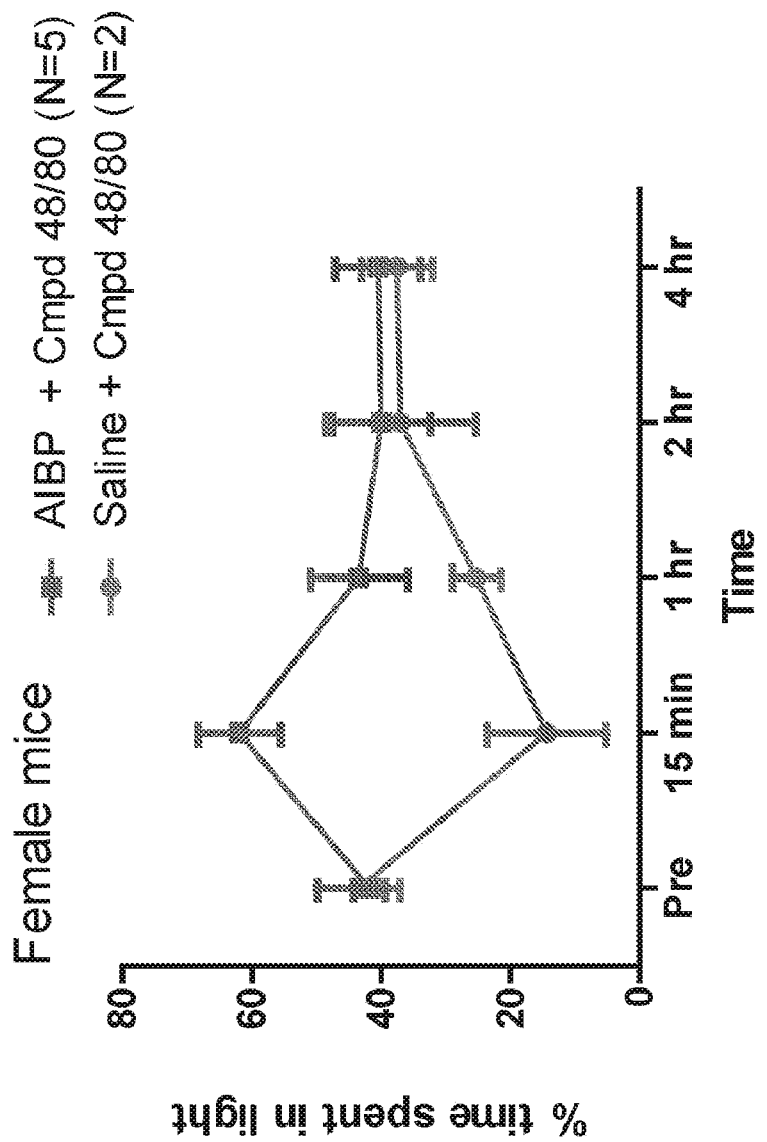
FIG. 23 graphically illustrates that intravenous AIBP reduces light aversion (measure of migraine) in female mice injected with Compound 48/80, as discussed in detail in Example 5, below.

Male and female mice were injected i.v. with AIBP (0.5 µg/100 µl) or saline (100 µl) 2 hours prior to i.p. injection of compound 48/80 (2 mg/kg). AIBP-injected mice did not develop light aversion (FIGS. 22 and 23), thus demonstrating the efficacy administration of AIBP for the treatment or amelioration of migraines.

References—Example 1
1. Committee on Advancing Pain Research Care and Education. Relieving Pain in America: A Blueprint for Transforming Prevention, Care, Education, and Research. *The National Academies Collection: New Releases.*, Washington, D.C., National Academies Press. 2011
2. Pergolizzi J, Boger R H, Budd K, Dahan A, Erdine S, Hans G, Kress H G, Langford R, Likar R, Raffa R B, Sacerdote P. Opioids and the management of chronic severe pain in the elderly: consensus statement of an International Expert Panel with focus on the six clinically most often used World Health Organization Step III opioids (buprenorphine, fentanyl, hydromorphone, methadone, morphine, oxycodone). *Pain Pract.* 2008; 8:287-313
3. Schug S A, Goddard C. Recent advances in the pharmacological management of acute and chronic pain. *Ann Palliat Med.* 2014; 3:263-275
4. Tauben D. Nonopioid Medications for Pain. *Phys Med Rehabil Clin N Am.* 2015; 26:219-248
5. Rosenblum A, Marsch L A, Joseph H, Portenoy R K. Opioids and the treatment of chronic pain: controversies, current status, and future directions. *Exp Clin Psychopharmacol.* 2008; 16:405-416
6. Straube S, Derry S, Moore R A, Paine J, McQuay H J. Pregabalin in fibromyalgia—responder analysis from individual patient data. *BMC Musculoskelet Disord.* 2010; 11:150
7. Xu Q, Yaksh T L. A brief comparison of the pathophysiology of inflammatory versus neuropathic pain. *Curr Opin Anaesthesiol.* 2011; 24:400-407
8. Katz J, Seltzer Z. Transition from acute to chronic postsurgical pain: risk factors and protective factors. *Expert Rev Neurother.* 2009; 9:723-744
9. Kehlet H, Rathmell J P. Persistent postsurgical pain: the path forward through better design of clinical studies. *Anesthesiology.* 2010; 112:514-515
10. Wolfe F, Michaud K. Assessment of pain in rheumatoid arthritis: minimal clinically significant difference, predictors, and the effect of anti-tumor necrosis factor therapy. *J Rheumatol.* 2007; 34:1674-1683
11. Taylor P, Manger B, Alvaro-Gracia J, Johnstone R, Gomez-Reino J, Eberhardt E, Wolfe F, Schwartzman S, Furfaro N, Kavanaugh A. Patient perceptions concerning pain management in the treatment of rheumatoid arthritis. *J Int Med Res.* 2010; 38:1213-1224
12. Poltorak A, He X, Smirnova I, Liu M Y, Huffel C V, Du X, Birdwell D, Alejos E, Silva M, Galanos C, Freudenberg M, Ricciardi-Castagnoli P, Layton B, Beutler B. Defective LPS Signaling in C3H/HeJ and C57BL/10ScCr Mice: Mutations in Tlr4 Gene. *Science.* 1998; 282:2085-2088
13. Christianson C A, Dumlao D S, Stokes J A, Dennis E A, Svensson C I, Corr M, Yaksh T L. Spinal TLR4 mediates the transition to a persistent mechanical hypersensitivity after the resolution of inflammation in serum-transferred arthritis. *Pain.* 2011; 152:2881-2891
14. Cao L, Tanga F Y, Deleo J A. The contributing role of CD14 in toll-like receptor 4 dependent neuropathic pain. *Neuroscience.* 2009; 158:896-903
15. Sorge R E, LaCroix-Fralish M L, Tuttle A H, Sotocinal S G, Austin J S, Ritchie J, Chanda M L, Graham A C, Topham L, Beggs S, Salter M W, Mogil J S. Spinal cord Toll-like receptor 4 mediates inflammatory and neuropathic hypersensitivity in male but not female mice. *J Neurosci.* 2011; 31:15450-15454

16. Stokes J A, Cheung J, Eddinger K, Corr M, Yaksh T L. Toll-like receptor signaling adapter proteins govern spread of neuropathic pain and recovery following nerve injury in male mice. *J Neuroinflammation.* 2013; 10:148
17. Woller S A, Con M, Yaksh T L. Differences in cisplatin-induced mechanical allodynia in male and female mice. *Eur J Pain.* 2015
18. Park H J, Stokes J A, Corr M, Yaksh T L. Toll-like receptor signaling regulates cisplatin-induced mechanical allodynia in mice. *Cancer Chemother Pharmacol.* 2014; 73:25-34
19. White C R, Smythies L E, Crossman D K, Palgunachari M N, Anantharamaiah G M, Datta G. Regulation of pattern recognition receptors by the apolipoprotein A-I mimetic peptide 4F. *Arterioscler Thromb Vasc Biol.* 2012; 32:2631-2639
20. Villacorta L, Chang L, Salvatore S R, Ichikawa T, Zhang J, Petrovic-Djergovic D, Jia L, Carlsen H, Schopfer F J, Freeman B A, Chen Y E. Electrophilic nitro-fatty acids inhibit vascular inflammation by disrupting LPS-dependent TLR4 signalling in lipid rafts. *Cardiovasc Res.* 2013; 98:116-124
21. D'Alessio A, Kluger M S, Li J H, Al-Lamki R, Bradley J R, Pober J S. Targeting of tumor necrosis factor receptor 1 to low density plasma membrane domains in human endothelial cells. *J Biol Chem.* 2010; 285:23868-23879
22. Levitan I, Shentu T-P. Impact of oxLDL on Cholesterol-Rich Membrane Rafts. *Journal of Lipids.* 2011; 2011
23. Schmitz G, Orso E. CD14 signalling in lipid rafts: new ligands and co-receptors. *Curr Opin Lipidol.* 2002; 13:513-521
24. Triantafilou M, Triantafilou K. Membrane partitioning: is location everything when it comes to endotoxin recognition? *Subcell. Biochem.* 2010; 53:173-184
25. Fessler M B, Parks J S. Intracellular lipid flux and membrane microdomains as organizing principles in inflammatory cell signaling. *J Immunol.* 2011; 187:1529-1535
26. Meng G, Liu Y, Lou C, Yang H. Emodin suppresses lipopolysaccharide-induced pro-inflammatory responses and NF-kappaB activation by disrupting lipid rafts in CD14-negative endothelial cells. *Br J Pharmacol.* 2010; 161:1628-1644
27. Shridas P, Bailey W M, Talbott K R, Oslund R C, Gelb M H, Webb N R. Group X secretory phospholipase A2 enhances TLR4 signaling in macrophages. *J Immunol.* 2011; 187:482-489
28. Ottinger E A, Kao M L, Carrillo-Carrasco N, Yanjanin N, Shankar R K, Janssen M, Brewster M, Scott I, Xu X, Cradock J, Terse P, Dehdashti S J, Marugan J, Zheng W, Portilla L, Hubbs A, Pavan W J, Heiss J, C H V, Walkley S U, Ory D S, Silber S A, Porter F D, Austin C P, McKew J C. Collaborative development of 2-hydroxypropyl-beta-cyclodextrin for the treatment of Niemann-Pick type C1 disease. *Curr Top Med Chem.* 2014; 14:330-339
29. Lopez A M, Terpack S J, Posey K S, Liu B, Ramirez C M, Turley S D. Systemic administration of 2-hydroxypropyl-beta-cyclodextrin to symptomatic Npc1-deficient mice slows cholesterol sequestration in the major organs and improves liver function. *Clin Exp Pharmacol Physiol.* 2014; 41:780-787
30. Tortelli B, Fujiwara H, Bagel J H, Zhang J, Sidhu R, Jiang X, Yanjanin N M, Shankar R K, Carillo-Carasco N, Heiss J, Ottinger E, Porter F D, Schaffer J E, Vite C H, Ory D S. Cholesterol homeostatic responses provide biomarkers for monitoring treatment for the neurodegenerative disease Niemann-Pick C1 (NPC1). *Hum Mol Genet.* 2014; 23:6022-6033
31. Vance J E, Karten B. Niemann-Pick C disease and mobilization of lysosomal cholesterol by cyclodextrin. *J Lipid Res.* 2014; 55:1609-1621
32. Bodzioch M, Orso E, Klucken J, Langmann T, Bottcher A, Diederich W, Drobnik W, Barlage S, Buchler C, Porsch-Ozcurumez M, Kaminski W E, Hahmann H W, Oette K, Rothe G, Aslanidis C, Lackner K J, Schmitz G. The gene encoding ATP-binding cassette transporter 1 is mutated in Tangier disease. *Nat Genet.* 1999; 22:347-351
33. Rust S, Rosier M, Funke H, Real J, Amoura Z, Piette J C, Deleuze J F, Brewer H B, Duverger N, Denefle P, Assmann G. Tangier disease is caused by mutations in the gene encoding ATP-binding cassette transporter 1. *Nat Genet.* 1999; 22:352-355
34. Klucken J, Buchler C, Orso E, Kaminski W E, Porsch-Ozcurumez M, Liebisch G, Kapinsky M, Diederich W, Drobnik W, Dean M, Allikmets R, Schmitz G. ABCG1 (ABC8), the human homolog of the *Drosophila* white gene, is a regulator of macrophage cholesterol and phospholipid transport. *Proc Natl Acad. Sci U.S.A.* 2000; 97:817-822
35. Yvan-Charvet L, Welch C, Pagler T A, Ranalletta M, Lamkanfi M, Han S, Ishibashi M, Li R, Wang N, Tall A R. Increased inflammatory gene expression in ABC transporter-deficient macrophages: free cholesterol accumulation, increased signaling via toll-like receptors, and neutrophil infiltration of atherosclerotic lesions. *Circulation.* 2008; 118:1837-1847
36. Sun Y, Ishibashi M, Seimon T, Lee M, Sharma S M, Fitzgerald K A, Samokhin A O, Wang Y, Sayers S, Aikawa M, Jerome W G, Ostrowski M C, Bromme D, Libby P, Tabas I A, Welch C L, Tall A R. Free Cholesterol Accumulation in Macrophage Membranes Activates Toll-Like Receptors and p38 Mitogen-Activated Protein Kinase and Induces Cathepsin K. *Circ Res.* 2009; 104:455-465
37. Mineo C, Shaul P W. Regulation of signal transduction by HDL. *J Lipid Res.* 2013; 54:2315-2324
38. Terasaka N, Yu S, Yvan-Charvet L, Wang N, Mzhavia N, Langlois R, Pagler T, Li R, Welch C L, Goldberg I J, Tall A R. ABCG1 and HDL protect against endothelial dysfunction in mice fed a high-cholesterol diet. *The Journal of Clinical Investigation.* 2008; 118:3701-3713
39. van der Westhuyzen D R, de Beer F C, Webb N R. HDL cholesterol transport during inflammation. *Curr. Opin. Lipidol.* 2007; 18:147-151
40. Murphy A J, Woollard K J, Hoang A, Mukhamedova N, Stirzaker R A, McCormick S P A, Remaley A T, Sviridov D, Chin-Dusting J. High-Density Lipoprotein Reduces the Human Monocyte Inflammatory Response. *Arterioscler Thromb Vasc Biol.* 2008; 28:2071-2077
41. Muller C, Salvayre R, Negre-Salvayre A, Vindis C. HDLs inhibit endoplasmic reticulum stress and autophagic response induced by oxidized LDLs. *Cell Death Differ.* 2011; 18:817-828
42. Zheng C, Aikawa M. High-Density Lipoproteins: From Function to Therapy. *J Am Coll Cardiol.* 2012; 60:2380-2383
43. Vitali C, Wellington C L, Calabresi L. HDL and cholesterol handling in the brain. *Cardiovasc Res.* 2014; 103:405-413
44. Elliott D A, Weickert C S, Garner B. Apolipoproteins in the brain: implications for neurological and psychiatric disorders. *Clin Lipidol.* 2010; 51:555-573

45. Louveau A, Smirnov I, Keyes T J, Eccles J D, Rouhani S J, Peske J D, Derecki N C, Castle D, Mandell J W, Lee K S, Harris T H, Kipnis J. Structural and functional features of central nervous system lymphatic vessels. *Nature.* 2015; advance online publication 46. Aspelund A, Antila S, Proulx S T, Karlsen T V, Karaman S, Detmar M, Wiig H, Alitalo K. A dural lymphatic vascular system that drains brain interstitial fluid and macromolecules. *The Journal of Experimental Medicine.* 2015

47. Martel C, Li W, Fulp B, Platt A M, Gautier E L, Westerterp M, Bittman R, Tall A R, Chen S H, Thomas M J, Kreisel D, Swartz M A, Sorci-Thomas M G, Randolph G J. Lymphatic vasculature mediates macrophage reverse cholesterol transport in mice. *The Journal of Clinical Investigation.* 2013; 123:1571-1579

48. Hobbs H H, Rader D J. ABC1: connecting yellow tonsils, neuropathy, and very low HDL. *J Clin Invest.* 1999; 104:1015-1017

49. van Exel E, de Craen A J, Gussekloo J, Houx P, Bootsma-van der Wiel A, Macfarlane P W, Blauw G J, Westendorp R G. Association between high-density lipoprotein and cognitive impairment in the oldest old. *Ann Neurol.* 2002; 51:716-721

50. Merched A, Xia Y, Visvikis S, Serot J M, Siest G. Decreased high-density lipoprotein cholesterol and serum apolipoprotein A I concentrations are highly correlated with the severity of Alzheimer's disease. *Neurobiol Aging.* 2000; 21:27-30

51. Singh-Manoux A, Gimeno D, Kivimaki M, Brunner E, Marmot M G. Low HDL cholesterol is a risk factor for deficit and decline in memory in midlife: the Whitehall II study. *Arterioscler Thromb Vasc Biol.* 2008; 28:1556-1562

52. Reitz C, Tang M X, Schupf N, Manly J J, Mayeux R, Luchsinger J A. Association of higher levels of high-density lipoprotein cholesterol in elderly individuals and lower risk of late-onset Alzheimer disease. *Arch Neurol.* 2010; 67:1491-1497

53. Ritter M, Buechler C, Boettcher A, Barlage S, Schmitz-Madry A, Orso E, Bared S M, Schmiedeknecht G, Baehr C H, Fricker G, Schmitz G. Cloning and characterization of a novel apolipoprotein A-I binding protein, AI-BP, secreted by cells of the kidney proximal tubules in response to HDL or ApoA-I. *Genomics.* 2002; 79:693-702

54. Jha K N, Shumilin I A, Digilio L C, Chertihin O, Zheng H, Schmitz G, Visconti P E, Flickinger C J, Minor W, Herr J C. Biochemical and structural characterization of apolipoprotein A-I binding protein, a novel phosphoprotein with a potential role in sperm capacitation. *Endocrinology.* 2008; 149:2108-2120

55. Rudolph C, Sigruener A, Hartmann A, Orso E, Bals-Pratsch M, Gronwald W, Seifert B, Kalbitzer H R, Verdorfer I, Luetjens C M, Ortmann O, Bornstein S R, Schmitz G. ApoA-I-binding protein (AI-BP) and its homologues hYjeF_N2 and hYjeF_N3 comprise the YjeF_N domain protein family in humans with a role in spermiogenesis and oogenesis. *Horm. Metab Res.* 2007; 39:322-335

56. Marbaix A Y, Noel G, Detroux A M, Vertommen D, Van Schaftingen E, Linster C L. Extremely Conserved ATP- or ADP-dependent Enzymatic System for Nicotinamide Nucleotide Repair. *J Biol Chem.* 2011; 286:41246-41252

57. Shumilin Igor A, Cymborowski M, Chertihin O, Jha Kula N, Herr John C, Lesley Scott A, Joachimiak A, Minor W. Identification of Unknown Protein Function Using Metabolite Cocktail Screening. *Structure.* 2012; 20:1715-1725

58. Fang L, Choi S H, Baek J S, Liu C, Almazan F, Ulrich F, Wiesner P, Taleb A, Deer E, Pattison J, Torres-Vazquez J, Li A C, Miller Y I. Control of angiogenesis by AIBP-mediated cholesterol efflux. *Nature.* 2013; 498:118-122

59. Saito O, Svensson C I, Buczynski M W, Wegner K, Hua X Y, Codeluppi S, Schaloske R H, Deems R A, Dennis E A, Yaksh T L. Spinal glial TLR4-mediated nociception and production of prostaglandin E(2) and TNF. *Br J Pharmacol.* 2010; 160:1754-1764

60. Stokes J A, Con M, Yaksh T L. Spinal toll-like receptor signaling and nociceptive processing: regulatory balance between TIRAP and TRIF cascades mediated by TNF and IFNbeta. *Pain.* 2013; 154:733-742

61. Triantafilou M, Miyake K, Golenbock D T, Triantafilou K. Mediators of innate immune recognition of bacteria concentrate in lipid rafts and facilitate lipopolysaccharide-induced cell activation. *J Cell Sci.* 2002; 115:2603-2611

62. Olsson S, Sundler R. The role of lipid rafts in LPS-induced signaling in a macrophage cell line. *Mol Immunol.* 2006; 43:607-612

63. Fernandez-Lizarbe S, Pascual M, Gascon M S, Blanco A, Guerri C. Lipid rafts regulate ethanol-induced activation of TLR4 signaling in murine macrophages. *Mol Immunol.* 2008; 45:2007-2016

64. Mogilenko D A, Orlov S V, Trulioff A S, Ivanov A V, Nagumanov V K, Kudriavtsev I V, Shavva V S, Tanyanskiy D A, Perevozchikov A P. Endogenous apolipoprotein A-I stabilizes ATP-binding cassette transporter A1 and modulates Toll-like receptor 4 signaling in human macrophages. *The FASEB Journal.* 2012; 26:2019-2030

65. Wu Y, Willcockson H H, Maixner W, Light A R. Suramin inhibits spinal cord microglia activation and long-term hyperalgesia induced by formalin injection. *J Pain.* 2004; 5:48-55

References—Example 2—Materials and Methods

1. Gosselin D, et al. Environment drives selection and function of enhancers controlling tissue-specific macrophage identities. *Cell.* 2014; 159(6):1327-40.

2. Blasi E, et al. Immortalization of murine microglial cells by a v-raf/v-myc carrying retrovirus. *J Neuroimmunol.* 1990; 27(2-3):229-37.

3. Saitoh S-i, et al. Lipid A antagonist, lipid IVa, is distinct from lipid A in interaction with Toll-like receptor 4 (TLR4)-MD-2 and ligand-induced TLR4 oligomerization. *Int Immunol.* 2004; 16(7):961-9.

4. Wong S W, et al. Fatty Acids Modulate Toll-like Receptor 4 Activation through Regulation of Receptor Dimerization and Recruitment into Lipid Rafts in a Reactive Oxygen Species-dependent Manner. *J Biol Chem.* 2009; 284(40):27384-92.

5. Park H S, et al. Cutting edge: direct interaction of TLR4 with NAD(P)H oxidase 4 isozyme is essential for lipopolysaccharide-induced production of reactive oxygen species and activation of NF-kappa B. *J Immunol.* 2004; 173(6):3589-93.

6. Fang L, et al. Control of angiogenesis by AIBP-mediated cholesterol efflux. *Nature.* 2013; 498(7452):118-22.

7. Choi S H, et al. Spleen Tyrosine Kinase Regulates AP-1 Dependent Transcriptional Response to Minimally Oxidized LDL. *PLoS One.* 2012; 7(2):e32378.

8. Raetz C R H, et al. Kdo2-Lipid A of *Escherichia coli*, a defined endotoxin that activates macrophages via TLR-4. *J Lipid Res.* 2006; 47(5):1097-111.

9. Woller S A, et al. Systemic TAK-242 prevents intrathecal LPS evoked hyperalgesia in male, but not female mice and prevents delayed allodynia following intraplantar formalin in both male and female mice: The role of TLR4 in the evolution of a persistent pain state. *Brain Behav Immun.* 2016.

10. Sorge R E, et al. Olfactory exposure to males, including men, causes stress and related analgesia in rodents. *Nat Meth.* 2014; 11(6):629-32.

11. Chaplan S R, et al. Quantitative assessment of tactile allodynia in the rat paw. *J Neurosci Methods.* 1994; 53(1):55-63.

12. Yaksh T L, et al. An automated flinch detecting system for use in the formalin nociceptive bioassay. *Journal of applied physiology (Bethesda, Md.: 1985).* 2001; 90(6):2386-402.

References—Example 2—Results and Discussion

1. Hutchinson M R, et al. Evidence for a role of heat shock protein-90 in toll like receptor 4 mediated pain enhancement in rats. *Neuroscience.* 2009; 164(4):1821-32.

2. Miller R E, et al. Damage-associated molecular patterns generated in osteoarthritis directly excite murine nociceptive neurons through Toll-like receptor 4. *Arthritis Rheumatol.* 2015; 67(11):2933-43.

3. Shibasaki M, et al. Induction of high mobility group box-1 in dorsal root ganglion contributes to pain hypersensitivity after peripheral nerve injury. *Pain.* 2010; 149(3):514-21.

4. Agalave N M, and Svensson C I. Extracellular High-Mobility Group Box 1 Protein (HMGB1) as a Mediator of Persistent Pain. *Mol Med.* 2015; 20(1):569-78.

5. Poltorak A, et al. Defective LPS Signaling in C3H/HeJ and C57BL/10ScCr Mice: Mutations in Tlr4 Gene. *Science.* 1998; 282(5396):2085-8.

6. Christianson C A, et al. Spinal TLR4 mediates the transition to a persistent mechanical hypersensitivity after the resolution of inflammation in serum-transferred arthritis. *Pain.* 2011; 152(12):2881-91.

7. Cao L, et al. The contributing role of CD14 in toll-like receptor 4 dependent neuropathic pain. *Neuroscience.* 2009; 158(2):896-903.

8. Sorge R E, et al. Spinal cord Toll-like receptor 4 mediates inflammatory and neuropathic hypersensitivity in male but not female mice. *J Neurosci.* 2011; 31(43):15450-4.

9. Stokes J A, et al. Toll-like receptor signaling adapter proteins govern spread of neuropathic pain and recovery following nerve injury in male mice. *J Neuroinflam.* 2013; 10(148.

10. Woller S A, et al. Differences in cisplatin-induced mechanical allodynia in male and female mice. *Eur J Pain.* 2015.

11. Park H J, et al. Toll-like receptor signaling regulates cisplatin-induced mechanical allodynia in mice. *Cancer Chemother Pharmacol.* 2014; 73(1):25-34.

12. Schmitz G, and Orso E. CD14 signalling in lipid rafts: new ligands and co-receptors. *Curr Opin Lipidol.* 2002; 13(5):513-21.

13. Triantafilou M, et al. Mediators of innate immune recognition of bacteria concentrate in lipid rafts and facilitate lipopolysaccharide-induced cell activation. *J Cell Sci.* 2002; 115(Pt 12):2603-11.

14. Fessler M B, and Parks J S. Intracellular lipid flux and membrane microdomains as organizing principles in inflammatory cell signaling. *J Immunol.* 2011; 187(4):1529-35.

15. Tall A R, and Yvan-Charvet L. Cholesterol, inflammation and innate immunity. *Nat Rev Immunol.* 2015; 15(2):104-16.

16. Ritter M, et al. Cloning and characterization of a novel apolipoprotein A-I binding protein, AI-BP, secreted by cells of the kidney proximal tubules in response to HDL or ApoA-I. *Genomics.* 2002; 79(5):693-702.

17. Fang L, et al. Control of angiogenesis by AIBP-mediated cholesterol efflux. *Nature.* 2013; 498(7452):118-22.

18. Saito O, et al. Spinal glial TLR4-mediated nociception and production of prostaglandin E(2) and TNF. *Br J Pharmacol.* 2010; 160(7):1754-64.

19. Stokes J A, et al. Spinal toll-like receptor signaling and nociceptive processing: regulatory balance between TIRAP and TRIF cascades mediated by TNF and IFN-beta. *Pain.* 2013; 154(5):733-42.

20. Sun Y, et al. The over-production of TNF-alpha via Toll-like receptor 4 in spinal dorsal horn contributes to the chronic postsurgical pain in rat. *J Anesth.* 2015; 29(5):734-40.

21. Wong S W, et al. Fatty Acids Modulate Toll-like Receptor 4 Activation through Regulation of Receptor Dimerization and Recruitment into Lipid Rafts in a Reactive Oxygen Species-dependent Manner. *J Biol Chem.* 2009; 284(40):27384-92.

22. Woller S A, et al. Systemic TAK-242 prevents intrathecal LPS evoked hyperalgesia in male, but not female mice and prevents delayed allodynia following intraplantar formalin in both male and female mice: The role of TLR4 in the evolution of a persistent pain state. *Brain Behav Immun.* 2016; 56:271-80.

23. Meng G, et al. Emodin suppresses lipopolysaccharide-induced pro-inflammatory responses and NF-kappaB activation by disrupting lipid rafts in CD14-negative endothelial cells. *Br J Pharmacol.* 2010; 161(7):1628-44.

24. Shridas P, et al. Group X secretory phospholipase A2 enhances TLR4 signaling in macrophages. *J Immunol.* 2011; 187(1):482-9.

25. Penning J P, and Yaksh T L. Interaction of intrathecal morphine with bupivacaine and lidocaine in the rat. *Anesthesiology.* 1992; 77(6):1186-2000.

26. Huang P P, et al. Spinal botulinum neurotoxin B: effects on afferent transmitter release and nociceptive processing. *PLoS One.* 2011; 6(4):e19126.

27. Wu Y, et al. Suramin inhibits spinal cord microglia activation and long-term hyperalgesia induced by formalin injection. *J Pain.* 2004; 5(1):48-55.

28. Wolf S, et al. Chemotherapy-induced peripheral neuropathy: prevention and treatment strategies. *Eur J Cancer.* 2008; 44(11):1507-15.

29. Smith E M, et al. Predictors of duloxetine response in patients with oxaliplatin-induced painful chemotherapy-induced peripheral neuropathy (CIPN): a secondary analysis of randomised controlled trial—CALGB/alliance 170601. *Eur J Cancer Care (Engl).* 2015.

30. Park H J. Chemotherapy induced peripheral neuropathic pain. *Korean J Anesthesiol.* 2014; 67(1):4-7.

31. Yaksh T L. *Fundamental Neuropathology for Pathologists and Toxicologists.* John Wiley & Sons, Inc.; 2011: 449-62.

32. Calias P, et al. Intrathecal delivery of protein therapeutics to the brain: a critical reassessment. *Pharmacol Ther.* 2014; 144(2):114-22.

33. Sanford M. Intrathecal ziconotide: a review of its use in patients with chronic pain refractory to other systemic or intrathecal analgesics. *CNS drugs.* 2013; 27(11):989-1002.

References—Example 3

1. Fang, L. et al. (2013) Control of angiogenesis by AIBP-mediated cholesterol efflux. *Nature* 498 (7452), 118-122.
2. Araki, W. and Tamaoka, A. (2015) Amyloid beta-protein and lipid rafts: focused on biogenesis and catabolism. Front Biosci (Landmark Ed) 20, 314-24.
3. Boehm-Cagan, A. and Michaelson, D. M. (2014) Reversal of apoE4-driven brain pathology and behavioral deficits by bexarotene. *J Neurosci* 34 (21), 7293-301.
4. Tai, L. M. et al. (2015) APOE-modulated Abeta-induced neuroinflammation in Alzheimer's disease: current landscape, novel data, and future perspective. *J Neurochem* 133 (4), 465-88.
5. Ovsepian, S. V. et al. (2016) Circumventing Brain Barriers: Nanovehicles for Retroaxonal Therapeutic Delivery. *Trends Mol Med* 22 (11), 983-993.

References—Example 4

1. Grimm, D. et al. (2008) In vitro and in vivo gene therapy vector evolution via multispecies interbreeding and retargeting of adeno-associated viruses. *J Virol* 82 (12), 5887-911.
2. Saraiva, J. et al. (2016) Gene therapy for the CNS using AAVs: The impact of systemic delivery by AAV9. *J Control Release* 241, 94-109.
3. Iwata, R. et al. (2015) Developmental RacGAP alpha2-Chimaerin Signaling Is a Determinant of the Morphological Features of Dendritic Spines in Adulthood. *J Neurosci* 35 (40), 13728-44.

34. Yaksh T L, et al. Current and Future Issues in the development of spinal agents for the management of pain. *Curr Neuropharmacol.* 2016. Published ahead of print. PubMed PMID: 26861470.

A number of embodiments of the invention have been described. Nevertheless, it will be understood that various modifications may be made without departing from the spirit and scope of the invention. Accordingly, other embodiments are within the scope of the following claims.

What is claimed is:

1. A method for treating, ameliorating, reversing or decreasing the severity or duration of a primary headache, wherein the method comprises:
   (a) providing or having provided a formulation or a pharmaceutical composition comprising: an ApoA-I Binding Protein (APOA1BP) polypeptide compound or composition; and
   (b) administering or having administered the formulation or the pharmaceutical composition of (a) to a subject in need thereof, thereby treating, ameliorating, reversing or decreasing the severity or duration of the primary headache, or
   (b) administering the formulation or the pharmaceutical composition comprising: an ApoA-I Binding Protein (APOA1BP) polypeptide compound or composition to a subject in need thereof, thereby treating, ameliorating, reversing or decreasing the severity or duration of the primary headache.

2. The method of claim 1, wherein the primary headache is a migraine.

3. The method of claim 1, wherein the primary headache is a cluster headache.

4. The method of claim 1, wherein the ApoA-I Binding Protein (APOA1BP) polypeptide is a mammalian APOA1BP polypeptide.

5. The method of claim 4, wherein the ApoA-I Binding Protein (APOA1BP) polypeptide is a human APOA1BP polypeptide.

6. The method of claim 1, wherein the subject is a human.

7. The method of claim 1, wherein the subject is an animal.

8. The method of claim 1, wherein the APOA1BP polypeptide is a recombinant APOA1BP polypeptide.

9. The method of claim 1, wherein the APOA1BP polypeptide is a synthetic APOA1BP polypeptide.

10. The method of claim 1, wherein the formulation or pharmaceutical composition is formulated for administration in vivo; or is formulated for enteral or parenteral administration.

11. The method of claim 1, wherein the formulation or pharmaceutical composition is formulated for administration by in vivo intrathecal injection.

12. The method of claim 1, wherein the formulation or pharmaceutical composition is formulated for oral administration.

13. The method of claim 1, wherein the formulation or pharmaceutical composition is formulated for intravenous (IV) administration.

14. The method of claim 1, wherein the APOA1BP polypeptide or the formulation or pharmaceutical composition, is formulated in or with a nanoparticle, a particle, a micelle or a liposome or lipoplex, a polymersome, a polyplex or a dendrimer.

15. The method of claim 1, wherein the APOA1BP polypeptide or the formulation or pharmaceutical composition, is formulated in or as a nanoparticle, a liposome, a tablet, a pill, a capsule, a gel, a geltab, a liquid, a powder, an emulsion, a lotion, an aerosol, a spray, a lozenge, an aqueous or a sterile or an injectable solution, or an implant.

16. The method of claim 15, wherein the implant is an intrathecal implant.

17. The method of claim 15, wherein the nanoparticle, particle, micelle or liposome or lipoplex, polymersome, polyplex or dendrimer further comprise or express a cell or CNS penetrating moiety or peptide or a CNS targeting moiety or peptide.

* * * * *

SEQUENCE LISTING

```
<160> NUMBER OF SEQ ID NOS: 5

<210> SEQ ID NO 1
<211> LENGTH: 76
<212> TYPE: DNA
<213> ORGANISM: artificial sequence
<220> FEATURE:
<223> OTHER INFORMATION: synthetic oligonucleotide

<400> SEQUENCE: 1
atcgattgaa ttccccgggg atcctctaga gtcgacctgc agaagcttgc ctcgagcagc    60
gctgctcgag agatct                                                    76

<210> SEQ ID NO 2
<211> LENGTH: 891
<212> TYPE: DNA
<213> ORGANISM: artificial sequence
<220> FEATURE:
<223> OTHER INFORMATION: synthetic oligonucleotide

<400> SEQUENCE: 2
atgctcaggg gtccgggacc cgggcggctg ctgctgctag cagtcctgtg cctggggaca    60
tcggtgcgct gcaccgaaac cgggaagagc aagaggcagc agagtgtgtg tcgtgcaagg   120
cccatctggt ggggaacaca gcgccgggc tcggagacca tggcgggcgc tgcggtgaag   180
tacttaagtc aggaggaggc tcaggccgtg gaccaagagc tttttaacga gtatcagttc   240
agcgtggatc aactcatgga gctggccggg ttgagctgtg ccacggctat tgccaaggct   300 tatccccca cgtctatgtc caagagtccc ccgactgtct tggtcatctg tggccccgga   360
aataacggag gggatgggct ggtctgtgcg cgacacctca aacttttttgg ttaccagcca   420 actatctatt acccccaaaag acctaacaag cccctcttca ctgggctagt gactcagtgt   480
cagaaaatgg acattccttt ccttggtgaa atgcccccag agcccatgat ggtggacgag   540
ctgtatgagc tggtggtgga cgccatcttc ggcttcagtt tcaagggtga cgttcgggag   600
ccattccaca gcatcctgag tgtcttgagt ggactcactg tgcccattgc tagcatcgac   660
attccctcag gatgggatgt agagaaggga aaccctagcg gaatccaacc agacttactc   720
atctcactga cggcacccaa gaagtctgca actcacttta ctggccgata tcattacctt   780
gggggtcgct ttgtaccacc tgctctagag aagaagtacc agctgaacct gccatcttac   840
```
cctgacacag agtgtgtcta ccgtctacag catcatcatc atcatcatta a        891

<210> SEQ ID NO 3
<211> LENGTH: 296
<212> TYPE: PRT
<213> ORGANISM: artificial sequence
<220> FEATURE:
<223> OTHER INFORMATION: synthetic polynucleotide

<400> SEQUENCE: 3

Met Leu Arg Gly Pro Gly Pro Gly Arg Leu Leu Leu Ala Val Leu
1               5                   10                  15

Cys Leu Gly Thr Ser Val Arg Cys Thr Glu Thr Gly Lys Ser Lys Arg
            20                  25                  30

Gln Gln Ser Val Cys Arg Ala Arg Pro Ile Trp Trp Gly Thr Gln Arg
        35                  40                  45

Arg Gly Ser Glu Thr Met Ala Gly Ala Val Lys Tyr Leu Ser Gln
    50                  55                  60

Glu Glu Ala Gln Ala Val Asp Gln Glu Leu Phe Asn Glu Tyr Gln Phe
65                  70                  75                  80

Ser Val Asp Gln Leu Met Glu Leu Ala Gly Leu Ser Cys Ala Thr Ala
                85                  90                  95

Ile Ala Lys Ala Tyr Pro Pro Thr Ser Met Ser Lys Ser Pro Pro Thr
            100                 105                 110

Val Leu Val Ile Cys Gly Pro Gly Asn Asn Gly Gly Asp Gly Leu Val
        115                 120                 125

Cys Ala Arg His Leu Lys Leu Phe Gly Tyr Gln Pro Thr Ile Tyr Tyr
    130                 135                 140

Pro Lys Arg Pro Asn Lys Pro Leu Phe Thr Gly Leu Val Thr Gln Cys
145                 150                 155                 160

Gln Lys Met Asp Ile Pro Phe Leu Gly Glu Met Pro Pro Glu Pro Met
                165                 170                 175

Met Val Asp Glu Leu Tyr Glu Leu Val Val Asp Ala Ile Phe Gly Phe
            180                 185                 190

Ser Phe Lys Gly Asp Val Arg Glu Pro Phe His Ser Ile Leu Ser Val
        195                 200                 205

Leu Ser Gly Leu Thr Val Pro Ile Ala Ser Ile Asp Ile Pro Ser Gly
    210                 215                 220

Trp Asp Val Glu Lys Gly Asn Pro Ser Gly Ile Gln Pro Asp Leu Leu
225                 230                 235                 240

Ile Ser Leu Thr Ala Pro Lys Lys Ser Ala Thr His Phe Thr Gly Arg
                245                 250                 255

Tyr His Tyr Leu Gly Gly Arg Phe Val Pro Pro Ala Leu Glu Lys Lys
            260                 265                 270

Tyr Gln Leu Asn Leu Pro Ser Tyr Pro Asp Thr Glu Cys Val Tyr Arg
        275                 280                 285

Leu Gln His His His His His His
    290                 295

<210> SEQ ID NO 4
<211> LENGTH: 1121
<212> TYPE: DNA
<213> ORGANISM: homo sapiens

<400> SEQUENCE: 4
gggccgggcc gggccggggg cgcgcgctct gcgagctgga tgtccaggct gcgggcgctg    60

```
ctgggcctcg ggctgctggt tgcgggctcg cgcgtgccgc ggatcaaaag ccagaccatc    120
gcctgtcgct cgggacccac ctggtgggga ccgcagcggc tgaactcggg tggccgctgg    180
gactcagagg tcatggcgag cacggtggtg aagtacctga gccaggagga ggcccaggcc    240
gtggaccagg agctatttaa cgaataccag ttcagcgtgg accaacttat ggaactggcc    300
gggctgagct gtgctacagc catcgccaag gcatatcccc ccacgtccat gtccaggagc    360 cccctactg tcctggtcat ctgtggcccg gggaataatg gaggagatgg tctggtctgt    420
gctcgacacc tcaaactctt tggctacgag ccaaccatct attaccccaa aaggcctaac    480
aagcccctct tcactgcatt ggtgacccag tgtcagaaaa tggacatccc tttccttggg    540
gaaatgcccg cagagcccat gacgattgat gaactgtatg agctggtggt ggatgccatc    600
tttggcttca gcttcaaggg cgatgttcgg gaaccgttcc acagcatcct gagtgtcctg    660
aagggactca ctgtgcccat gccagcatc gacattccct caggatggga cgtggagaag    720
ggaaatgctg gagggatcca gccagacttg ctcatatccc tcacagcccc caaaaaatct    780
gcaacccagt ttaccggtcg ctaccattac ctgggggtc gttttgtgcc acctgctctg    840
gagaagaagt accagctgaa cctgccaccc tacctgaca ccgagtgtgt ctatcgtctg    900
cagtgaggga aggtgggtgg gtattcttcc aataaagac ttagagcccc tctcttccag    960
aactgtggat tcctgggagc tcctctggca ataaaagtca gtgaatggtg gaagtcagag   1020
accaaccctg gggattgggt gccatctctc taggggtaac acaaagggca gaggttgct   1080 atggtatttg gaaacaatga aaatggactg ttagatgcca a                      1121
```

<210> SEQ ID NO 5
<211> LENGTH: 288
<212> TYPE: PRT
<213> ORGANISM: homo sapiens

<400> SEQUENCE: 5

```
Met Ser Arg Leu Arg Ala Leu Leu Gly Leu Gly Leu Leu Val Ala Gly
1               5                   10                  15

Ser Arg Val Pro Arg Ile Lys Ser Gln Thr Ile Ala Cys Arg Ser Gly
            20                  25                  30

Pro Thr Trp Trp Gly Pro Gln Arg Leu Asn Ser Gly Gly Arg Trp Asp
        35                  40                  45

Ser Glu Val Met Ala Ser Thr Val Val Lys Tyr Leu Ser Gln Glu Glu
    50                  55                  60

Ala Gln Ala Val Asp Gln Glu Leu Phe Asn Glu Tyr Gln Phe Ser Val
65                  70                  75                  80

Asp Gln Leu Met Glu Leu Ala Gly Leu Ser Cys Ala Thr Ala Ile Ala
                85                  90                  95

Lys Ala Tyr Pro Pro Thr Ser Met Ser Arg Ser Pro Thr Val Leu
            100                 105                 110

Val Ile Cys Gly Pro Gly Asn Asn Gly Gly Asp Gly Leu Val Cys Ala
        115                 120                 125

Arg His Leu Lys Leu Phe Gly Tyr Glu Pro Thr Ile Tyr Tyr Pro Lys
    130                 135                 140

Arg Pro Asn Lys Pro Leu Phe Thr Ala Leu Val Thr Gln Cys Gln Lys
145                 150                 155                 160

Met Asp Ile Pro Phe Leu Gly Glu Met Pro Ala Glu Pro Met Thr Ile
                165                 170                 175

Asp Glu Leu Tyr Glu Leu Val Val Asp Ala Ile Phe Gly Phe Ser Phe
```

-continued

```
            180                 185                 190
Lys Gly Asp Val Arg Glu Pro Phe His Ser Ile Leu Ser Val Leu Lys
            195                 200                 205

Gly Leu Thr Val Pro Ile Ala Ser Ile Asp Ile Pro Ser Gly Trp Asp
            210                 215                 220

Val Glu Lys Gly Asn Ala Gly Gly Ile Gln Pro Asp Leu Leu Ile Ser
225                 230                 235                 240

Leu Thr Ala Pro Lys Lys Ser Ala Thr Gln Phe Thr Gly Arg Tyr His
                245                 250                 255

Tyr Leu Gly Gly Arg Phe Val Pro Pro Ala Leu Glu Lys Lys Tyr Gln
                260                 265                 270

Leu Asn Leu Pro Pro Tyr Pro Asp Thr Glu Cys Val Tyr Arg Leu Gln
                275                 280                 285
```